(12) United States Patent
Faller et al.

(10) Patent No.: US 6,458,779 B1
(45) Date of Patent: Oct. 1, 2002

(54) HYDROXAMIC ACID DERIVATIVES AS INHIBITORS OF THE PRODUCTION OF HUMAN CD23 AND OF THE TNF RELEASE

(75) Inventors: Andrew Faller, Epping; David Timothy MacPherson; Peter Henry Milner, both of Dunmow; Jayshree Mistry, Welwyn Garden; John Gerald Ward, Barnet, all of (GB)

(73) Assignee: SmithKline Beecham p.l.c., Brentford (GB)

(*) Notice: Subject to any disclaimer, the term of this patent is extended or adjusted under 35 U.S.C. 154(b) by 0 days.

(21) Appl. No.: 09/701,946

(22) PCT Filed: Jun. 22, 1999

(86) PCT No.: PCT/GB99/01954

§ 371 (c)(1), (2), (4) Date: Apr. 5, 2001

(87) PCT Pub. No.: WO99/67201

PCT Pub. Date: Dec. 29, 1999

(30) Foreign Application Priority Data

Jun. 22, 1998 (GB) .............................. 9813451

(51) Int. Cl.$^7$ ...................... A61K 31/545; C07C 259/04
(52) U.S. Cl. ...................... 514/209; 562/623
(58) Field of Search .................. 562/623; 514/311, 514/367, 433, 222.6, 209

(56) References Cited

FOREIGN PATENT DOCUMENTS

| WO | WO94/10990 | 5/1994 |
|---|---|---|
| WO | WO96/02240 | 2/1996 |
| WO | WO96/33165 | 10/1996 |
| WO | WO96/33166 | 10/1996 |
| WO | WO97/02239 | 1/1997 |
| WO | WO 97/02239 | * 1/1997 |
| WO | WO97/15553 | 5/1997 |
| WO | WO 97/43249 | * 11/1997 |
| WO | WO98/43959 | 10/1998 |

* cited by examiner

Primary Examiner—Alan L. Rotman
Assistant Examiner—Hector M Reyes
(74) Attorney, Agent, or Firm—Soma G. Simon; Mary E. McCarthy; Charles M. Kinzig

(57) ABSTRACT

Compounds of Formula (1) wherein: R is methyl substituted by one to three groups from alkyl, aryl, alkenyl, and alkynyl; n is ) or 1; $R^1$ is arylmethyl or heterocyclylmethyl; $R^2$ is alkyl, alkenyl, cycloalkyl or cycloalkenyl; and $R^3$ is hydrogen, alkyl, alkenyl, alkynyl or aryl; are useful in the treatment of disorders mediated y s-CD23.

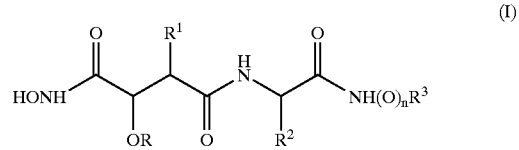

(I)

13 Claims, No Drawings

HYDROXAMIC ACID DERIVATIVES AS INHIBITORS OF THE PRODUCTION OF HUMAN CD23 AND OF THE TNF RELEASE

This invention relates to novel inhibitors of the formation of soluble human CD23 and their use in the treatment of conditions associated with excess production of soluble CD23 (s-CD23) such as autoimmune disease and allergy. The compounds of the invention are also inhibitors of the release of tumour necrosis factor (TNF).

CD23 (the low affinity IgE receptor FceRII, Blast 2), is a 45 kDa type II integral protein expressed on the surface of a variety of mature cells, including B and T lymphocytes, macrophages, natural killer cells, Langerhans cells, monocytes and platelets (Delespesse et al, *Adv Immunol,* 49 [1991] 149–191). There is also a CD23-like molecule on eosinophils (Grangette et al, *J Immunol,* 143 [1989] 3580–3588). CD23 has been implicated in the regulation of the immune response (Delespesse et al, *Immunol Rev,* 125 [1992] 77–97). Human CD23 exists as two differentially regulated isoforms, a and b, which differ only in the amino acids at the intracellular N-terminus (Yokota et al, *Cell,* 55 [1988] 611–618). In man the constitutive a isoform is found only on B-lymphocytes, whereas type b, inducible by IL4, is found on all cells capable of expressing CD23.

Intact, cell bound CD23 (i-CD23) is known to undergo cleavage from the cell surface leading to the formation of a number of well-defined soluble fragments (s-CD23), which are produced as a result of a complex sequence of proteolytic events, the mechanism of which is still poorly understood (Bourget et al *J Biol Chem,* 269 [1994] 6927–6930). Although not yet proven, it is postulated that the major soluble fragments (Mr 37, 33, 29 and 25 kDa) of these proteolytic events, all of which retain the C-terminal lectin domain common to i-CD23, occur sequentially via initial formation of the 37 kDa fragment (Letellier et al, *J Exp Med,* 172 [1990] 693–700). An alternative intracellular cleavage pathway leads to a stable 16 kDa fragment differing in the C-terminal domain from i-CD23 (Grenier-Brosette et al, *Eur J Immunol,* 22 [1992] 1573–1577).

Several activities have been ascribed to membrane bound i-CD23 in humans, all of which have been shown to play a role in IgE regulation. Particular activities include: a) antigen presentation, b) IgE mediated eosinophil cytotoxicity, c) B cell homing to germinal centres of lymph nodes and spleen, and d) downregulation of IgE synthesis (Delespesse et al, *Adv Immunol,* 49, [1991] 149–191). The three higher molecular weight soluble CD23 fragments (Mr 37, 33 and 29 kDa) have multifunctional cytokine properties which appear to play a major role in IgE production. Thus, the excessive formation of s-CD23 has been implicated in the overproduction of IgE, the hallmark of allergic diseases such as extrinsic asthma, rhinitis, allergic conjuctivitis, eczema, atopic dermatitis and anaphylaxis (Sutton and Gould, *Nature,* 366, [1993] 421–428). Other biological activities attributed to s-CD23 include the stimulation of B cell growth and the induction of the release of mediators from monocytes. Thus, elevated levels of s-CD23 have been observed in the serum of patients having B-chronic lymphocytic leukaemia (Sarfati et al, *Blood,* 71 [1988] 94–98) and in the synovial fluids of patients with rheumatoid arthritis (Chomarat et al, *Arthritis and Rheumatism,* 36 [1993] 234–242). That there is a role for CD23 in inflammation is suggested by a number of sources. First, sCD23 has been reported to bind to extracellular receptors which when activated are involved in cell-mediated events of inflammation. Thus, sCD23 is reported to directly activate monocyte TNF, IL-1, and IL-6 release (Armant et al, vol 180, J.Exp. Med., 1005–1011 (1994)). CD23 has been reported to interact with the B2-integrin adhesion molecules, CD11b and CD11c on monocyte/macrophage (S. Lecoanet-Henchoz et al, Immunity, vol 3; 119–125 (1995)) which trigger $NO_2^-$, hydrogen peroxide and cytokine (IL-1, IL-6, and TNF) release. Finally, IL-4 or IFN induce the expression of CD23 and its release as sCD23 by human monocytes. Ligation of the membrane bound CD23 receptor with IgE/anti-IgE immune complexes or anti CD23 mAb activates cAMP and IL-6 production and thromboxane B2 formation, demonstrating a receptor-mediated role of CD23 in inflammation.

Because of these various properties of CD23, compounds which inhibit the formation of s-CD23 should have twofold actions of a) enhancing negative feedback inhibition of IgE synthesis by maintaining levels of i-CD23 on the surface of B cells, and b) inhibiting the immunostimulatory cytokine activities of higher molecular weight soluble fragments (Mr 37, 33 and 29 kDa) of s-CD23. In addition, inhibition of CD23 cleavage should mitigate sCD23-induced monocyte activation and mediator formation, thereby reducing the inflammatory response.

TNFα is a pro-inflammatory cytokine which is released from stimulated cells by specific cleavage of a 76-amino acid signal sequence in the inactive precursor to generate the mature form. The cleavage of TNFα has been reported to be carried out by a metalloprotease (Gearing, A. J. H. et al, (1994) Nature 370, 555–557; McGeehan, G. M. et al, (1994) Nature 370, 558–561; Mohler, K. M. et al, (1994) Nature 370, 218–220). Compounds reported to inhibit the cleavage of TNFα by the TNF processing enzyme can be broadly described as matrix metalloprotease inhibitors, particularly of the hydroxamic acid class.

TNFα is induced in a variety of cell types in response to bacteria, endotoxin, various viruses and parasites, so that one physiological function ascribed to TNFα is a contribution to the inflammatory response to acute infection by bacteria, parasites, etc (Dinarello, C. A. (1992) Immunol. 4, 133–145). Overproduction of TNFα has been implicated in disease states such as rheumatoid arthritis, septic shock, Crohn's disease and cachexia (Dinarello, 1992). Inhibition of processing of TNFα to the mature, active form would therefore be beneficial in the treatment of these inflammatory disorders. TNFα may also contribute to the destruction of tissue in autoimmune disease although it is not a initiating factor in these diseases. Confirming the importance of TNFα in rheumatoid arthritis, TNFα antibodies have been shown to reduce the severity of disease in short term studies in rheumatoid arthritis models (Elliott, M. J., et al (1993) Arthrit. Rheum. 12, 1681–1690; Elliott et al (1994) Lancet 344, 1125–1127).

International Patent Application No. WO 96/02240 (Smithkline Beecham plc) discloses that compounds which inhibit the action of matrix metalloproteases (e.g. collagenase, stromelysin and gelatinase) are effective inhibitors of the release of human soluble CD23 transfected into mammalian cell culture systems.

UK Patent Application No. 9601041.8 (Smithkline Beecham plc) discloses that certain compounds of formula (I) are effective inhibitors of the release of human soluble CD23 transfected into mammalian cell culture systems:

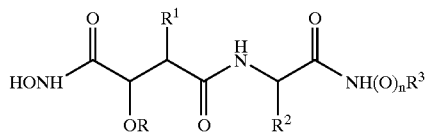

(I)

According to the present invention, there is provided a compound of formula (I) above, wherein:

n is 0 or 1;

R is methyl substituted by one to three groups selected from alkyl, aryl, alkenyl, and alkynyl;

$R^1$ is arylmethyl or heterocyclylmethyl;

$R^2$ is alkyl, alkenyl, aryl, cycloalkyl or cycloalkenyl; and $R^3$ is hydrogen, alkyl, alkenyl, alkynyl or aryl.

Alkyl, alkenyl and alkynyl groups referred to herein include straight and branched groups containing up to six carbon atoms and are optionally substituted by one or more groups selected from the group consisting of aryl, heterocyclyl, $(C_{1-6})$alkylthio, $(C_{1-6})$alkoxy, aryl$(C_{1-6})$alkoxy, aryl$(C_{1-6})$alkylthio, amino, mono- or di-$(C_{1-6})$alkylamino, cycloalkyl, cycloalkenyl, carboxy and esters thereof, hydroxy, and halogen.

Cycloalkyl and cycloalkenyl groups referred to herein include groups having between three and eight ring carbon atoms and are optionally substituted as described hereinabove for alkyl, alkenyl and alkynyl groups.

When used herein, the term "aryl" means single and fused rings suitably containing from 4 to 7, preferably 5 or 6, ring atoms in each ring, which rings, may each be unsubstituted or substituted by, for example, up to three substituents. A fused ring system may include aliphatic rings and need include only one aromatic ring.

Suitable aryl groups include phenyl and naphthyl such as 1-naphthyl or 2-naphthyl.

Suitably any aryl group, including phenyl and naphthyl, may be optionally substituted by up to five, preferably up to three substituents. Suitable substituents include halogen, $(C_{1-6})$alkyl, aryl, aryl$(C_{1-6})$alkyl, $(C_{1-6})$alkoxy, $(C_{1-6})$alkoxy $(C_{1-6})$alkyl, halo$(C_{1-6})$alkyl, aryl$(C_{1-6})$alkoxy, hydroxy, nitro. cyano, azido, amino, mono- and di-N-$(C_{1-6})$ alkylamino, acylamino, arylcarbonylamino, acyloxy, carboxy, carboxy salts, carboxy esters, carbamoyl, mono- and di-N-$(C_{1-6})$alkylcarbamoyl, $(C_{1-6})$alkoxycarbonyl, aryloxycarbonyl, ureido, guanidino, sulphonylamino, aminosulphonyl, $(C_{1-6})$alkylthio, $(C_{1-6})$alkyl sulphinyl, $(C_{1-6})$alkylsulphonyl, heterocyclyl and heterocyclyl $(C_{1-6})$alkyl. In addition, two adjacent ring carbon atoms may be linked by a $(C_{3-5})$alkylene chain, to form a carbocyclic ring.

When used herein the terms "heterocyclyl" and "heterocyclic" suitably include, unless otherwise defined, aromatic and non-aromatic, single and fused, rings suitably containing up to four heteroatoms in each ring, each of which is selected from oxygen, nitrogen and sulphur, which rings, may be unsubstituted or substituted by, for example, up to three substituents. Each heterocyclic ring suitably has from 4 to 7, preferably 5 or 6, ring atoms. A fused heterocyclic ring system may include carbocyclic rings and need include only one heterocyclic ring.

Preferably a substituent for a heterocyclyl group is selected from halogen, $(C_{1-6})$alkyl, aryl$(C_{1-6})$alkyl, $(C_{1-6})$ alkoxy, $(C_{1-6})$alkoxy$(C_{1-6})$alkyl, halo$(C_{1-6})$alkyl, hydroxy, amino, mono- and di-N-$(C_{1-6})$alkyl-amino, acylamino, car boxy salts, carboxy esters, carbamoyl, mono- and di-N-$(C_{1-6})$alkylcarbonyl, aryloxycarbonyl, $(C_{1-6})$ alkoxycarbonyl$(C_{1-6})$alkyl, aryl, oxy groups, ureido, guanidino, sulphonylamino, aminosulphonyl, $(C_{1-6})$ alkylthio, $(C_{1-6})$alkylsulphinyl, $(C_{1-6})$alkylsulphonyl, heterocyclyl and heterocyclyl$(C_{1-6})$alkyl.

In a particular aspect of the invention, R is allyl, propyl, ethyl or isopropyl, and/or $R^1$ is 1- or 2-naphthylmethyl; and/or $R^2$ is t-butyl; and/or $R^3$ is hydrogen or methyl. In a further aspect of the invention, each of R to $R^3$ is selected from the group consisting of the values ascribed to it in the Examples hereinbelow. Preferably, the compound of formula (I) of the invention is selected from the group consisting of the compounds described in the Examples hereinbelow.

According to a further aspect, the present invention provides the use of a compound of formula (I) for the production of a medicament for the treatment or prophylaxis of disorders such as allergy, inflammatory disorders and autoimmune disease in which the overproduction of s-CD23 is implicated.

In a further aspect the invention provides a method for the treatment or prophylaxis of disorders such as allergy, inflammatory disorders and autoimmune disease in which the overproduction of s-CD23 is implicated, which method comprises the administration of a compound of formula (I), to a human or non-human mammal in need thereof.

The invention also provides a pharmaceutical composition for the treatment or prophylaxis of disorders such as allergy, inflammatory disorders and autoimmune disease in which the overproduction of s-CD23 is implicated which comprises a compound of formula (I) and optionally a pharmaceutically acceptable carrier therefor.

According to a further aspect, the present invention provides the use of a compound of formula (I) for the production of a medicament for the treatment or prophylaxis of conditions mediated by TNF, including, but not limited to, inflammation, fever, cardiovascular effects, haemorrhage, coagulation and acute phase response, cachexia and anorexia, acute infections, shock states, graft versus host reactions and autoimmune disease.

In a further aspect the invention provides a method for the treatment or prophylaxis of conditions mediated by TNF, which method comprises the administration of a compound of formula (I), to a human or non-human mammal in need thereof.

The invention also provides a pharmaceutical composition for the treatment or prophylaxis of conditions mediated by TNF, which comprises a compound of formula (I) and optionally a pharmaceutically acceptable carrier therefor.

Particular inflammatory disorders include CNS disorders such as Alzheimers disease, multiple sclerosis, and multi-infarct dementia, as well as the inflammation mediated sequelae of stroke and head trauma.

It is to be understood that the pharmaceutically acceptable salts, solvates and other pharmaceutically acceptable derivatives of the compound of formula (I) are also included in the present invention.

Salts of compounds of formula (I) include for example acid addition salts derived from inorganic or organic acids, such as hydrochlorides, hydrobromides, hydroiodides, p-toluenesulphonates, phosphates, sulphates, acetates, trifluoroacetates, propionates, citrates, maleates, fumarates, malonates, succinates, lactates, oxalates, tartarates and benzoates.

Salts may also be formed with bases. Such salts include salts derived from inorganic or organic bases, for example alkali metal salts such as sodium or potassium salts, and organic amine salts such as morpholine, piperidine, dimethylamine or diethylamine salts.

It has surprisingly been found that the compounds of the present invention are potent and selective inhibitors of CD23 processing and TNF release, whilst exhibiting reduced collagenase inhibitory activity in comparison with the above-mentioned compounds of the prior art. The compounds of the invention also exhibit advantageous in-vivo absorption properties via the oral route.

The compounds of the invention may be prepared by use of any appropriate conventional method, for example by analogy with the methods disclosed in patent publication WO97/02239 (BBL).

Accordingly, a further aspect of the invention provides a process for preparing a compound of formula (I) as defined hereinabove, which process comprises:

(a) deprotecting a compound of formula (II):

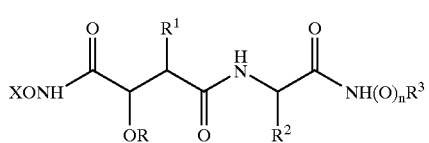

(II)

wherein n and R to $R^3$ are as defined hereinabove, and X is a protecting group such as benzyl or trimethylsilyl or (b) reacting a compound of formula (III):

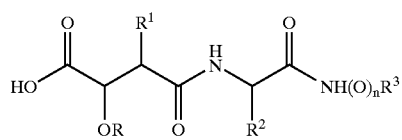

(III)

wherein n and R to $R^3$ are as defined hereinabove, and any hydroxy group is optionally protected, with hydroxylamine or a salt thereof, or (c) converting a compound of formula (I) to a different compound of formula (I) as defined hereinabove.

Compounds of formulae (II) and (III) are novel and form a further aspect of the invention.

Compounds of formula (II) can be prepared from compounds of formula (III) by reaction with a protected hydroxylamine. Compounds of formula (III) having one or more protected hydroxy groups can be converted by hydrolysis to a corresponding unprotected compound of formula (III).

Suitable protecting groups for a hydroxamic acid are well known in the art and include benzyl, trimethylsilyl, t-butyl and t-butyldimethylsilyl.

Suitable protecting groups for a carboxylic acid are well known in the art and include t-butyl, benzyl and methyl.

Compounds of formula (III) can be prepared by reacting a compound of formula (IV) or (IVa):

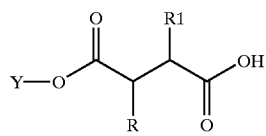

(IV)

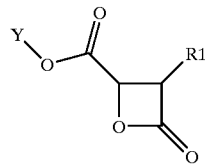

(IVa)

wherein R and $R^1$ are as defined hereinabove and Y is a protecting group for carboxyl, with a compound of formula (V):

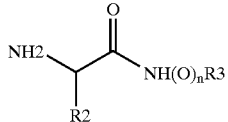

(V)

wherein n, $R^2$ and $R^3$ are as defined hereinabove, or an activated derivative thereof. If (IVa) is used a subsequent alkylation or acylation of the hydroxyl group may then be required.

Compounds of formula (IV) can be prepared by protecting a corresponding compound in which Y is hydrogen, which in turn can be prepared by:

(a) reacting a compound of formula (VI):

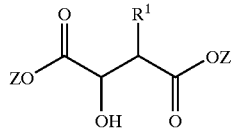

(VI)

wherein $R^1$ is as defined hereinabove and Z is a protecting group for carboxyl, with an alkylating agent; and (b) removing the protecting groups.

Compounds of formula (VI) wherein Z is hydrogen can be prepared by reacting a diester (such as the dimethyl or diethyl ester) of 2-hydroxy succinic acid with a compound of formula $R^1X'$ in the presence of a strong base such as lithium diisopropylamide, wherein X' is a leaving group such as bromine or iodine, and then hydrolysing the resulting compound to remove the ester groups.

The isomers, including stereoisomers, of the compounds of the present invention may be prepared as mixtures of such isomers or as individual isomers. The individual isomers may be prepared by any appropriate method, for example individual stereoisomers may be prepared by stereospecific chemical synthesis starting from chiral substrates or by separating mixtures of diastereoisomers using known methods. In a preferred aspect, the invention provides compounds of formula (IA):

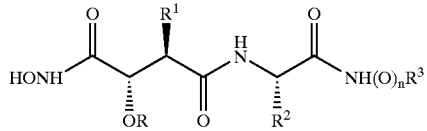

(IA)

It is preferred that the compounds are isolated in substantially pure form.

As stated herein an inhibitor of the formation of soluble human CD23 has useful medical properties. Preferably the active compounds are administered as pharmaceutically acceptable compositions.

The compositions are preferably adapted for oral administration. However, they may be adapted for other modes of administration, for example in the form of a spray, aerosol or other conventional method for inhalation, for treating respiratory tract disorders; or parenteral administration for patients suffering from heart failure. Other alternative modes of administration include sublingual or transdermal administration.

The compositions may be in the form of tablets, capsules, powders, granules, lozenges, suppositories, reconstitutable powders, or liquid preparations, such as oral or sterile parenteral solutions or suspensions.

In order to obtain consistency of administration it is preferred that a composition of the invention is in the form of a unit dose.

Unit dose presentation forms for oral administration may be tablets and capsules and may contain conventional excipients such as binding agents, for example syrup, acacia, gelatin, sorbitol, tragacanth, or polyvinylpyrrolidone; fillers, for example lactose, sugar, maize-starch, calcium phosphate, sorbitol or glycine; tabletting lubricants, for example magnesium stearate; disintegrants, for example starch, polyvinylpyrrolidone, sodium starch glycollate or microcrystalline cellulose; or pharmaceutically acceptable wetting agents such as sodium lauryl sulphate.

The solid oral compositions may be prepared by conventional methods of blending, filling or tabletting. Repeated blending operations may be used to distribute the active agent throughout those compositions employing large quantities of fillers. Such operations are of course conventional in the art. The tablets may be coated according to methods well known in normal pharmaceutical practice, in particular with an enteric coating.

Oral liquid preparations may be in the form of, for example, emulsions, syrups, or elixirs, or may be presented as a dry product for reconstitution with water or other suitable vehicle before use. Such liquid preparations may contain conventional additives such as suspending agents, for example sorbitol, syrup, methyl cellulose, gelatin. hydroxyethylcellulose, carboxymethylcellulose, aluminium stearate gel, hydrogenated edible fats; emulsifying agents, for example lecithin, sorbitan monooleate, or acacia; non-aqueous vehicles (which may include edible oils), for example almond oil, fractionated coconut oil, oily esters such as esters of glycerine, propylene glycol, or ethyl alcohol; preservatives, for example methyl or propyl p-hydroxybenzoate or sorbic acid; and if desired conventional flavouring or colouring agents.

For parenteral administration, fluid unit dosage forms are prepared utilizing the compound and a sterile vehicle, and, depending on the concentration used, can be either suspended or dissolved in the vehicle. In preparing solutions the compound can be dissolved in water for injection and filter sterilized before filling into a suitable vial or ampoule and sealing. Advantageously, adjuvants such as a local anaesthetic, a preservative and buffering agents can be dissolved in the vehicle. To enhance the stability, the composition can be frozen after filling into the vial and the water removed under vacuum. Parenteral suspensions are prepared in substantially the same manner, except that the compound is suspended in the vehicle instead of being dissolved, and sterilization cannot be accomplished by filtration. The compound can be sterilized by exposure to ethylene oxide before suspending in the sterile vehicle. Advantageously, a surfactant or wetting agent is included in the composition to facilitate uniform distribution of the compound.

Compositions of this invention may also suitably be presented for administration to the respiratory tract as a snuff or an aerosol or solution for a nebulizer, or as a microfine powder for insufflation, alone or in combination with an inert carrier such as lactose. In such a case the particles of active compound suitably have diameters of less than 50 microns, preferably less than 10 microns for example diameters in the range of 1–50 microns, 1–10 microns or 1–5 microns. Where appropriate, small amounts of other anti-asthmatics and bronchodilators, for example sympathomimetic amines such as isoprenaline, isoetharine, salbutamol, phenylephrine and ephedrine; xanthine derivatives such as theophylline and aminophylline and corticosteroids such as prednisolone and adrenal stimulants such as ACTH may be included.

The compositions may contain from 0.1% to 99% by weight, preferably from 10–60% by weight, of the active material, depending upon the method of administration. A preferred range for inhaled administration is 10–99%, especially 60–99%, for example 90, 95 or 99%.

Microfine powder formulations may suitably be administered in an aerosol as a metered dose or by means of a suitable breath-activated device.

Suitable metered dose aerosol formulations comprise conventional propellants, cosolvents, such as ethanol, surfactants such as oleyl alcohol, lubricants such as oleyl alcohol, desiccants such as calcium sulphate and density modifiers such as sodium chloride.

Suitable solutions for a nebulizer are isotonic sterilised solutions, optionally buffered, at for example between pH 4–7, containing up to 20 mg/ml of compound but more generally 0.1 to 10 mg/ml, for use with standard nebulisation equipment.

An effective amount will depend on the relative efficacy of the compounds of the present invention, the severity of the disorder being treated and the weight of the sufferer. Suitably, a unit dose form of a composition of the invention may contain from 0.1 to 1000 mg of a compound of the invention (0.001 to 10 mg via inhalation) and more usually from 1 to 500 mg, for example 1 to 25 or 5 to 500 mg. Such compositions may be administered from 1 to 6 times a day, more usually from 2 to 4 times a day, in a manner such that the daily dose is from 1 mg to 1 g for a 70 kg human adult and more particularly from 5 to 500 mg. That is in the range of about $1.4 \times 10^{-2}$ mg/kg/day to 14 mg/kg/day and more particularly in the range of about $7 \times 10^{-2}$ mg/kg/day to 7 mg/kg/day.

The following examples illustrate the invention but do not limit it in any way.

BIOLOGICAL TEST METHODS

Procedure 1

The ability of test compounds to inhibit the release of soluble CD23 was investigated by use of the following procedure.

RPMI 8866 Cell Membrane CD23 Cleavage Activity Assay

Plasma membranes from RPMI 8866 cells, a human Epstein-Barr virus transformed B-cell line (Sarfati et al., Immunology 60 [1987] 539–547) expressing high levels of CD23 are purified using an aqueous extraction method. Cells resuspended in homogenization buffer (20 mM HEPES pH 7.4, 150 mM NaCl, 1.5 mM $MgCl_2$, 1 mM DTT) are broken by $N_2$ cavitation in a Parr bomb and the plasma membrane fraction mixed with other membranes is recovered by centrifugation at 10,000×g. The light pellet is resuspended in 0.2 M potassium phosphate, pH 7.2 using 2 ml per 1–3 g wet cells and the nuclear pellet is discarded. The membranes are further fractionated by partitioning between Dextran 500 (6.4% w/w) and polyethylene glycol (PEG) 5000 (6.4% w/w) (ref), at 0.25 M sucrose in a total of 16 g per 10–15 mg membrane proteins [Morre and Morre, BioTechniques 7, 946–957 (1989)]. The phases are separated by brief centrifugation at 1000×g and the PEG (upper) phase is collected, diluted 3–5 fold with 20 mM potassium phosphate buffer pH 7.4, and centrifuged at 100,000×g to recover membranes in that phase. The pellet is resuspended in phosphate-buffered saline and consists of 3–4 fold enriched plasma membranes as well as some other cell membranes (e.g. lysosomes, Golgi). The membranes are aliquoted and stored at −80° C. Fractionation at 6.6% Dextran/PEG yields plasma membranes enriched 10-fold.

The fractionated membranes are incubated at 370° C. for times up to 4 hrs to produce fragments of CD23 which are separated from the membrane by filtration in 0.2 micron Durapore filter plates (Millipore) after quenching the assay with 5 uM Preparation 1 from P30994. sCD23 released from the membrane is determined using the EIA kit from The Binding Site (Birmingham, UK) or a similar one utilizing MHM6 anti-CD23 mAb [Rowe et al., Int. J. Cancer, 29, 373–382 (1982)] or another anti-CD23 mAb as the capture antibody in a sandwich EIA. The amount of soluble CD23 made by 0.5 ug membrane protein in a total volume of 50 ul phosphate-buffered saline is measured by EIA and compared to the amount made in the presence of various concentrations of inhibitors. Inhibitors are prepared in solutions of water or dimethylsulfoxide (DMSO) and the final DMSO concentration is not more than 2%. IC50's are determined by curve fitting as the concentration where 50% inhibition of production of sCD23 is observed relative to the difference in sCD23 between controls incubated without inhibitor.

Procedure 2

The ability of test compounds to inhibit collagenase was investigated using the following procedure.
Collagenase Inhibition Assay The potency of compounds to act as inhibitors of collagenase was determined by the method of Cawston and Barrett (Anal. Biochem. 99, 340–345, 1979), hereby incorporated by reference, whereby a 1 mM solution of the inhibitor being tested or dilutions thereof, was incubated at 37° C. for 18 h with collagen and human recombinant collagenase, from synovial fibroblasts cloned, expressed and purified from *E. Coli*, (buffered with 150 mM Tris, pH 7.6, containing 15 mM calcium chloride, 0.05% Brij 35, 200 mM sodium chloride and 0.02% sodium azide). The collagen was acetylated $^3$H type 1 bovine collagen prepared by the method of Cawston and Murphy (methods in Enzymology 80, 711,1981) The samples were centrifuged to sediment undigested collagen and an aliquot of the radioactive supernatant removed for assay on a scintillation counter as a measure of hydrolysis. The collagenase activity in the presence of 1 mM inhibitor, or dilution thereof, was compared to activity in a control devoid of inhibitor and the results reported as that concentration effecting 50% of the collagenase ($IC_{50}$).

Procedure 3

The ability of test compounds to inhibit TNF release was investigated using the following procedure.

Assay for Inhibition of Release of TNFα from Human Monocytes Stimulated by Lipopolysaccharide (LPS) Endotoxin Human moncytes, cultured in RPMI 1640 medium supplemented with 10% fetal calf serum, are centrifuged at 1000×g for 5 min and then resuspended in medium at $2×10^6$ cells/ml. The cell suspension is aliquoted in 24 well plates, 1 ml per well. Compounds to be tested are dissolved in neat dimethyl sulfoxide (DMSO) and added to culture with the final DMSO concentration at 0.1%. Compounds are added to cells in triplicate wells. TNFα release is stimulated by addition of LPS to the cells at a final concentration of 200 ng/ml. Appropriate control cultures are set up in triplicates also. The plates are incubated for 18–20 hrs at 37° C., 5% $CO_2$, then centrifuged at 1000×g for 5 min. A specific ELISA for human TNFα (SmithKline Beecham) is used to measure TNF levels in the cell-free culture supernatants.

Preparation of N-[4-t-Butoxy-3S-(hydroxy)-2R-(2-naphthylmethyl)succinyl]-S-tert-leucinamide a) 3S-t-Butoxycarbonyl-2R-(2-naphthylmethyl) propiolactone

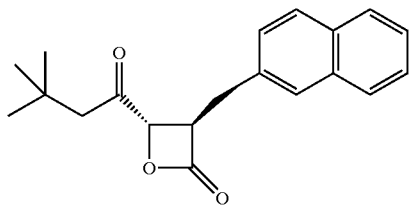

(t-Butyl-(3R)-carboxy-4-(2-naphthyl)butyrate (10 g, 31.9 mmol) in THF (160 ml) was stirred at −70° C. under argon and lithium bis(trimethylsilyl)amide (63.7 ml of 1 M solution in THF, 63.7 mmol) was added dropwise. The mixture was stirred at between −60° C. and −70° C. for 1 hr and then cooled to −80° C. and N-iodosuccinimide (7.17 g, 31.9 mmol) in THF (20 ml) was added via cannula. The mixture was allowed to warm to ~−30° C. over 1 hr and was then quenched with saturated ammonium chloride solution. Ethyl acetate was added and the 2-phase mixture was stirred rapidly at room temperature for 1.5 hrs. The layers were separated and the aqueous layer was extracted with ethyl acetate (2×) and the combined organic layers were washed with 5% sodium thiosulfate solution and brine and then dried ($Na_2SO_4$) and evaporated. Chromatography on silica gel (elution with 10% ethyl acetate in hexane) and trituration of the recovered product with hexane gave 5.70 g of a white solid (63%).

MS (AP+ve) M+Na=335

$^1$H NMR ($CDCl_3$): 1.31 (9H, s), 3.29 (1H, dd, J=8.5, 14.6 Hz), 3.38 (1H, dd, J=6.1, 14.6 Hz), 4.06(1H, m), 4.45 (1H, d, J=4.4 Hz), 7.34 (1H, dd, J=1.7, 8.5 Hz), 7.48 (2H, m), 7.68 (1H, s), 7.82 (3H, m).

b) N-[4-t-Butoxy-3S-(hydroxy)-2R-(2-naphthylmethyl) succinyl]-S-tert-leucinamide

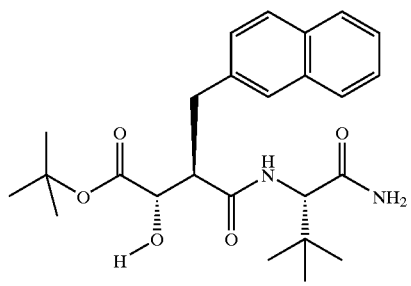

To 3S-t-Butoxycarbonyl-2R-(2-naphthylmethyl)propiolactone (5.0 g, 16.0 mmol) and (S)-t-leucinamide (2.47 g,19.2 mmol) were stirred together in THF (30 ml) at room temperature for 48 hrs. The THF was evaporated, ethyl acetate was added and the solution was washed with 2N HCl, water and brine and then dried (MgSO$_4$) and evaporated. The resulting solid was triturated with hexane and dried to give 6.373 g of product (90%).

MS (ES+ve) M+Na=465, M+H=443

$^1$H NMR (DMSO-d$_6$): 0.91 (9H, s), 1.39 (9H, s), 2.85–3.20 (3H, m), 3.85 (1H, dd, J=5.0, 7.4 Hz), 4.17 (1H, d, J=9.3 Hz), 5.65 (1H, d, J=7.4 Hz), 6.91 (1H, s), 7.29 (1H, s), 7.38–7.48 (3H, m), 7.69 (1H, s), 7.80–7.87 (4H, m).

Preparation of N-4-t-Butoxy-3S-(hydroxy)-2R-(2-naphthylmethyl)succinyl-S-tert-leucine methylamide

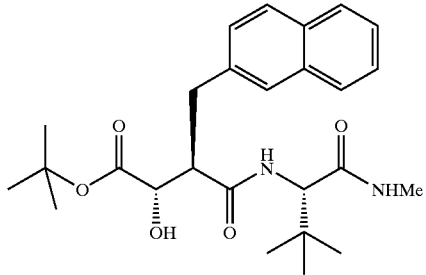

Carried out via opening of 3S-t-Butoxycarbonyl-2R-(2-Naphthylmethyl)propiolactone with tert-leucine methylamide as in b) above to give product as a white solid.

MS (AP+ve) M+H=457, M+Na=479

$^1$H NMR (DMSO-d$_6$): 0.85 (9H, s), 1.41 (9H, s), 2.32 (3H, d, J=4.6 Hz), 2.90 (1H, dd, J=6.5, 13.5 Hz), 3.03 (1H, dd, J=8.6, 13.5 Hz), 3.14 (1H, m), 3.88 (1H, dd, 5.7, 7.3 Hz), 4.12 (1H, d, J=9.3 Hz), 5.62 (1H, d, J=7.5 Hz), 7.36 (1H, m), 7.45 (2H, m), 7.60 (1H, m), 7.65 (1H, s), 7.77–7.90 (4H, m).

Preparation of N-[4-t-Butoxy-3S-(hydroxy)-2R-(2-naphthylmethyl)succinyl]-S-tert-leucine ethylamide

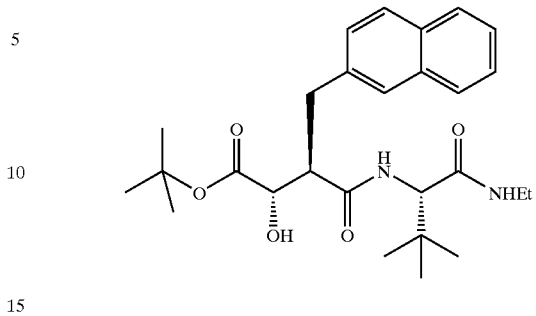

Carried out via opening of 3S-t-Butoxycarbonyl-2R-(2-Naphthylmethyl)propiolactone with tert-leucine ethylamide as in b) to above give product as a white solid (86%).

MS (ES+ve) M+H=471, M+Na=493

$^1$H NMR (DMSO-d$_6$): 0.84 (3H, t, J=7.3 Hz), 0.86 (9H, s), 1.41 (9H, s), 2.80–2.92 (3H, m), 3.03 (1H, dd, J=8.5, 13.6 Hz), 3.16 (1H, m), 3,88 (1H, dd, J=5.8, 7.3 Hz), 4.12 (1H, d, J=9.4 Hz), 5.63 (1H, d, J=7.4 Hz), 7.37 (1H, dd, J=1.5, 8 Hz), 7.44–7.47 (2H, m), 7.65 (1H, m), 7.70 (1H, m), 7.77–7.81 (4H, m).

Preparation of 3S-Hydroxy-2R-(2-(7-fluoro)naphthylmethyl)succinic acid diethyl ester a) 2-Bromomethyl-6-fluoronaphthalene

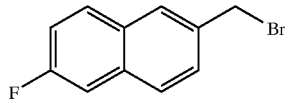

6-Fluoro-2-methylnaphthalene (20.5 g, 128 mmol, prepared by adaptation of the method of Wolinska-Mocydlarz et al[2]) and NBS (22.8 g, 128 mmol) were heated at reflux for 16 hr in CCl$_4$ (210 mL) during which time, benzoyl peroxide (2.5 g) was added portionwise. The cooled solution was filtered and evaporated and the residue was extracted thoroughly with hexane (4×250 mL). The extracts were decanted from tarry material, combined and evaporated to give the product as a yellow solid, 29.8 g (97%).

$^1$H NMR (CDCl$_3$): 4.65 (2H, s), 7.27 (1H, dt, J=9, 3 Hz), 7.43 (1H, dd, J=10, 2 Hz), 7.53 (1H, dd, J=9, 1 Hz), 7.74–7.85 (3H, m).

b) 3S-Hydroxy-2R-(2-(7-fluoro)naphthylmethyl)succinic acid diethyl ester

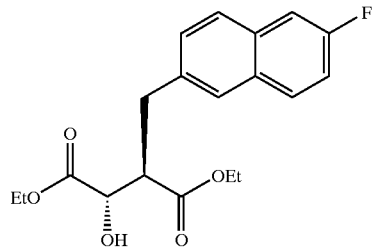

A mixture of LHMDS soln (1.0M in THF, 262 mL) and THF (80 mL) was cooled to −72° C., and a solution of diethyl S-malate (23.7 g, 124.6 mmol) in THF (100 mL), was added dropwise keeping the reaction at <−68° C. The mixture was allowed to warm to −40° C. for 15 min and then re-cooled to −72° C. 2-Bromomethyl-6-fluoronaphthalene (29.8 g, 124.7 mmol) in THF 180 mL was added dropwise and the mixture was stirred overnight while slowly warming to room temp. The mixture was poured into 0.5 M HCl and extracted with Et$_2$O (2×), the combined extracts were washed with 0.5 M HCl, NaHCO$_3$ solution water and brine; dried (MgSO$_4$) and evaporated to an oil which was chromatographed on silica (hexane/Et$_2$O, 0 to 35%) giving the product as a gum which subsequently solidified, 17.3 g (40%).

$^1$H NMR (CDCl$_3$): 1.20 (3H, t, J=7 Hz), 1.27 (3H, t, J=7 Hz), 3.14 (1H, dd, J=12, 9 Hz), 3.20–3.42 (3H, m), 4.09–4.29 (5H, m), 7.25 (1H, dt, J=9, 2.5 Hz), 7.43 (2H, m), 7.73 (1H, s), 7.75–7.89 (2H, m).

REFERENCES

1. G M Carrera and D Garvey, J. Heterocyclic Chem, 1992, 29, 847.
2. J Wolinska-Mocydlarz, P Canonne and L C Leitch, Synthesis, 1974, 566.

EXAMPLE 1

N'-[3S-(Allyloxy)-4-(N-hydroxyamino)-2R-(2-naphthylmethyl)succinyl]-S-tert-leucinamide a) N-[4-t-Butoxy-3S-(allyloxy)-2R-(2-naphthylmethyl)succinyl]-S-tert-leucinamide

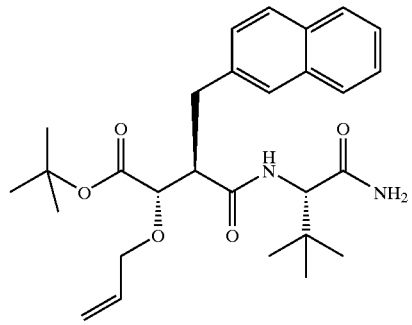

To a solution of N-[4-t-Butoxy-3S-(hydroxy)-2R-(2-naphthylmethyl)succinyl]-S-tert-leucinamide (221 mg, 0.5 mmol) in tBuOH (10 ml) was added allyl bromide (0.4 ml, 5 mmol) followed by NaH (60% dispersion in mineral oil, 22 mg). Stirred for 1 h then poured into dil HCl and extracted with diethyl ether. The extracts were washed with water, dried (MgSO$_4$) and evaporated. The residue was chromatographed (50% ethyl acetate/hexane) to give the product as a white foam.

MS (ES+ve) M+Na=505, M+H=483

$^1$H NMR (DMSO-d$_6$): 0.75 (9H, s), 1.30 (9H, s), 2.64 (1H, dd, J=14,4.5 Hz), 2.90 (1H, dd, J=14,10 Hz), 3.06–3.2 (1H, m), 3.69–3.75 (1H, obs), 3.74 (1H, d, J=8 Hz), 3.89 (1H, d, J=8 Hz), 4.03 (1H, d, J=9 Hz), 5.02 (1H, dd, J=10,2 Hz), 5.14 (1H, dd, J=17,2 Hz), 5.64–5.75 (1H, m), 6.71 (1H, br), 7.03 (1H br), 7.16 (1H, dd, J=8.5,1.5 Hz), 7.28–7.33 (2H, m), 7.48 (1H, s), 7.62–7.71 (4H, m).

b) N-[3S-(Allyloxy)-4-hydroxy-2R-(2-naphthylmethyl)succinyl]-S-tert-leucinamide

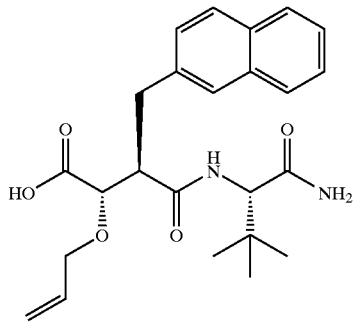

A solution of N-[4-t-Butoxy-3S-(allyloxy)-2R-(2-naphthylmethyl)succinyl]-S-tert-leucinamide (0.18 g, 0.4 mmol) in dichloromethane/trifluoroacetic acid (5/2 ml) was stirred for 18 h. Concentrated to yield product as a white solid.

MS (ES+ve) M+Na=449, M+H=427

$^1$H NMR (DMSO-d$_6$): 0.9 (9H, s), 2.85 (1H, dd, J=14,4.5 Hz), 3.05 (1H, dd, J=14,10 Hz), 3.22–3.31 (1H, m), 3.85 (1H, dd, J=12.5,5.5), 3.94 (1H, d, J=8 Hz), 4.08 (1H, dd, J=12.5,5 Hz), 4.17 (1H, d, J=9 Hz), 5.15 (1H, d, J=10 Hz), 5.41 (1H, d, J=17), 5.87–5.90 (1H, m), 6.87 (1H, br), 7.17 (1H, br), 7.33 (1H, d, J=8.5 Hz), 7.43–7.47 (2H, m), 7.65 (1H, s), 7.62–7.71 (4H, m).

c) N'-[3S-(Allyloxy)-4-(N-hydroxyamino)-2R-(2-naphthylmethyl)succinyl]-S-tert-leucinamide

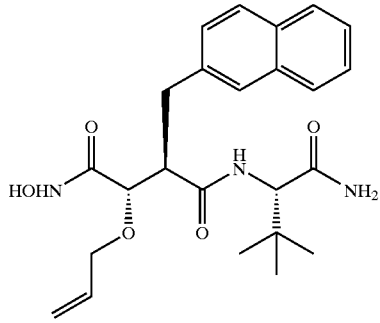

A solution of N-[3S-(allyloxy)-4-hydroxy-2R-(2-naphthylmethyl)succinyl]-S-tert-leucinamide (0.96 g, 2.25 mmol) in anhydrous DMF (10 ml) was treated sequentially with HOAT (0.613 g, 4.50 mmol) and EDC (0.846 g, 4.50 mmol), and the reaction solution was stirred at room temperature for 0.25 h. Hydroxylamine hydrochloride (0.47 g, 6.75 mmol) and N-methylmorpholine (0.682 g, 6.75 mmol) were then added and the reaction solution was stirred for 16 h at room temperature. The reaction solution was evaporated to dryness and the residue was partitioned between ethyl acetate and 10% citric acid. The phases were separated and the organic phase was washed with further 10% citric acid (×2) and satd. sodium bicarbonate solution (×3). Precipitated product was filtered off, washed with water and ethyl acetate and then dried in vacuo to afford the title compound as a white solid (0.22 g, 22%). The organic phase from the filtrate was washed with brine, dried (MgSO$_4$) and evaporated and the residue was recrystallised from methanol/diethyl ether to afford the title compound (0.26 g, 26%).

MS (ES−ve) M−H=440

$^1$H NMR (DMSO-d$_6$): 0.97 (9H, s), 2.64 (1H, m), 2.93 (1H, m), 3.23 (1H, m), 3.81 (2H, m), 3.95 (1H, m),4.12 (1H, d, J=9.4 Hz), 5.11 (1H, d, J=10.6 Hz), 5.23 (1H, d, J=17.3

Hz), 5.78 (1H, m), 6.75 (1H, s), 6.96 (1H, s), 7.25 (1H, d J=8.7 Hz), 7.43 (2H, m), 7.59 (1H, s), 7.65–7.83 (4H, m), 9.12 (1H, s), 10.95 (1H, s).

N-[3S-(Allyloxy)-4-hydroxy-2R-(2-naphthylmethyl) succinyl]-S-tert-leucinamide can also be prepared from (3R-Naphthylmethyl)-2S-hydroxy succinic acid diethyl ester as follows:

d) 3S-Allyloxy-2R-naphthylmethylsuccinic acid diethyl ester

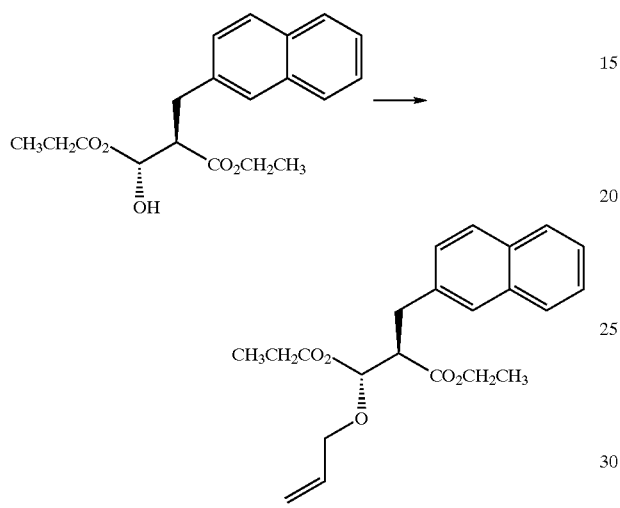

To a stirred solution of (3R-Naphthylmethyl)-2S-hydroxy succinic acid diethyl ester (4.0 g, 12 mmol) in benzene (80 ml) was added thallium (I) ethoxide (2.99 g, 12 mmol) and the mixture was stirred at room temperature. A gelatinous precipitate was formed and after 1 hr, the solvent was removed in vacuo. The precipitate was then suspended in DMF (120 ml) and allyl bromide (1.45 g, 1.04 ml, 12 mmol) was added and the mixture was stirred at room temperature overnight. The mixture was filtered to remove thallium salts, water and ethyl acetate were added and the product was extracted into ethyl acetate. The extracts were washed successively with water and brine and then dried (MgSO$_4$) and concentrated. Purification by chromatography on silica gel (elution with 5% ethyl acetate in 40–60-petroleum ether) gave the product as an oil (1.40 g, 32%).

MS (ES+ve) M+Na=393

$^1$H NMR (CDCl$_3$): 1.10 (3H, t, J=7.2 Hz), 1.29 (3H, t, J=7.2 Hz), 3.03 (1H, dd, J=6.9, 13.5 Hz), 3.16–3.33 (2H, m), 3.91 (1H, dd, J=6.1, 12.6 Hz), 4.02–4.30 (6H, m), 5.20 (1H, dd, J=1.3, 10.3 Hz), 5.28 (1H, dd, J=1.6, 17.2 Hz), 5.91 (1H, m), 7.33 (1H, dd, J=1.7, 8.4 Hz), 7.45 (2H, m), 7.64 (1H, s), 7.78 (3H, m).

e) Using known methodology e.g. WO9702239, 3S-Allyloxy-2R-naphthylmethylsuccinic acid diethyl ester can be hydrolysed, treated with trifluoroacetic anhydride then methanol, coupled to (S)-tert-leucinamide and hydrolysed to give N-[3S-(Allyloxy)-4-hydroxy-2R-(2-naphthylmethyl)succinyl]-S-tert-leucinamide. Spectral data as for example 1b) above.

EXAMPLE 2

N'-[3S-(Allyloxy)-4-(N-hydroxyamino)-2R-(2-naphthylmethyl)succinyl]-S-tert-leucine methylamide

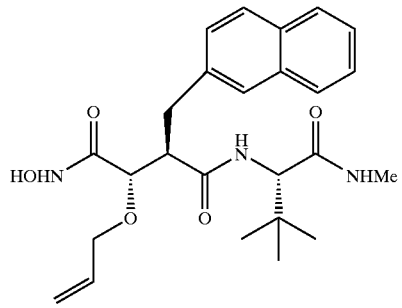

Prepared analogously to example 1d)+e) from 3S-Allyloxy-2R-naphthylmethylsuccinic acid diethyl ester, but coupling with N-Methyl-(S)-tert-leucinamide instead of (S)-tert-leucinamide.

MS (ES+ve) M+H=456, M+Na=478

$^1$H NMR (DMSO-d$_6$): 0.81 (9H, s), 2.05 (3H, d, J=4.4 Hz), 2.65 and 2.80 (2H, m), 3.25 (1H, m), 3.78 and 3.93 (2H, dd, J=12.7, 5.4 Hz), 3.85 (1H, d, J=9.7 Hz), 4.05 (1H, d, J=9.5 Hz), 5.09 (1H, dd, J=10.4, 1.6 Hz), 5.22 (1H, dd, J=17.3, 1.6 Hz), 5.75 (1H, m), 7.12 (1H, d, J=4.4 Hz), 7.24 (1H, m), 7.46 (2H, m), 7.57 (1H, s), 7.75 (4H, m), 9.14 (1H, s), 10.99 (1H, s).

EXAMPLE 3

N'-[4-(N-Hydroxyamino)-2R-(2-naphthylmethyl)-3S-(propyloxy)succinyl]-S-tert-leucine methylamide

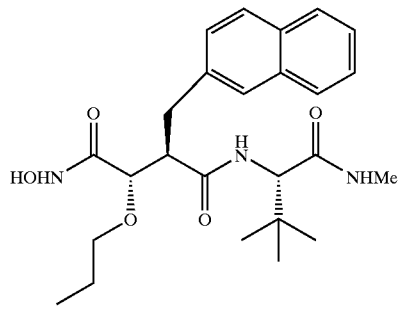

Prepared analogously to example 2 from 3S-Allyloxy-2R-naphthylmethylsuccinic acid diethyl ester, but the compound was hydrogenated using Pd/BaSO$_4$ prior to hydroxamic acid formation.

MS (ES+ve) M+H=458, M+Na=480

$^1$H NMR (DMSO-d$_6$): 0.82 (12H, m), 1.43 (2H, m), 2.04 (3H, d, J=4.4 Hz), 2.64 and 2.81 (2H, m), 3.25 (3H, m), 3.78 (1H, d, J=9.6 Hz), 4.03 (1H, d, J=9.4 Hz), 7.06 (1H, d, J=4.4 Hz), 7.25 (1H, d, J=8.5 Hz), 7.44 (2H, m), 7.57 (1H, s), 7.62 (1H, d, J=9.4 Hz), 7.80 (3H, m), 9.14 (1H, s), 10.95 (1H, s).

EXAMPLE 4

N'-[4-(N-Hydroxyamino)-2R-(2-naphthylmethyl)-3S-(propyloxy)succinyl]-S-tert-leucinamide

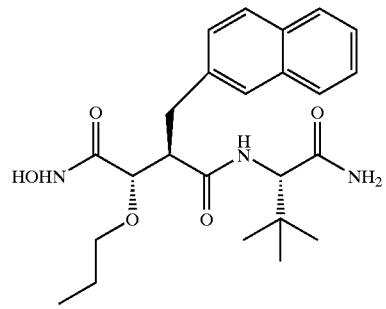

Prepared analogously to example 1d)+e) from 3S-Allyloxy-2R-naphthylmethylsuccinic acid diethyl ester, but the compound was hydrogenated using Pd/BaSO$_4$ prior to hydroxamic acid formation.

MS (ES+ve) M+H=444, M+Na=466

$^1$H NMR (DMSO-d$_6$): 0.82 (3H, t, J=7.5 Hz), 0.89 (9H, s), 1.45 (2H, m), 2.64 and 2.91 (2H, m), 3.12–3.40 (3H, m), 3.75 (1H, d, J=9.5 Hz), 4.11 (1H, d, J=9.5 Hz), 6.79 (1H, s), 6.97 (1H, s), 7.25 (1H, m), 7.44 (2H, m), 7.59 (1H, s), 7.73 (4H, m), 9.10 (1H, br s) and 10.95 (1H, s).

EXAMPLE 5

N'-[3S-(Allyloxy)-4-(N-hydroxyamino)-2R-(2-(7-fluoro)naphthylmethyl)succinyl]-S-tert-leucinamide

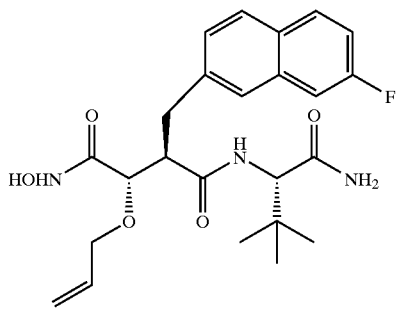

Prepared analogously to example 1d)+e) from 3S-Hydroxy-2R-(2-(7-fluoro)naphthylmethyl)succinic acid diethyl ester.

MS (ES–ve) M–H=458

$^1$H NMR (DMSO-d$_6$): 0.89 (9H, s), 2.69 (1H, dd, J=14,4 Hz), 2.95 (1H, dd, J=14,10Hz), 3.11–3.19 (1H, m), 3.74–3.81 (2H, m), 3.96 (1H, dd, J=12.5,5 Hz), 4.07(1H, d, J=9.5 Hz), 5.10 (1H, dd, J=10,1 Hz), 5.22 (1H, dd, J=16,1 Hz), 5.75–5.86 (1H, m), 6.69 (1H, s), 7.11 (1H, s), 7.24 (1H, d, J=9.5 Hz), 7.33 (1H, dd, J=9,2.5 Hz), 7.54 (1H, dd, J=10.5,2.5 Hz), 7.59 (1H, s), 7.77 (1H, d, J=8.5 Hz), 7.77–7.82 (1H, obs), 7.89 (1H, dd, J=8.5,6 Hz), 9.12 (1H, s), 10.91 (1H, s).

EXAMPLE 6

N'-[3S-(Ethoxy)-4-(N-hydroxyamino)-2R-(2-(7-fluoro)naphthylmethyl)succinyl]-S-tert-leucinamide

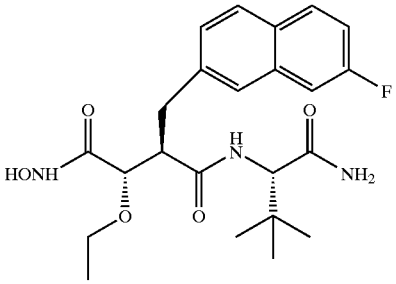

Prepared analogously to example 1d)+e) from 3S-Hydroxy-2R-(2-(7-fluoro)naphthylmethyl)succinic acid diethyl ester, alkylating with iodoethane instead of allyl bromide.

MS (ES–ve) M–H=446

$^1$H NMR (DMSO-d$_6$): 0.89 (9H, s), 1.05 (3H, t, J=7 Hz), 2.63 (1H, dd, J=14,3 Hz), 2.90 (1H, dd, J=14,10.5 Hz), 3.17 (1H, dd, J=9,3 Hz), 3.23–3.27 (1H m), 3.31–3.47 (1H, m), 3.75 (1H, d, J=9 Hz), 4.11(1H, d, J=9.5 Hz), 6.76 (1H,s), 6.93 (1H, s), 7.22 (1H, dd, J=8.5,1 Hz), 7.32 (1H, dt, J=8.5,2.5 Hz), 7.53–7.58 (1H, obs), 7.58 (1H, s), 7.65 (1H, d, J=9 Hz), 7.78 (1H, d, J=8.5 Hz), 7.90 (1H, dd, J=9,6 Hz), 9.11 (1H, s), 10.94 (1H, s).

EXAMPLE 7

N'-[4-(N-Hydroxyamino)-2R-(2-(7-fluoro)naphthylmethyl)-3S-(propyloxy)succinyl]-S-tert-leucinamide

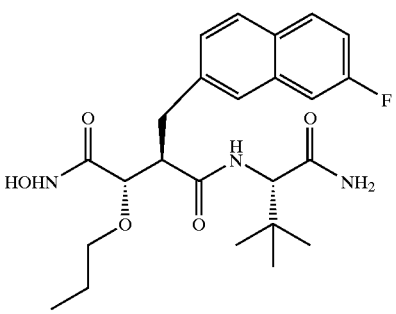

Prepared analogously to example 5 from 3S-Hydroxy-2R-(2-(7-fluoro)naphthylmethyl)succinic acid diethyl ester, but hydrogenating using Pd/C prior to hydroxamic acid preparation.

MS (ES–ve) M–H=460

$^1$H NMR (DMSO-d$_6$): 0.82 (3H, t, J=7.5 Hz), 0.89 (9H, s), 1.40–1.52 (2H, m), 2.63 (1H, dd, J=14,3.5 Hz), 2.89 (1H, dd, J=14,10 Hz), 3.15–3.37 (3H, m), 3.75 (1H, d, J=9.5 Hz), 4.09 (1H, d, J=9.5 Hz), 6.75 (1H, s), 6.91 (1H, s), 7.23 (1H, dd, J=8,1 Hz), 7.32 (1H, dt, J=8.5,2), 7.58 (1H, s), 7.49–7.60 (2H, m), 7.78 (1H, d, J=8.5), 7.90 (1H, dd, J=9,8 Hz), 9.10 (1H, br) and 10.91 (1H, br).

EXAMPLE 8

N'-[3S-(Ethoxy)-4-(N-hydroxyamino)-2R-(2-naphthylmethyl)succinyl]-S-tert-leucinamide

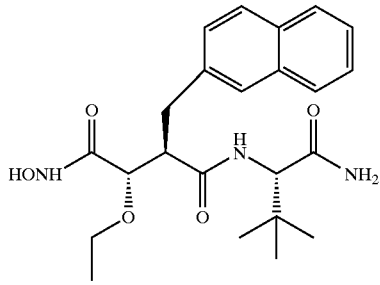

Prepared analogously to example 1a)+b)+c) from N-4-t-Butoxy-3S-(hydroxy)-2R-(2-naphthylmethyl)succinyl]-S-tert-leucinamide by alkylation with iodoethane instead of allyl bromide.

MS (ES−ve) M−H=460

$^1$H NMR (DMSO-d$_6$): 0.94 (9H, s), 1.06 (3H, t, J=7 Hz), 2.68 (1H, dd, J=14,4 Hz), 2.94 (1H, dd, J=24,11 Hz), 3.05–3.19 (1H, m), 3.22–3.29 (1H, m), 3.36–3.47 (1H, m), 3.70 (1H, d, J=8.5 Hz), 4.09(1H, d, J=9.5 Hz), 6.78 (1H, s) 7.22 (1H, s), 7.28 (1H, d, J=8.5 Hz), 7.42–7.48 (2H, m), 7.61 (1H, s), 7.76 (1H, d, J=8.5 Hz), 7.80–7.87 (3H, m), 8.97 (1H, s), 10.92 (1H, s).

EXAMPLE 9

N'-[4-(N-Hydroxyamino)-2R-(2-naphthylmethyl)-3S-(propyloxy)succinyl]-S-(β,β-dimethyl-Nε-methyllysinamide).TFA salt

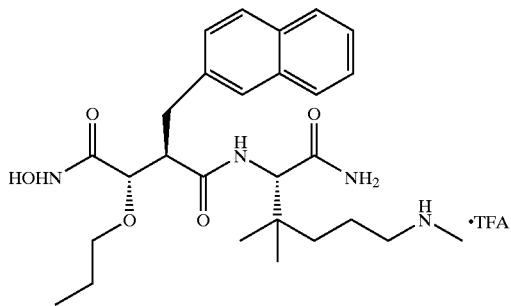

Prepared analogously to example 1d)+e) from 3S-Allyloxy-2R-naphthylmethylsuccinic acid diethyl ester, but the compound was coupled with β,β-dimethyl-Nε-methyl-lysinamide (instead of (S)-tert-leucinamide) and was hydrogenated using Pd/BaSO$_4$ prior to hydroxamic acid formation.

MS (ES−ve) M−H=499, MS (ES+ve) M+H=501

$^1$H NMR (DMSO-d$_6$): 0.84 (3H, t, J=7.4 Hz), 0.86 (6H, s), 1.22 (2H, m), 1.48 (2H, m), 1.55 (2H, m), 2.55 (3H, s), 2.70 (3H, m), 2.93 (1H, m), 3.21 (2H, m), 3.35 (1H, m, partially obscured by water), 3.76 (1H, d, J=8.9 Hz), 4.17 (1H, d, J=9.5 Hz), 6.82 (1H, s), 6.95 (1H, s), 7.27 (1H, m), 7.43 (2H, m), 7.59 (1H, s), 7.76 (4H, m), 8.25 (2H, br s), 9.12 (1H, s), 10.91 (1H, s).

EXAMPLE 10

N'-[4-(N-Hydroxyamino)-2R-(2-(6-fluoro)naphthylmethyl)-3S-(propyloxy)succinyl]-S-tert-leucinamide

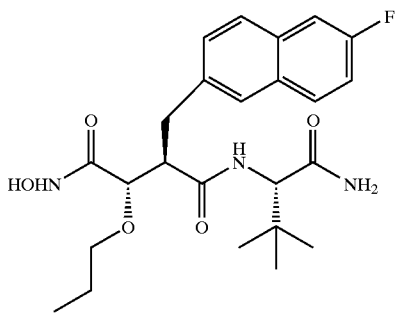

Prepared analogously to example 1d)+e) from 2R-(2-(6-Fluoro)naphthylmethyl)-3S-hydroxy succinic acid diethyl ester, the compound being hydrogenated using Pd/C prior to hydroxamic acid formation.

MS (ES−ve) M−H=460, MS (ES+ve) M+H=462

$^1$H NMR (DMSO-d$_6$): 0.82 (3H, t, J=7 Hz), 0.88 (9H, s), 1.45 (2H, m), 2.63 (1H, br d, J≈12 Hz), 2.89 (1H, br t), 3.20 (2H, m), ca 3.3 (1H, m, partially obscured by water signal), 3.76 (1H, d, J=9 Hz), 4.08 (1H, d, J=9 Hz), 6.71 (1H, br s), 6.89 (1H, br s), 7.28–7.36 (2H, m), 7.58–7.63 (3H, m), 7.74 (1H, d, J=8 Hz), 7.86–7.89 (1H, m), 9.09 (1H, br s), 10.90 (1H, br s).

EXAMPLE 11

N'-[3S-(Allyloxy)-4-(N-Hydroxyamino)-2R-(2-(6-Fluoro)naphthylmethyl)succinyl]-S-tert-leucinamide

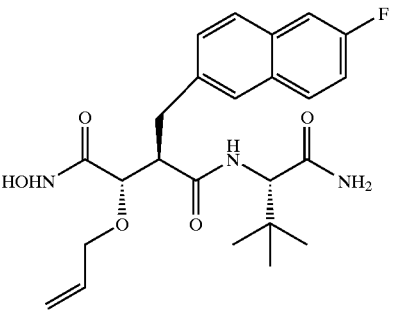

Prepared analogously to example 1d)+e) from 2R-(2-(6-Fluoro)naphthylmethyl)-3S-hydroxy succinic acid diethyl ester.

MS (ES−ve) M−H=458, MS (ES+ve) M+H=460

$^1$H NMR (DMSO-d$_6$): 0.87 (9H, s), 2.64 (1H, dd, J=14,3 Hz), 2.90 (1H, dd, J≈14, 14 Hz), 3.22 (1H, m), 3.78 (1H, dd, J=13, 6 Hz), 3.82 (1H, d, J=10 Hz), 3.95 (1H, dd, J=13, 5 Hz), 4.10 (1H, d, J=9 Hz), 5.10 (1H, d, J=10 Hz), 5.22 (1H, dd, J=17, 1 Hz), 5.73–5.83 (1H, m), 6.71 (1H, br s), 6.92 (1H, br. s), 7.29 (1H, d, J=8 Hz), 7.34 (1H, m), 7.58–7.67 (3H, m), 7.74 (1H, d, J=8 Hz), 7.88 1H, m), 9.10 (1H, br s), 10.95 (1H, br s).

EXAMPLE 12

N'-[3S-(Hexyloxy)-4-(N-Hydroxyamino)-2R-(2-(6-Fluoro)naphthylmethyl)succinyl]-S-tert-leucinamide

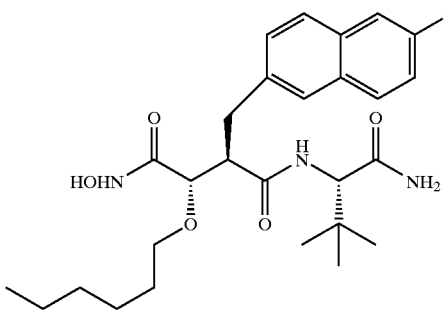

Prepared analogously to example 1d)+e) from 2R-(2-(6-Fluoro)naphthylmethyl)-3S-hydroxy succinic acid diethyl ester, alkylating using hexyl iodide instead of allyl bromide.

MS (ES−ve) M−H=502, MS (ES+ve) M+H=504, M+Na=526

$^1$H NMR (DMSO-d$_6$): 0.85 (3H, t, J=7 Hz), 0.88 (9H, s), 1.22 (6H, br m), 1.43 (2H, m), 2.64 (1H, m), 2.90 (1H, m), 3.20 (2H, m), 3.35 (1H, m), 3.75 (1H, d, J=9 Hz), 4.08 (1H, d, J=9 Hz), 6.72 (1H, b, s), 6.90 (1H, br s), 7.27–7.39 (2H, m), 7.57–7.65 (3H, m), 7.74 (1H, d, J=9 Hz), 7.87 (1H, m), 9.10 (1H, br s), 10.90 (1H, br s).

EXAMPLE 13

N'-[3S-((4-Fluoro)benzyloxy)-4-(N-hydroxyamino)-2R-(2-naphthylmethyl)succinyl]-S-tert-leucinamide

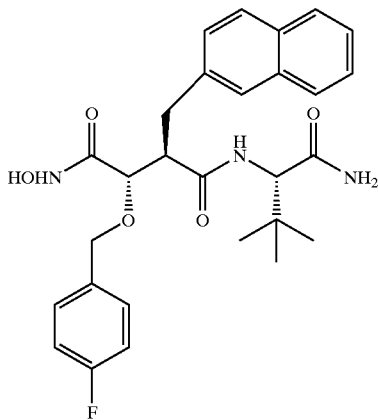

Prepared analogously to example 1a)+b)+c) from N-4-t-Butoxy-3S-(hydroxy)-2R-(2-naphthylmethyl)succinyl]-S-tert-leucinamide by alkylation with 4-Fluorobenzylbromide instead of allyl bromide.

MS (ES−ve) M−H=508, MS (ES+ve) M+H=510, M+Na=532

$^1$H NMR (DMSO-d$_6$): 0.76 (9H, s), 2.69 (1H, m), 2.95 (1H, m), 3.25 (1H, m), 3.94 (1H, d, J=9 Hz), 4.09 (1H, d, J=9 Hz), 4.30 (1H, A of Abq, J=11 Hz), 4.46 (1H, B of Abq, J=11 Hz), 6.75 (1H, br s), 6.98 (1H, br s), 7.13 (2H, m), 7.24–7.35 (3H, m), 7.42–7.46 (2H, m), 7.60 (1H, br s), 7.66 (1H, d, J≈10 Hz), 7.74 (1H, d, J=8 Hz), 7.81 (2H, m), 9.17 (1H, br s), 11.00 (1H br s).

EXAMPLE 14

N'-[3S-((4-Fluoro)benzyloxy)-4-(N-hydroxyamino)-2R-(2-(6-fluoro)naphthylmethyl)succinyl]-S-tert-leucinamide

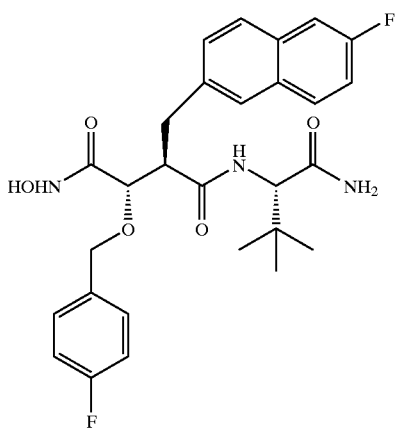

Prepared analogously to example 1d)+e) from 2R-(2-(6-Fluoro)naphthylmethyl)-3S-hydroxy succinic acid diethyl ester, alkylating using 4-Flurobenzylbromide instead of allyl bromide.

MS (ES−ve) M−H=526, MS (ES+ve) M+H=528

$^1$H NMR (DMSO-d$_6$): 0.76 (9H, s), 2.68 (1H, m), 2.93 (1H, m), 3.27 (1H, m), 3.95 (1H, d, J=10 Hz), 4.08 (1H, d, J=8 Hz), 4.28 (1H, A of Abq, J=11 Hz), 4.46 (1H, B of Abq, J=11 Hz), 6.73 (1H, br s), 6.93 (1H, br s), 7.12 (2H, m), 7.29–7.39 (4H, m), 7.57–7.68 (3H, m), 7.74 (1H, d, J=9 Hz), 7.89 (1H, m), 9.17 (1H, br s), 11.00 (1H, br s).

EXAMPLE 15

N'-[3S-Benzoyloxy-4-(N-hydroxyamino)-2R-(2-naphthylmethyl)succinyl]-S-tert-leucinamide

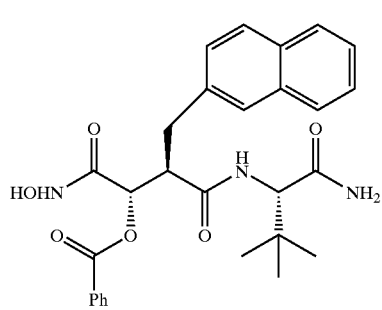

Prepared as for example 1a)+b)+c) from N-[4-t-Butoxy-3S-(hydroxy)-2R-(2-naphthylmethyl)succinyl]-S-tert-leucinamide by acylation with benzoyl chloride instead of alkylation with allyl bromide.

MS (ES−ve) M−H=504, MS (ES+ve) M+H=506, M+Na=528

$^1$H NMR (DMSO-d$_6$): 0.73 (9H, s), 2.73–2.89 (1H, m), 3.00–3.10 (1H, m), 3.58–3.67 (1H, m), 4.10 (1H, d, J=9 Hz), 5.21 (1H, d, J=10 Hz), 6.73 (1H, br s), 7.10 (1H, br s), 7.31 (1H, d, J=9 Hz), 7.43–7.52 (4H, m), 7.65 (2H, m), 7.74–7.85 (3H, m), 8.04 (3H, m), 9.15 (1H, s), 11.22 (1H, s).

EXAMPLE 16

N'-[3S-(2-(N,N-Dimethylacetamidoxy))-4-(N-hydroxyamino)-2R-(2-naphthylmethyl)succinyl]-S-tert-leucinamide

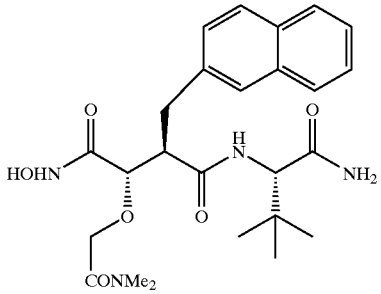

Prepared analogously to example 1a)+b)+c) from N-[4-t-Butoxy-3S-(hydroxy)-2R-(2-naphthylmethyl)succinyl]-S-tert-leucinamide by alkylation with 2-Bromo-N,N-dimethylacetamide instead of allyl bromide.

MS (ES−ve) M−H=485, MS (ES+ve) M+H=487, M+Na=509

$^1$H NMR (DMSO-$d_6$): 0.85 (9H, s), ca 2.75–2.83 (1H, m), 2.79 (3H, s), 2.91 (3H, s), 3.01 (1H, dd, J=14, 10 Hz), ca 3.3 (1H, m), 3.94 (1H, d, J=8 Hz), 4.06–4.15 (3H, m), 6.78 (1H, s), 7.03 (1H, s), 7.29 (1H, d, J=8 Hz), 7.39–7.46 (2H, m), 7.63 (1H, s), ca 7.64 (1H, d, J=8 Hz), 7.75 (1H, d, J=8 Hz), 7.79–7.83 (2H, m), 9.09 (1H, s), 11.18 (1H, br m).

EXAMPLE 17

N'-[3S-(2-(N-t-Butylacetamidoxy))-4-(N-hydroxyamino)-2R-(2-naphthylmethyl)succinyl]-S-tert-leucinamide

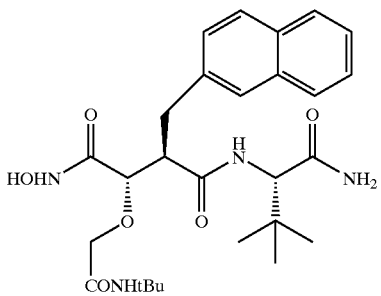

Prepared analogously to example 1a)+b)+c) from N-[4-t-Butoxy-3S-(hydroxy)-2R-(2-naphthylmethyl)succinyl]-S-tert-leucinamide by alkylation with bromoacetonitrile instead of allyl bromide and subsequent treatment with TFA prior to hydroxamic acid preparation.

MS (ES−ve) M−H=508, MS (ES+ve) M+H=510, M+Na=532

$^1$H NMR (DMSO-$d_6$): 0.89 (9H, s), 1.29 (9H, s), 2.67–2.75 (1H, m), 2.90–2.96 (1H, m), ca 3.33 (1H, m), 3.62 & 3.78 (2×1H, Abq, J≈15 Hz), 3.93 (1H, d, J=9 Hz), 4.22 (1H, d, J=10 Hz), 6.82 (1H, s), 7.04 (1H, s), 7.11 (1H, s), 7.27 (1H, d, J=8 Hz), 7.41–7.47 (2H, m), 7.60 (1H, s), 7.75 (1H, d, J=9 Hz), 7.81–7.84 (2H, m), 7.90 (1H, d, J=8 Hz), 9.19 (1H, s), 11.13 (1H, br s).

EXAMPLE 18

N'-[4-(N-Hydroxyamino)-2R-(2-naphthylmethyl)-3S-(N-phenylcarbamoyloxy)-succinyl]-S-tert-leucinamide

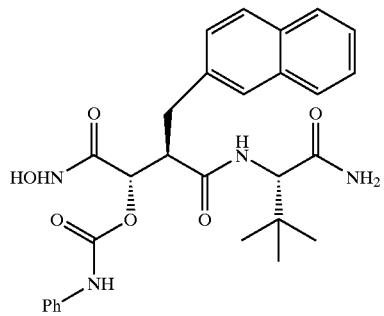

Prepared analogously to example 1a)+b)+c) from N-[4-t-Butoxy-3S-(hydroxy)-2R-(2-naphthylmethyl)succinyl]-S-tert-leucinamide by acylation with phenylisocyanate/DMAP instead of alkylation with allyl bromide.

MS (ES−ve) M−H=519, MS (ES+ve) M+H=521

$^1$H NMR (DMSO-$d_6$): 0.83 (9H, s), 2.76 (1H, dd, J=12,4 Hz), 2.95–3.08 (1H, m), 3.36–3.41 (1H, m), 4.17 (1H, d, J=9.5 Hz), 5.17 (1H, d, J=9.5 Hz), 6.78 (1H, br), 6.91–7.00 (1H, m), 7.19 (1H, br), 7.22–7.32 (3H, m), 7.41–7.45 (4H, m), 7.6–7.7 (1H, obs), 7.61 (1H, s), 7.75 (1H, d, J=9.5 Hz), 7.76–7.82 (2H, m), 9.08 (1H, s), 9.62 (1H, br), 11.09 (1H, br).

EXAMPLE 19

N'-[4-(N-Hydroxyamino)-3S-(N-methyl-N-phenylcarbamoyloxy)-2R-(2-naphthylmethyl)-succinyl]-S-tert-leucinamide

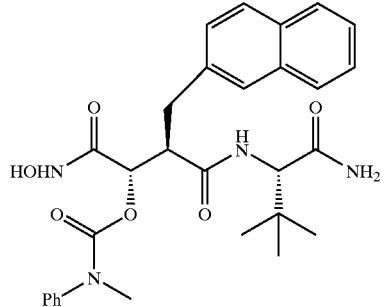

Prepared analogously to example 1a)+b)+c) from N-[4-t-Butoxy-3S-(hydroxy)-2R-(2-naphthylmethyl)succinyl]-S-tert-leucinamide by acylation with N-methyl-N-Phenylcarbamoyl chloride/NaH instead of alkylation with allyl bromide (see example 27).

MS (ES−ve) M−H=533, MS (ES+ve) M+H=535

$^1$H NMR (DMSO-$d_6$): 0.78 (9H, s), 2.76 (1H, dd, J=14,4 Hz), 2.98 (1H, dd, J=14,10.5 Hz), 3.26 (3H,s), 3.35–3.41 (1H, m), 4.10 (1H, d, J=9 Hz), 5.03 (1H, d, J=9 Hz), 6.72 (1H, s), 7.06 (1H, s), 7.18 (1H, t, J=6 Hz), 7.25–7.38 (5H, m), 7.38–7.46 (3H, m), 7.60 (1H, s), 7.74 (1H, d, J=9 Hz), 7.79–7.90 (2H, m), 9.08 (1H, s), 11.02 (1H, br.).

EXAMPLE 20

N'-[3S-(Cyclohexyloxy)-4-(N-hydroxyamino)-2R-(2-naphthylmethyl)succinyl]-S-tert-leucinamide

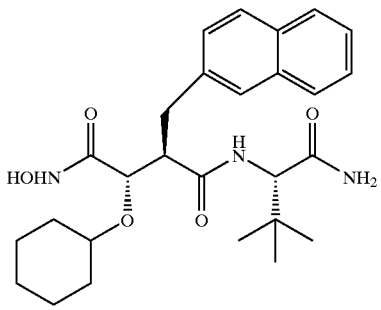

a) N-[4-t-Butoxy-3S-(cyclohexyloxy)-2R-(2-Naphthylmethyl)succinyl]-S-tert-leucinamide

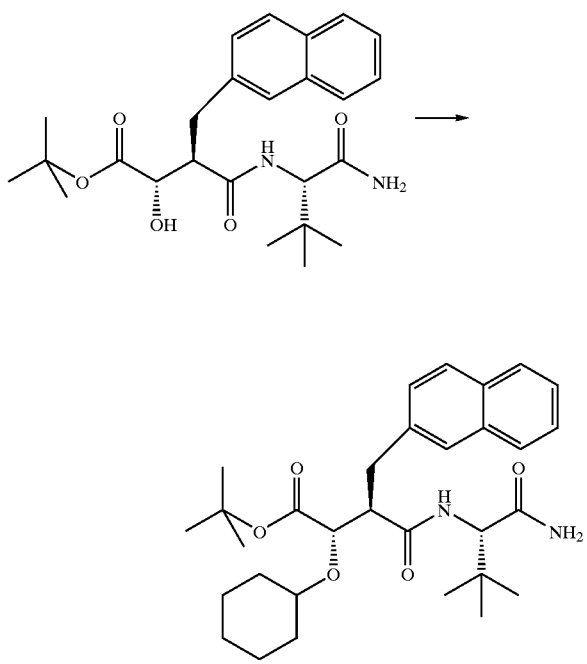

A solution of N-[4-t-Butoxy-3S-(hydroxy)-2R-(2-naphthylmethyl)succinyl]-S-tert-leucinamide (1.0 g, 2.26 mmol) and 3-bromocyclohexene (2.60 ml, 22.6 mmol) in N-methylpyrrolidinone (18 ml) was stirred at 0° C. under argon and lithium bis(trimethylsilyl)amide (2.50 ml of 1M solution in THF, 2.50 mmol) was added dropwise. The mixture was stirred at 0° C. for 10 minutes and then at room temperature for 2.5 hrs. The mixture was diluted with ethyl acetate/1N HCl and the product was extracted into ethyl acetate. The organic extracts were washed with saturated NaHCO$_3$ solution, water (3×) and brine and then dried (Na$_2$SO$_4$) and concentrated. Trituration with hexane to remove excess alkylating agent, followed by chromatography on silica gel (elution with 1:1 ethyl acetate/hexane) gave the product as a foam (378 mg) MS (ES+ve) M+H=523.

This product (340 mg), cyclohexene (1.5 ml) and 10% Pd-C (30 mg) in methanol (15 ml) were refluxed together under argon overnight. After cooling, the mixture was filtered through Celite and concentrated to give a white solid (310 mg).

MS (ES+ve) M+H=525.

$^1$H NMR (CDCl$_3$): 1.09 (9H, s), 1.15–2.0 (10H, m), 1.42 (9H, s), 3.0–3.10 (2H, m), 3.20–3.30 (2H, m), 3.86 (1H, d, J=3.0 Hz), 4.10 (1H, d, J=8.5 Hz), 5.06 (1H, s), 6.55 (1H, s), 7.36–7.50 (4H, m), 7.67 (1H, s), 7.70–7.85 (3H, m).

b) N'-[3S-(Cyclohexyloxy)-4-(N-hydroxyamino)-2R-(2-naphthylmethyl)succinyl]-S-tert-leucinamide

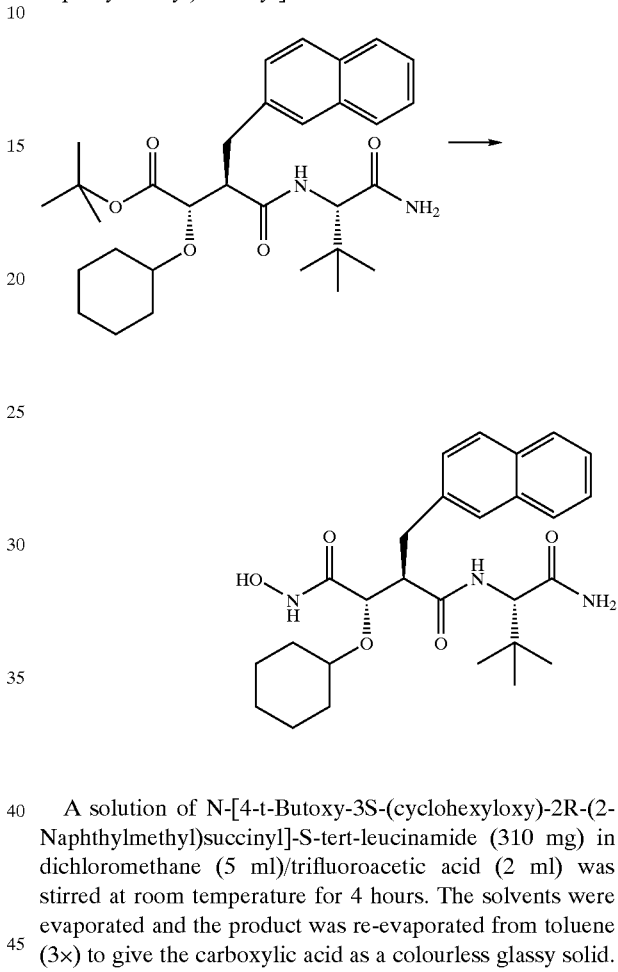

A solution of N-[4-t-Butoxy-3S-(cyclohexyloxy)-2R-(2-Naphthylmethyl)succinyl]-S-tert-leucinamide (310 mg) in dichloromethane (5 ml)/trifluoroacetic acid (2 ml) was stirred at room temperature for 4 hours. The solvents were evaporated and the product was re-evaporated from toluene (3×) to give the carboxylic acid as a colourless glassy solid.

This product in DMF (10 ml) was treated with EDC (0.23 g, 1.18 mmol) and HOAT (0.16 g, 1.18 mmol) followed by a solution of hydroxylamine hydrochloride (0.12 g, 1.77 mmol) and N-methylmorpholine (0.20 ml, 1.77 mmol) in DMF (5 ml). The mixture was stirred at room temperature overnight and then concentrated on the rotary evaporator. The residue was partitioned between ethyl acetate/1N HCl and the product was extracted into ethyl acetate. The extracts were washed with 1N HCl, water and brine and then dried (MgSO$_4$) and evaporated. Trituration with ether gave a white solid (94 mg).

MS (ES–ve) M–H=482

$^1$H NMR (DMSO-d$_6$): 0.90 (9H, s), 1.0–1.95 (10H, m), 2.68 (1H, dd, J=3.9, 13.8 Hz), 2.92 (1H, dd, J=10.6, 13.8 Hz), 3.10–3.20 (2H, m), 3.95 (1H, d, J=9.0 Hz), 4.04 (1H, d, J=9.3 Hz), 6.72 (1H, s), 6.88 (1H, s), 7.27 (1H, d, J=9 Hz), 7.43 (2H, m), 7.60 (2H, m), 7.74 (1H, d, J=8.5 Hz), 7.81 (2H, m), 9.04 (1H, s), 10.86 (1H,s).

EXAMPLE 21

N'-[3S-(Cyclohexyloxy)-4-(N-hydroxyamino)-2R-(2-naphthylmethyl)succinyl]-S-tert-leucine ethylamide

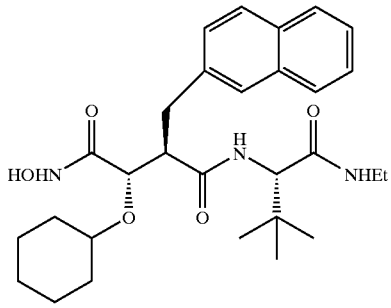

Prepared from N-[4-t-Butoxy-3S-(hydroxy)-2R-(2-naphthylmethyl)succinyl]-S-tert-leucine ethylamide by alkylation, hydrogenation, t-butyl ester cleavage and hydroxamic acid formation analogously to Example 20 to give N'-[3S-(Cyclohexyloxy)-4-(N-hydroxyamino)-2R-(2-naphthylmethyl)succinyl]-S-tert-leucine ethylamide.

MS (ES–ve) M–H=510

$^1$H NMR (DMSO-$d_6$): 0.65 (3H, t, J=7.2 Hz), 0.85 (9H, s), 1.0–1.25 (5H, m), 1.47 (1H, m), 1.65 (2H, m), 1.75 (1H, m), 1.85 (1H, m), 2.45–2.69 (3H, m), 2.83 (1H, m), 3.20 (2H, m), 3.96 (1H, d, J=9.2 Hz), 3.98 (1H, d, J=9.1 Hz), 7.12 (1H, m), 7.26 (1H, dd, J=1.1, 8.3 Hz), 7.43 (2H, m), 7.53 (1H, d, J=10 Hz), 7.58 (1H, s), 7.72–7.85 (3H, m), 9.07 (1H, s), 10.85 (1H, s).

EXAMPLE 22

N'-[3S-(Ethoxy)-4-(N-hydroxyamino)-2R-(2-naphthylmethyl)succinyl]-S-tert-leucine methylamide

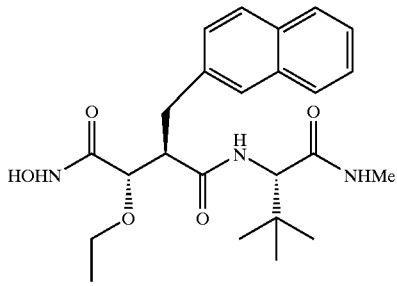

Prepared analogously to Example 1) a)+b)+c) from N-4-t-Butoxy-3S-(hydroxy)-2R-(2-naphthylmethyl)succinyl]-S-tert-leucine methylamide by alkylation with iodoethane instead of allyl bromide.

MS (ES–ve) M–H=442

$^1$H NMR (DMSO-$d_6$): 0.84 (9H, s), 1.04 (3H, t, J=7.0 Hz), 2.07 (3H, d, J=4.5 Hz), 2.64 (1H, dd, J=3.8, 13.6 Hz), 2.83 (1H, m), 3.20–3.27 (2H, m), 3.44 (1H, m), 3.77 (1H, d, J=9.6 Hz), 4.05 (1H, d, J=9.8 Hz), 7.06 (1H, m), 7.24 (1H, dd, J=1.5, 8.4 Hz), 7.44 (2H, m), 7.56 (1H, s), 7.59 (1H, d, J=10 Hz), 7.72–7.85 (3H, m), 9.08 (1H, s), 10.92 (1H, s).

EXAMPLE 23

N'-[4-(N-Hydroxyamino)-2R-(2-Naphthylmethyl)-3S-((3-phenyl)propyloxy)succinyl]-S-tert-leucinamide

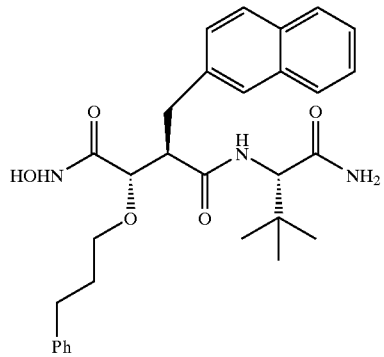

Prepared analogously to Example 1a)+b)+c) from N-4-t-Butoxy-3S-(hydroxy)-2R-(2-naphthylmethyl)succinyl]-S-tert-leucinamide by alkylation with cinnamyl bromide, followed by reduction, deprotection and hydroxamic acid formation.

MS (ES+ve) M+H=520, MS (ES–ve) M–H=518

$^1$H NMR (DMSO-$d_6$): 0.9 (9H, s), 1.70–1.80 (2H, m), 2.50–2.70 (3H, m), 2.85–2.95 (1H, m), 3.18–3.3 (2H, m), 3.35–3.45 (1H, m), 3.75 (1H, d, J=9.4 Hz), 4.10 (1H, d, J=9.5 Hz), 6.75 (1H, s), 6.95 (1H, s), 7.10–7.20 (3H, m), 7.25–7.30 (3H, m), 7.35–7.45 (2H, m), 7.60 (1H, s), 7.68–7.85 (4H, m), 9.10 (1H, s), 10.9 (1H, s).

EXAMPLE 24

N'-[4-(N-Hydroxyamino)-2R-(2-naphthylmethyl)-3S-(thiazol-2-ylmethoxy)succinyl]-S-tert-leucinamide

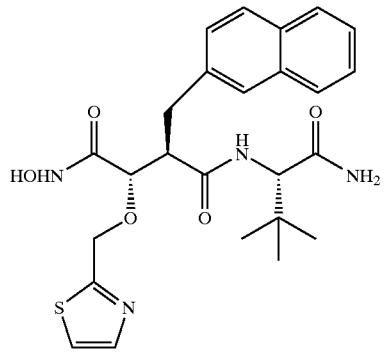

Prepared analogously to Example 1a)+b)+c) from N-[4-t-Butoxy-3S-(hydroxy)-2R-(2-naphthylmethyl)succinyl]-S-tert-leucinamide by alkylation with 2-bromomethylthiazole instead of allyl bromide.

MS (ES+ve) M+H=499, MS (ES–ve) M–H=497

$^1$H NMR (DMSO-$d_6$): 0.80 (9H, s), 2.65–2.70 (1H, m), 2.88–2.97 (1H, m), 3.30–3.50 (1H, m), 4.05 (1H, d, J=9.6 Hz), 4.10 (1H, d, J=9.3 Hz), 4.65 (1H, d, J=12.9 Hz), 4.75 (1H, d, J=12.94 Hz), 6.70 (1H, s), 6.95 (1H, s), 7.25 (1H, d, J=8.6 Hz), 7.40–7.50 (2H,m), 7.60 (1H, s) 7.70–7.80 (4H, m), 7.80–7.88 (2H, m), 9.20 (1H, s), 11.05 (1H, s).

EXAMPLE 25

N'-[3S-(Cyclohexylcarbonyloxy)-4-(N-hydroxyamino)-2R-(2-naphthylmethyl)succinyl]-S-tert-leucinamide

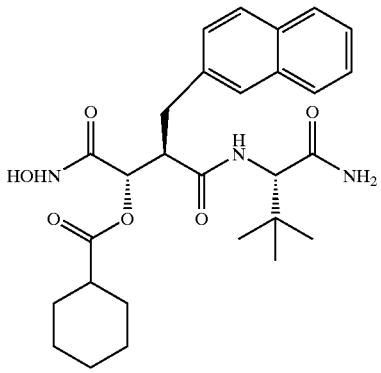

Prepared analogously to Example 1a)+b)+c) from N-[4-t-Butoxy-3S-(hydroxy)-2R-(2-naphthylmethyl)succinyl]-S-tert-leucinamide by acylation with cyclohexoyl chloride instead of alkylation with allyl bromide (see example 27).

MS (ES+ve) M+H=512

$^1$H NMR (DMSO-$d_6$): 0.88 (9H, s), 1.10–1.38 (5H, m), 1.50–1.88 (5H, m), 2.22 (1H, m), 2.80 (1H, dd, J=4,14 Hz), 2.97 (1H, dd, J=10,14 Hz), 3.41 (1H, m), 4.09 (1H, d, J=9 Hz), 4.90 (1H, d, J=10 Hz), 6.76 (1H, s), 7.01 (1H, s), 7.28 (1H, d), 7.47 (2H, m), 7.61 (1H, s), 7.74 (1H, d, J=9 Hz), 7.82 (3H, m), 9.07 (1H, s), 11.01 (1H, s).

EXAMPLE 26

N'-[3S-(t-Butylcarbonyloxy)-4-(N-hydroxyamino)-2R-(2-naphthylmethyl)succinyl]-S-tert-leucinamide

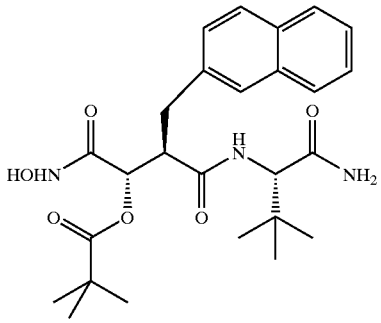

Prepared analogously to Example 1a)+b)+c) from N-[4-t-Butoxy-3S-(hydroxy)-2R-(2-naphthylmethyl)succinyl]-S-tert-leucinamide by acylation with pivaloyl chloride instead of alkylation with allyl bromide (see example 27).

MS (ES+ve) M+H=486

$^1$H NMR (DMSO-$d_6$): 0.87 (9H, s), 1.11 (9H, s), 2.84 (1H, dd, J=5,14 Hz), 2.93 (1H, dd, J=9,14 Hz), 4.03 (1H, d, J=9 Hz), 4.95 (1H, d, 9 Hz), 6.73 (1H, s), 6.99 (1H, s), 7.31 (1H, d, J=8 Hz), 7.44 (2H, m), 7.64 (1H, s), 7.75 (1H, d, J=9 Hz), 7.81 (3H, m), 9.05 (1H, s), 11.00 (1H, s).

EXAMPLE 27

N'-[3S-benzoyloxy-4-(N-hydroxyamino)-2R-(2-naphthylmethyl)succinyl]-S-tert-leucinamide a) N-[3S-benzoyloxy-4-t-butoxy-2R-(2-naphthylmethyl)succinyl]-S-tert-leucinamide

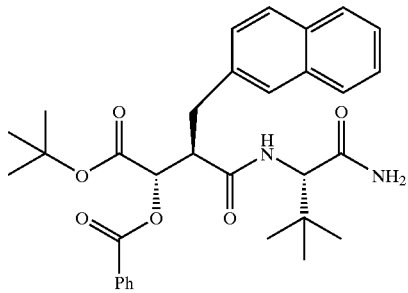

To a solution of N-[4-t-Butoxy-3S-hydroxy-2R-(2-naphthylmethyl)succinyl]-S-tert-leucinamide (0.3 g, 0.678 mmol) in DME (5 mL) was added NaH (60% suspension in mineral oil, 0.03 g, 0.75 mmol) followed after 30 sec. by benzoyl chloride (0.087 mL, 0.075 mmol). The mixture was stirred for 1 hr at room temp and then poured into 0.5 M HCl and extracted (2×) with EtOAc. The extracts were washed with Na HCO$_3$ soln, water and brine; dried (MgSO$_4$) and evaporated to a foam which crystallised on addition of ether. The product was obtained as a white crystalline solid, 0.33 g (89%).

MS (ES+ve) M+H=547, (M+Na)=569

$^1$H NMR (DMSO-$d_6$): 0.85 (9H, s), 1.40 (9H, s), 3.00 (1H, m), 3.18 (1H, m), 3.65 (1H, m), 4.20 (1H, d, J=8 Hz), 5.04 (1H, d, J=7 Hz), 6.89 (1H, br. s), 7.34 (1H, br. s), 7.38–7.53 (5H, m), 7.67–7.72 (2H, m), 7.78–7.88 (3H, m), 7.98 (2H, d, J=8 Hz), 8.06 (1H, d, J=8 Hz).

b) N'-[3S-Benzoyloxy-4-(N-hydroxyamino)-2R-(2-naphthylmethyl)succinyl]-S-tert-leucinamide

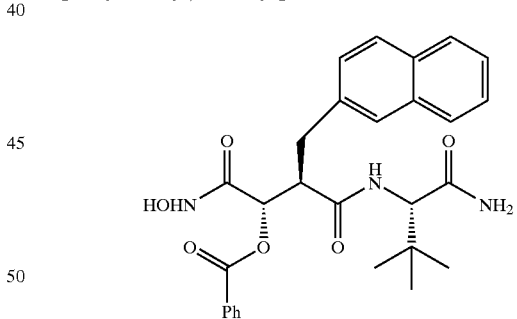

Prepared from N-[3S-Benzoyloxy-4-t-butoxy-2R-(2-naphthylmethyl)succinyl]-S-tert-leucinamide analogously to example 1 b)+c).

MS (ES−ve) M−H=504, MS (ES+ve) M+H=506, M+Na=528

$^1$H NMR (DMSO-$d_6$): 0.73 (9H, s), 2.73–2.89 (1H, m), 3.00–3.10 (1H, m), 3.58–3.67 (1H, m), 4.10 (1H, d, J=9 Hz), 5.21 (1H, d, J=10 Hz), 6.73 (1H, br s), 7.10 (1H, br s), 7.31 (1H, d, J=9 Hz), 7.43–7.52 (4H, m), 7.65 (2H, m), 7.74–7.85 (3H, m), 8.04 (3H, m), 9.15 (1H, s), 11.22 (1H, s).

EXAMPLE 28

N'-[3S-(Ethoxy)-4-(N-hydroxyamino)-2R-(2-quinolinylmethyl)succinyl]-S-tert-leucine methylamide

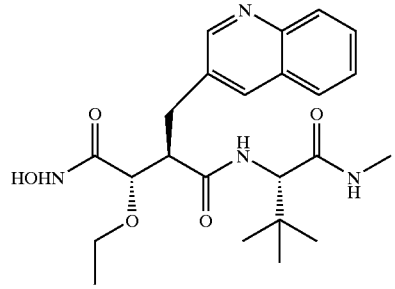

A solution of N'-[3S-(Ethoxy)-4-(N-hydroxy)-2R-(2-quinolinylmethyl)succinyl]-S-tert-leucine methylamide hydrochloride (prepared analogously to example 1 b from 3-(3-quinoline)propionic acid, 0.19 g, 0.42 mmol) in anhydrous DMF (5 ml) was treated sequentially with HOAT (0.11 g, 0.84 mmol) and EDC (0.16 g, 0.84 mmol), and the solution was stirred at room temperature for 0.25 h. Hydroxylamine hydrochloride (0.09 g, 1.26 mmol) and N-methylmorpholine (0.18 ml, 1.35 mmol) were then added and the solution was stirred for 3 h at room temperature. The solution was evaporated to dryness and the residue was partitioned between ethyl acetate and water. The phases were separated and the organic phase was washed with further water and sat$^d$. sodium bicarbonate solution and dried with brine and over magnesium sulfate. The organic phase was then evaporated and dried in the drying pistol at 50° C. for 3 hours to afford the title compound as a white solid (0.01 g, 5%).

MS (ES+ve) M+H=445

$^1$H NMR (DMSO-d$_6$): 0.82 (9H, s), 1.04 (3H, t, J=6.9 Hz), 2.06 (3H, d, J=4.5), 2.72 (1H, m), 2.75 (1H, m), 3.26 (1H, m), 3.31 (1H, m), 3.44 (1H, m), 3.80 (1H, d, J=9.7 Hz), 4.05 (1H, d, J=9.6 Hz), 7.22 (1H, q, J=5.6 Hz), 7.53 (1H, t, J=6.0 Hz), 7.66 (1H, d, J=6.6 Hz), 7.70 (1H, t, J=7.3 Hz), 7.84 (1H, d, J=6.7 Hz), 7.94 (1H, d, 7.9 Hz), 7.97 (1H, s), 8.60 (1H, d, H=2 Hz), 9.11 (1H, s), 10.96 (1H, s).

EXAMPLE 29

N'-[4-(N-Hydroxyamino)-3S-methoxy -2R-(2-naphthylmethyl)succinyl]-S-tert-leucine methylamide

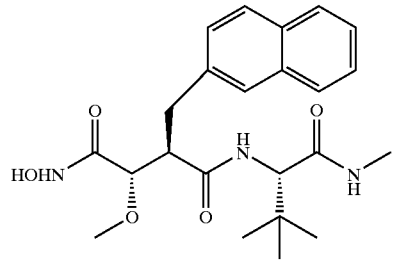

Prepared analogously to example 1)a)+b)+c) from N-4-t-Butoxy-3S-(hydroxy)-2R-(2-naphthylmethyl)succinyl]-S-tert-leucine methylamide by alkylation with iodomethane instead of allyl bromide.

MS (ES+ve) M+H=430

$^1$H NMR (DMSO-d$_6$): 0.83 (9H, s), 2.10 (3H, d, J=4.5 Hz), 2.63 (1H, dd, J=4.14 Hz), 2.84 (1H, dd, J=11.14 Hz), 3.17 (3H, s), 3.20 (1H, m), 3.67 (1H, d, J=10 Hz), 4.08 (1H, d, J=10 Hz), 7.14 (1H, q, J=4.5 Hz), 7.25 (1H, m), 7.43 (2H, m), 7.56 (1H, s), 7.61 (1H, d J=10 Hz), 7.80 (3H, m), 9.09 (1H, s), 10.94 (1H, s).

EXAMPLE 30

N'-[4-(N-Hydroxyamino)-2R-(2-naphthylmethyl) succinyl-3S-propanoyloxy]-S-tert-leucine methylamide

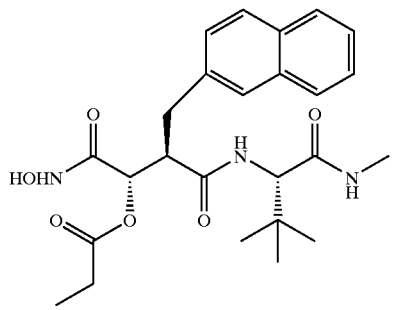

Prepared analogously to example 27 from N-4-t-Butoxy-3S-(hydroxy)-2R-(2-naphthylmethyl)succinyl]-S-tert-leucine methylamide by acylation with propanoyl chloride instead of benzoyl chloride.

MS (APCI+ve) M+Na=494

$^1$H NMR (DMSO-d$_6$): 0.82 (9H, s), 0.99 (3H, t, J=7.5 Hz), 2.07 (3H, d, J=4.5 Hz), 2.22 (2H, m), 2.78 (1H, dd, J=4, 13.5 Hz), 2.88 (1H, dd, J=11, 14 Hz), 3.42 (1H, m), 4.03 (1H, d, J=9 Hz), 4.96 (1H, d, J=10 Hz), 7.16 (1H, q, J=4.5 Hz), 7.25 (1H, m), 7.44 (2H, m), 7.57 (1H, s), 7.80 (4H, m), 9.09 (1H, s), 11.07 (1H, s).

EXAMPLE 31

N'-[3S-(Ethoxy)-4-(N-hydroxyamino)-2R-(2-naphthylmethyl)succinyl]-S-tert-leucine ethylamide

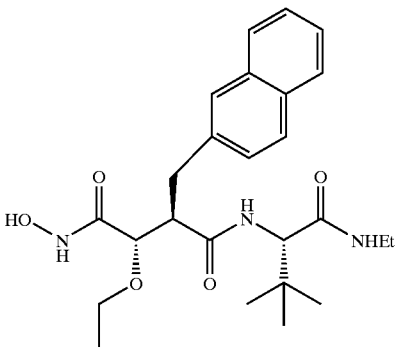

Prepared analogously to example 1) from N-[4-t-Butoxy-3S-(hydroxy)-2R-(2-naphthylmethyl)succinyl]-S-tert-leucine ethylamide by alkylation with iodoethane instead of allyl bromide, then cleavage of the tert-butyl ester and hydroxamic acid formation.

MS (ES−ve) M−H=456

$^1$H NMR (DMSO-d$_6$): 0.67 (3H, t, J=7.0 Hz), 0.84 (9H, s), 1.05 (3H, t, J=7.0 Hz), 2.55 (1H, m), 2.65 (2H, m), 2.82

(1H, t, J=11.0 Hz), 3.17–3.30 (2H, m, partially obscured), 3.44 (1H, m), 3.77 (1H, d, J=9.5 Hz), 4.05 (1H, d, J=9.5 Hz), 7.23–7.25 (2H, m), 7.38–7.48 (2H, m), 7.56–7.59 (2H, m), 7.72 (1H, d, J=8.5 Hz), 7.76–7.83 (2H, m), 9.08 (1H, s), 10.93 (1H, s).

EXAMPLE 32

N'-[4-(N-Hydroxyamino)-2R-(2-naphthylmethyl)-3S-(2-methylpropoxy)succinyl]-S-tert-leucine methylamide

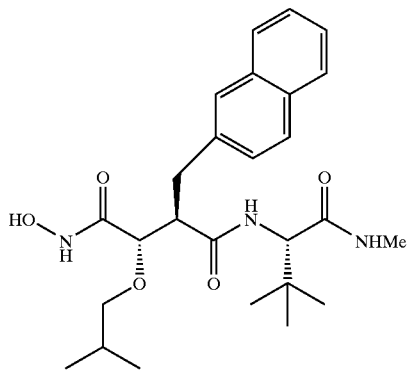

Prepared analogously to example 1) from N-[4-t-Butoxy-3S-(hydroxy)-2R-(2-naphthylmethyl)succinyl]-S-tert-leucine methylamide by alkylation with methallyl bromide, hydrogenation, tert butyl ester cleavage and hydroxamic acid formation.

MS (ES–ve) M–H=470

$^1$H NMR (DMSO-d$_6$): 0.79–0.83 (6H, m), 0.83 (9H, s), 1.72 (1H, m), 2.04 (3H, d, J=4.5 Hz), 2.65 (1H, dd, J=4.0, 13.5 Hz), 2.82 (1H, dd, J=11.0, 13.5 Hz), 3.04 (1H, dd, 6.5, 9.0 Hz), 3.12 (1H, dd, J=7.5, 9.0 Hz), 3.26 (1H, m), 3.78 (1H, d, J=9.5 Hz), 4.00 (1H, d, J=9.3 Hz), 6.99 (1H, m), 7.27 (1H, dd, J=1.5, 8.5 Hz), 7.44 (2H, m), 7.55 (1H, d, J=10.5 Hz), 7.57 (1H, s), 7.74 (1H, d, J=8.5 Hz), 7.77–7.85 (2H, m), 9.09 (1H, s), 10.88 (1H, s).

EXAMPLE 33

N'-[4-(N-Hydroxyamino)-2R-(2-naphthylmethyl)-3S-propoxysuccinyl]-S-tert-leucine ethylamide

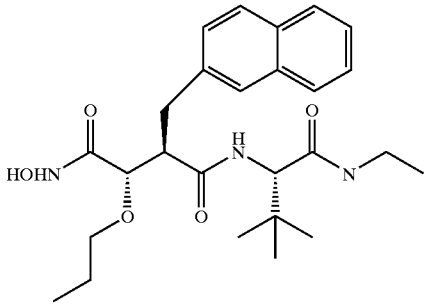

N'-[4-Hydroxy-2R-(2-naphthylmethyl)-3S-propoxysuccinyl]-S-tert-leucine ethylamide (0.17 g, 0.372 mmol) (prepared analogously to example 1) from N-[4-t-Butoxy-3S-(hydroxy)-2R-(2-naphthylmethyl)succinyl]-S-tert-leucine ethylamide by alkylation with allyl bromide, hydrogenation, then cleavage of the tert-butyl ester) was treated with HOAT (0.1 g 0.735 mmol), DEC (0.142 g, 0.74 mmol), hydroxylamine hydrochloride (0.078 g, 1.12 mmol) and N-methylmorpholine (0.123 mL, 1.12 mmol), in DMF (4.3 mL), in the standard manner. Normal work-up procedure gave the product as a white solid, 0.1 g, (57%).

MS (ES+ve) M+H=472, M+Na=494.

$^1$H NMR (DMSO-d$_6$): 0.66 (3H, t, J=7 Hz), 0.82 (3H, t, J=7.5 Hz), 0.84 (9H, s), 1.45 (2H, sextet, J=7 Hz), 2.53 (1H, m), 2.65 (2H, m), 2.84 (1H, m), 3.20 (2H, m) ca. 3.30 (1H, m, partially obs.), 3.77 (1H, d, J=9.5 Hz), 4.03 (1H, d, J=9.5 Hz), 7.21 (1H, br. t, J≈4 Hz), 7.25 (1H, dd, J=8.5, 1.5 Hz), 7.43 (2H,m), 7.56 (1H, d, J=8.5 Hz), 7.57 (1H, s), 7.72 (1H, d, J=8.5 Hz), 7.75–7.83 (2H, m), 9.10 (1H, s), 10.89 (1H, br. s).

EXAMPLE 34

N'-[3S-tert-Butoxy-4-(N-hydroxyamino)-2R-(2-naphthylmethyl)succinyl]-S-tert-leucine methylamide a) N'-[4-(N-Benzyloxyamino)-3S-hydroxy-2R-(2-naphthylmethyl)succinyl]-S-tert-leucine methylamide

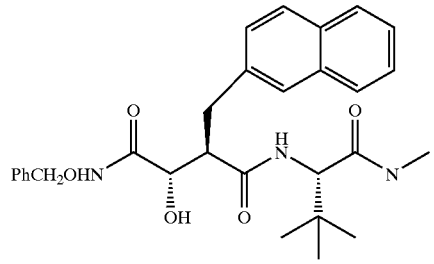

N'-[3S,4-Dihydroxy-2R-(2-naphthylmethyl)succinyl]-S-tert-leucine methylamide (1.5 g, 3.75 mmol) in DMF (25 mL), was treated with HOBT (1.15 g, 7.51 mmol), and DEC (1.44 g, 7.51 mmol). After stirring the mixture for 20 min., O-benzylhydroxylamine (0.92 mL), was added. The reaction was stirred at room temp. for 6 hr., and the DMF was then removed in vacuo. To the residue was added NaHCO$_3$ soln. and the mixture was extracted (2×) with EtOAc. The combined extracts were washed with NaHCO$_3$ soln., water and brine; dried (MgSO$_4$) and evaporated to a gum which was purified by column chromatography on silica (hexane/EtOAc; 0–100%), giving the product as a white foam, 0.73 g (39%).

MS (ES+ve) M+H=506, M+Na=528.

$^1$H NMR (DMSO-d$_6$): 0.85 (9H, s), 2.29 (3H, d, J=4.5 Hz), 2.74 (1H, dd, J=13.5, 6 Hz), 2.93 (1H, dd, J=13.5, 9.5 Hz), 3.13(1H, m), 3.86 (1H, t, J=7.5 Hz), 4.11 (1H, d, J=9.5 Hz), 4.80 (2H, s), 5.71 (1H, d, J=7.5 Hz), 7.29–7.48 (8H, m), 7.53–7.58 (2H, m), 7.61 (1H, s), 7.76–7.80 (2H, m), 7.85 (1H, d, J=7 Hz), 11.27 (1H, s).

b) N'-[4-(N-Benzyloxyamino)-3S-tert-butoxy-2R-(2-naphthylmethyl)succinyl]-S-tert-leucine methylamide

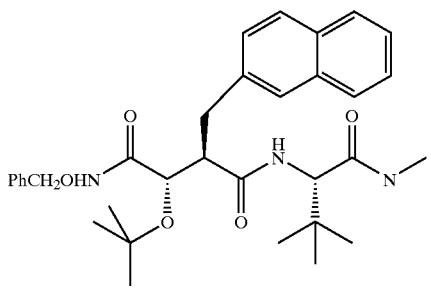

N'-[4-(N-Benzyloxyamino)-3S-hydroxy-2R-(2-naphthylmethyl)succinyl]-S-tert-leucine methylamide (0.69 g, 1.36 mmol) was dissolved in DCM (30 mL) and the solution cooled in an ice-salt bath. Into the cooled solution was condensed isobutylene (ca. 30 mL) by means of a cardice-acetone condenser. Conc. $H_2SO_4$ (12 drops) was added and the mixture was allowed to stir while warming to room temp overnight. The mixture was diluted with 3–4 times its volume of EtOAc and washed with $NaHCO_3$, water and brine; dried ($MgSO_4$) and evaporated to a gum which was purified by chromatography on silica (hexane/EtOAc; 0–100%). The product was obtained as a white foam 0.31 g (41%). MS (ES+ve) M+H=562, M+Na=584.

$^1$H NMR (DMSO-$d_6$): 0.84 (9H, s), 1.10 (9H, s), 1.98 (3H, d, J=4.5 Hz), 2.65 (1H, dd, J=11, 4 Hz), 2.76 (1H, dd, J=11, 11 Hz), 3.08 (1H, m), 3.94 (1H, d, J=9 Hz), 4.02 (1H, d, J=9 Hz), 4.81 (d, J=13.5 Hz) and 4.86 (d, J=13.5 Hz) (Abq), 6.93 (1H, br. q, J=4.5 Hz), 7.22 (1H, d, J=8.5 Hz), 7.30–7.47 (8H, m), 7.53 (1H, s), 7.73 (1H, d, J=8.5 Hz), 7.78 (1H, d, J=8 Hz), 7.84 (1H, d, J=8 Hz), 11.35 (1H, s).

c) N'-[3S-tert-Butoxy-4-(N-hydroxyamino)-2R-(2-naphthylmethyl)succinyl-S-tert-leucine methylamide

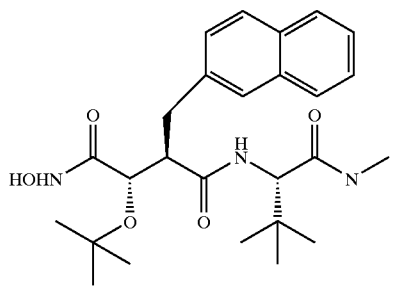

N'-[4-(N-benzyloxyamino)-3S-tert-butoxy-2R-(2-naphthylmethyl)succinyl]-S-tert-leucine methylamide (0.305 g, 0.54 mmol) was hydrogenated for 4 hr. at room temperature and atmospheric pressure in the presence of Pd-BaSO$_4$ (0.31 g). The catalyst was removed by filtration and the filtrate evaporated. The residue was triturated with ether to give the product as an off-white solid, 0.152 g (59%).

MS (ES+ve) M+H=472, M+Na=494.

$^1$H NMR (DMSO-$d_6$): 0.84 (9H, s), 1.11 (9H, s), 1.93 (3H, d, J=4.5 Hz), 2.70 (1H, dd, J≈11, 4 Hz), 2.80 (1H, dd, J≈11, 11 Hz), 3.11 (1H, m), 3.93 (1H, d, J=9 Hz), 4.02 (1H, d, J=9 Hz), 6.84 (1H, br, q, J=4.5 Hz), 7.25 (1H, d, J=8.5 Hz), 7.40–7.46 (3H, m), 7.56 (1H, s), 7.74 (1H, d, J=8.5 Hz), 7.78 (1H, d, J≈8 Hz), 7.84 (1H, d, J≈8 Hz), 8.96 (1H, s), 10.74 (1H, br. s).

EXAMPLE 35

N'-[3S-tert-Butoxy-4-(N-hydroxyamino)-2R-(2-naphthylmethyl)succinyl]-S-tert-leucine ethylamide

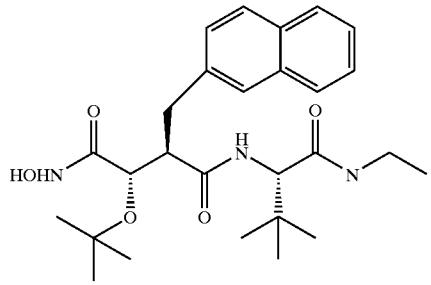

N'-[4-(N-Benzyloxyamino)-3S-tert-butoxy-2R-(2-naphthylmethyl)succinyl]-S-tert-leucine ethylamide was prepared and hydrogenolysed as described in example 34 to give the product as a slightly greyish solid, 0.224 g (88%).

MS (ES+ve) M+H=486, M+Na=508.

$^1$H NMR (DMSO-$d_6$): 0.63 (3H, t, J=7 Hz), 0.85 (9H, s), 1.12 (9H, s), 2.39 (1H, m), 2.55 (1H, m), 2.70 (1H, dd, J≈11, 4 Hz), 2.81 (1H, dd, J≈11, 11 Hz), 3.11 (1H, m), 3.92 (1H, d, J=9 Hz), 4.02 (1H, d, J=9 Hz), 7.05 (1H, br. t, J=4.5 Hz), 7.26 (1H, dd, J=8.5, 1.5 Hz), 7.40–7.46 (3H, m), 7.57 (1H, s), 7.73 (1H, d, J=8.5 Hz), 7.78 (H, d, J≈8 Hz), 7.82 (1H, d, J≈8 Hz), 8.95 (1H, s), 10.73 (1H, br. s).

EXAMPLE 36

N''-[4-(N-Hydroxyamino)-3S-(2-oxy-N-(N',N'-2-dimethylaminoethyl)acetamido)-2R-(2-naphthylmethyl)succinyl]-S-tert-leucine methylamide

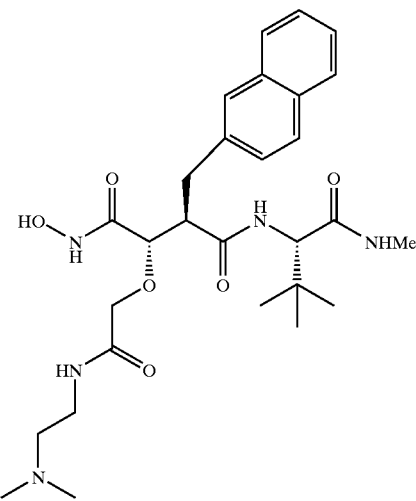

a) N'-[4-t-Butoxy-3S-(2-oxybenzylacetate)-2R-(2-naphthylmethyl)succinyl]-S-tert-leucine methylamide

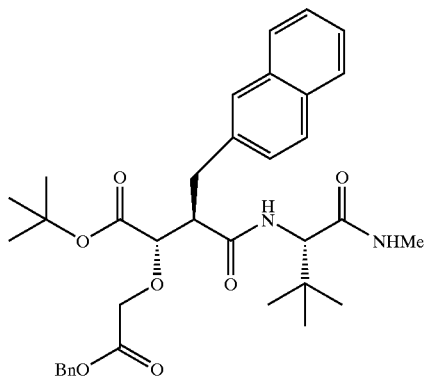

The title compound was prepared by alkylating N-4-t-Butoxy-3S-(hydroxy)-2R-(2-naphthylmethyl)succinyl-S-tert-leucine methylamide with 2-bromo benzylacetate in acetonitrile (c.f. example 1a).

MS (ES+ve) M+H=605, M+Na=629

$^1$H NMR (CDCl$_3$): 1.02 (9H,s), 1.42 (9H,s), 2.59 (3H, d, J=5 Hz), 3.07–3.30 (3H, m), 3.77 (1H, d, J=3.5 Hz), 3.98 (1H, d, J=16 Hz), 4.12 (1H, d, J=9 Hz), 4.35 (1H, d, J=16 Hz), 5.26 (2H, s), 6.23 (1H, q, J=4 Hz), 7.04 (1H, d, J=9 Hz), 7.29–7.48 (8H, m), 7.64 (1H, s), 7.68–7.83 (3H,m).

b) N'-[4-t-Butoxy-3S-(2-oxyacetic acid)-2R-(2-naphthylmethyl)succinyl]-S-tert-leucine methylamide

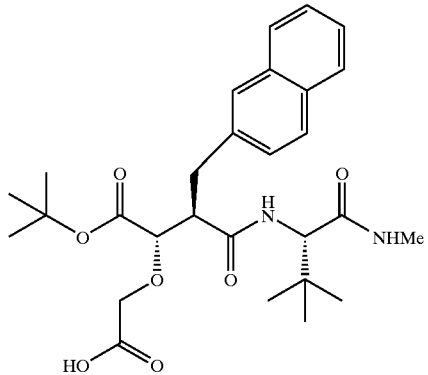

N'-[4-t-Butoxy-3S-(2-oxybenzylacetate)-2R-(2-naphthylmethyl)succinyl]-S-tert-leucine methylamide (2.71 g, 4.49 mmol) in methanol (70 ml) was hydrogenolyzed with Pd/BaSO$_4$ (0.51 g) at room temperature and atmospheric pressure for 4 hours. The solution was filtered through Celite and concentrated to give 2.30 g of a white solid (100%).

MS (ES+ve) M+H=515

MS (ES−ve) M−H=513

$^1$H NMR (DMSO-d$_6$): 0.84 (9H, s), 1.44 (9H, s), 2.25 (3H, d, J=7.2 Hz), 2.75–3.03 (2H, m), 3.27 (1H, m), 3.96–4.13 (4H, m), 7.30 (1H, dd, J=1.4, 8.4 Hz), 7.44 (3H, m), 7.74 (1H, s), 7.74–7.88 (4H, m), 12.65 (1H, s).

c) N"-[4-Butoxy-3S-(2-oxy-N-(N',N'-2-dimethylaminoethyl)acetamido)-2R-(2-naphthylmethyl)succinyl]-S-tert-leucine methylamide

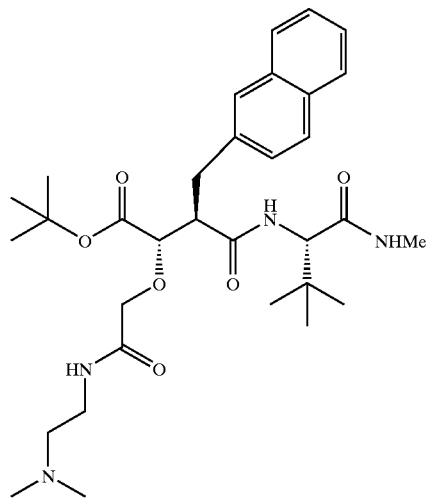

N'-[4-t-Butoxy-3S-(2-oxyacetic acid)-2R-(2-naphthylmethyl)succinyl]-S-tert-leucine methylamide (0.6 g, 1.16 mmol), EDC (0.25 g, 1.28 mmol) and HOAT (0.17 g, 1.28 mmol) were stirred in DMF (11 ml) under argon at room temperature for 10 minutes and then 2-(dimethylamino)ethylamine (0.15 ml, 1.40 mmol) was added. The reaction was stirred overnight under argon at room temperature. The DMF was evaporated and the residue partitioned between ethyl acetate and water. The organic layer was washed with water (×2), sodium bicarbonate solution (×2), and brine, then dried (Na$_2$SO$_4$) and evaporated. Chromatography on silica gel (dichloromethane-methanol) gave the title compound (62%).

MS (ES+ve) M+H=585

$^1$H NMR (DMSO-d$_6$): 0.83 (9H, s), 1.45 (9H, s), 2.18 (6H, s), 2.30 (3H, d, J=4.5 Hz), 2.36 (2H, t, J=6.8 Hz), 2.82–3.05 (2H, m), 3.19–3.40 (4H, m), 3.77 (1H, d, J=15.5 Hz), 3.94 (1H, d, J=17.0 Hz), 4.15 (1H, d, J=9.5 Hz), 7.29 (1H, dd, J=1.5, 8.5 Hz), 7.46 (2H, m), 7.59 (1H, s), 7.67 (1H, m), 7.75–7.86 (5H, m).

d) N"-[4-(N-Hydroxyamino)-3S-(2-oxy-N-(N',N'-2-dimethylaminoethyl)acetamido)-2R-(2-naphthylmethyl)succinyl]-S-tert-leucine methylamide

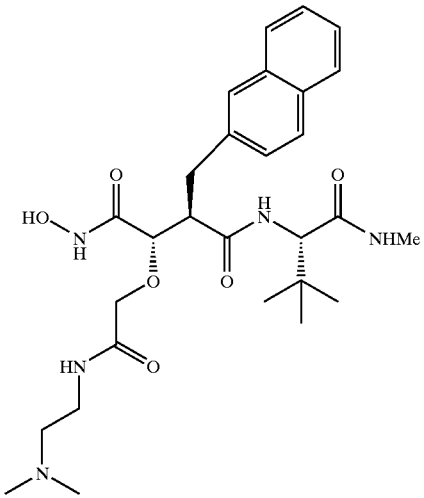

Cleavage of the tert-butyl ester and formation of the hydroxamic acid by coupling of the carboxylic acid with O-benzylhydroxylamine followed by hydrogenolysis with Pd-BaSO$_4$ gave the title compound.

MS (ES+ve) M+Na=556, M+H=544

MS (ES−ve) M−H=542

$^1$H NMR (DMSO-d$_6$): 0.81 (9H, s), 2.20 (3H, d, J=4.5 Hz), 2.74 (1H, dd, J=3.7, 13.6 Hz), 2.82 (3H, s), 2.83 (3H, s), 2.89 (1H, d, J=13.7 Hz), 3.14 (2H, d, J=5.2 Hz), 3.33 (1H, td, J=4.0, 10.2 Hz), 3.43 (2H, m), 3.82 (1H, d, J=15.5 Hz), 3.93 (1H, d, J=15.5 Hz), 3.97 (1H, d, J=9.6 Hz), 4.11 (1H, d, J=9.5 Hz), 7.22 (1H, dd, J=1.2, 8.4 Hz), 7.45 (3H, m), 7.54 (1H, s), 7.74 (1H, d, J=8.5 Hz), 7.77 (1H, d, J=7.5 Hz), 7.84 (2H, d, J=8.7 Hz), 8.00 (1H, t, J=5.7 Hz), 9.29 (1H, s) 11.09 (1H, s).

EXAMPLE 37

N'-[4-(N-Hydroxyamino)-3S-(2-oxy-N-(2'-acetoxyethyl)acetamido)-2R-(2-naphthylmethyl)succinyl]-S-tert-leucine methylamide

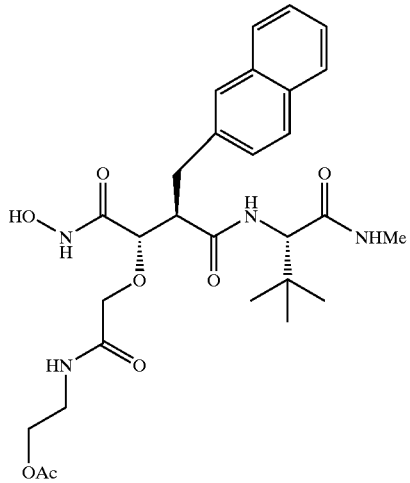

a) N'-[4-Butoxy-3S-(2-oxy-N-(2-hydroxyethyl)acetamido)-2R-(2-naphthylmethyl)succinyl]-S-tert-leucine methylamide

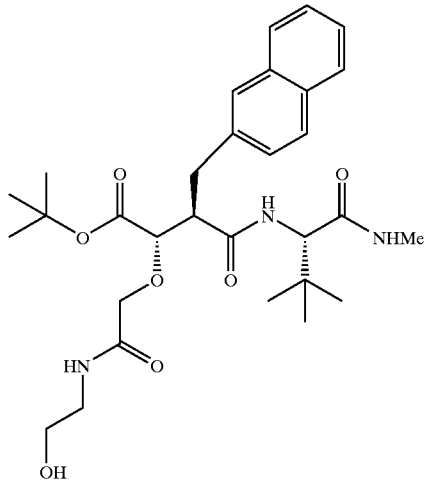

Reaction of 2-aminoethanol with N'-[4-t-Butoxy-3S-(2-oxyacetic acid)-2R-(2-naphthylmethyl)succinyl]-S-tert-leucine methylamide as for example 36c gave the title compound.

MS (ES+ve) M+Na=580, M+H=558

$^1$H NMR (DMSO-d$_6$): 0.83 (9H, s), 1.45 (9H, s), 2.29 (3H, d, J=4.5 Hz), 2.85 (1H, m), 2.95 (1H, m), 3.20 (2H, m), 3.32 (1H, m), 3.42 (2H, m), 3.78 (1H, d, J=15.3 Hz), 3.94 (1H, d, J=15.3 Hz), 3.98 (1H, d, J=8.1 Hz), 4.15 (1H, d, J=9.60 Hz), 4.68 (1H, t, J=5.6 Hz), 7.28 (1H, dd, J=1.6, 8.4 Hz), 7.45 (2H, m), 7.59 (1H, s), 7.68 (2H, m), 7.77 (2H, m).

b) N'-[4-Butoxy-3S-(2-oxy-N-(2-acetoxyethyl)acetamido)-2R-(2-naphthylmethyl)succinyl]-S-tert-leucine methylamide

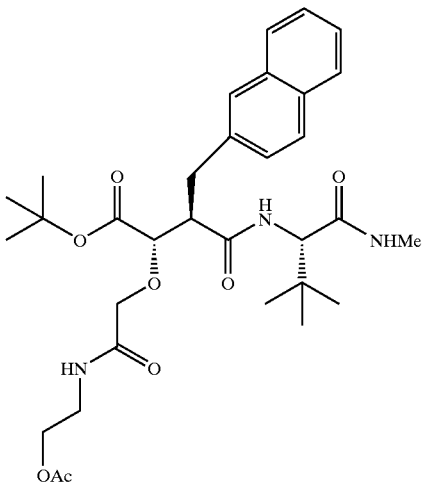

To a solution of N'-[4-Butoxy-3S-(2-oxy-N-(2-hydroxyethyl)acetamido)-2R-(2-naphthylmethyl)succinyl]-S-tert-leucine methylamide (0.8 g, 1.05 mmol), pyridine (0.25 ml, 3.15 mmol) and DMAP (few crystals) in dichloromethane (8.5 ml) at 0° C. was added acetic anhydride. The mixture was stirred at 0° C. for 1 hour and was then diluted with ethyl acetate and washed with dilute HCl (×2), NaHCO$_3$ solution and brine, dried (Na$_2$SO$_4$) and concentrated. Chromatography on silica gel (hexane/ethyl acetate—1:4) gave 0.56 g of product (88%).

MS (ES+ve), M+H=600

$^1$H NMR (DMSO-d$_6$): 0.82 (9H, s), 1.45 (9H, s), 1.99 (3H, s), 2.31 (3H, d, J=4.5 Hz), 2.82–3.05 (2H, m), 3.31–3.40 (3H, m), 3.79 (1H, d, J=15.5 Hz), 3.95 (1H, d, J=6.3 Hz), 4.02 (1H, d, J=16.4 Hz), 4.16 (1H, d, J=9.6 Hz), 7.28 (1H, dd, J=1.3, 8.3 Hz), 7.46 (2H, m), 7.59 (1H, s), 7.70–7.93 (6H, m).

c) N'-[4-(N-Hydroxyamino)-3S-(2-oxy-N-(2'-acetoxyethyl)acetamido)-2R-(2-naphthylmethyl)succinyl]-S-tert-leucine methylamide

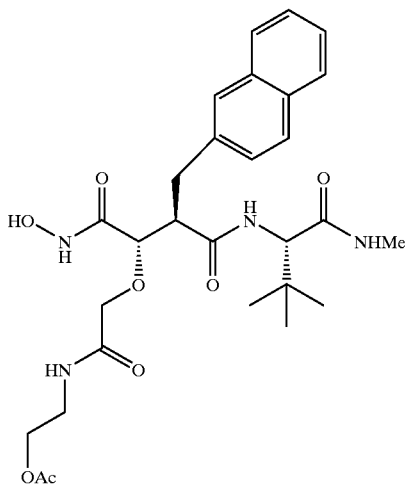

Removal of the tert-butyl ester from N'-[4-Butoxy-3S-(2-oxy-N-(2-acetoxyethyl)acetamido)-2R-(2-naphthylmethyl)succinyl]-S-tert-leucine methylamide with TFA, followed by coupling with hydroxylamine as described previously gave the title compound.

MS (ES+ve) M+Na=581, M+H=559

$^1$H NMR (DMSO-$d_6$): 0.80 (9H, s), 2.01 (3H, s), 2.17 (3H, d, J=4.5 Hz), 2.75 (1H,m), 2.88 (1H, m), 3.32 (3H, m), 3.70 (1H, d, J=15.6 Hz), 3.90 (1H, d, J=16.0 Hz), 3.94 (1H, d, J=9.9 Hz), 4.03 (2H, t, J=5.7 Hz), 4.13 (1H, d, J=9.6 Hz), 7.22 (1H, dd, J=1.3, 8.3 Hz), 7.43 (3H, m), 7.54 (1H, s), 7.72 (1H, d, J=8.5 Hz), 7.76 (1H, d, J=9.0 Hz), 7.83 (2H, m), 7.86 (1H, d, J=9.7 Hz), 9.19 (1H, s), 11.07 (1H, s).

EXAMPLE 38

N'-[4-(N-Hydroxyamino)-3S-N-(2-hydroxyethyl) carbamoylmethoxy-2R-(2-naphthylmethyl)succinyl]-S-tert-leucine methylamide

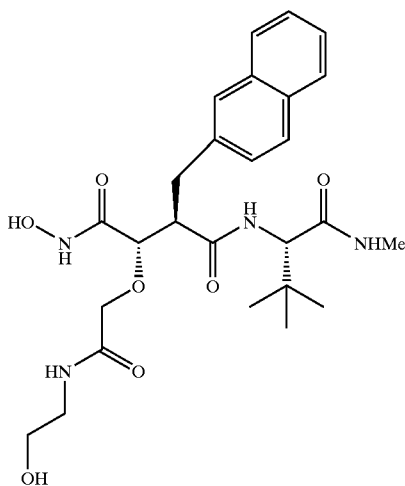

N'-[4-(N-Hydroxyamino)-3S-(2-oxy-N-(2'-acetoxyethyl)acetamido)-2R-(2-naphthylmethyl)succinyl]-S-tert-leucine methylamide (0.27 g, 0.49 mmol) in dioxan (4.4 ml)/water (3 ml) was stirred with LiOH.H$_2$O (0.062 g, 1.47 mmol) at room temperature for two hours. Amberlite IR-120 (plus) resin was added until pH=4 and then the mixture was filtered, concentrated, azeotroped with toluene and dried under vacuum to give a white solid. Purification by preparative HPLC gave the title compound.

MS (ES+ve) M+Na=539, M+H=517

MS (ES−ve) M−H=515

$^1$H NMR (DMSO-$d_6$): 0.81 (9H, s), 2.15 (3H, d, J=4.5 Hz), 2.72 (1H, dd, J=3.9, 13.5 Hz), 2.85 (1H, dd, J=10.7, 13.5 Hz), 3.12 (1H, m), 3.21 (1H, m), 3.34 (1H, m), 3.42 (2H, t, J=6.5 Hz), 3.69 (1H, d, J=15.4 Hz), 3.87 (1H, d, J=15.4 Hz), 3.93 (1H, d, J=9.7 Hz), 4.12 (1H, d, J=9.7 Hz), 7.23 (1H, dd, J=1.5, 8.4 Hz), 7.45 (3H, m), 7.54 (1H, s), 7.61 (1H, t, J=5.8 Hz), 7.72 (1H, d, J=8.5 Hz), 7.77 (1H, d, J=7.5 Hz), 7.82 (1H, d, J=8.1 Hz), 7.89 (1H, d, J=9.6 Hz), 9.30 (1H, s), 11.09 (1H, s).

EXAMPLE 39

N'-[4-(N-Hydroxyamino)-2R-(2-naphthylmethyl) succinyl-3S-(2-oxy phenacyl)]-tert-leucine methylamide

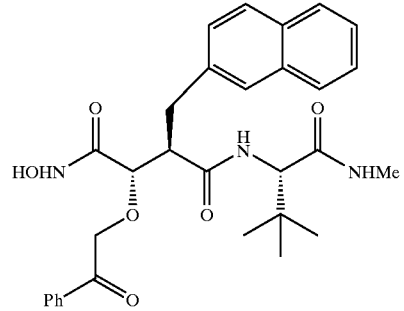

Prepared analogously to Example 1)a)+b)+c) from N-4-t-Butoxy-3S-(hydroxy)-2R-(2-naphthylmethyl)succinyl]-S-tert-leucine methylamide by alkylation with phenacyl bromide instead of allyl bromide.

MS (ES−ve) M−H=532

$^1$H NMR (DMSO-$d_6$): 0.89 (9H,s), 2.5–2.53 (3H, obs), 3.20 (2H,d, J=8 Hz), 3.50–3.60 (1H,m), 3.83 (1H, d, J=15 Hz), 3.91 (1H, d, J=15), 4.19 (1H, d, J=9 Hz), 4.21 (1H, d, J=5 Hz), 6.89 (1H, s), 7.3–7.49 (8H, m), 7.76 (1H, s), 7.8–7.9 (4H, m), 7.97 (1H, br d, J=9), 9.39 (1H, s).

N'-[4-t-Butoxy-3S-(2RS-hydroxypropoxy)-2R-(2-naphthylmethyl)succinyl]-S-tert-leucine methylamide (A) and N'-[4-t-Butoxy-3S-(3-hydroxypropoxy)-2R-(2-naphthylmethyl)succinyl]-S-tert-leucine methylamide (B)

(A)
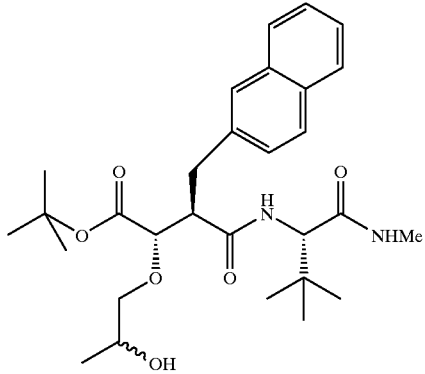

(B)
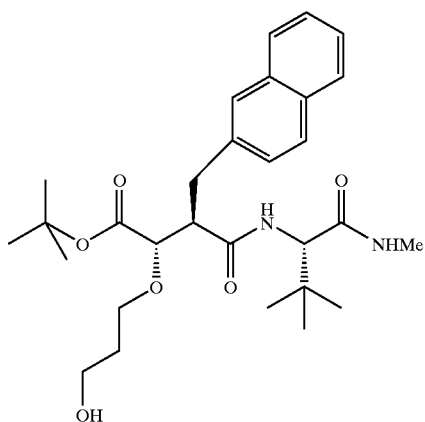

N'-[3S-Allyloxy-4-t-butoxy-2R-(2-naphthylmethyl)succinyl]-S-tert-leucine methylamide (4.0 g, 8.05 mmol) and Wilkinson's catalyst (225 mg) in THF (70 ml) were cooled to 0° C. and catechol borane (2.58 ml, 24.2 mmol) was added via syringe. The mixture was stirred at 0° C. for 30 mins and then at room temperature for 1 hr and then 1:1 THF/ethanol (25 ml), pH 7 phosphate buffer (25 ml) and 27.5% hydrogen peroxide solution (25 ml) were added and the mixture was stirred at room temperature for 24 hrs. The THF was evaporated and brine and ethyl acetate were added. The product was extracted into ethyl acetate and the extracts were washed with sodium carbonate solution and brine and then dried (Na₂SO₄) and concentrated. Purification by column chromatography on silica gel (ethyl acetate/hexane) gave A) 0.627 g (15%) and B) 1.958 g (47%)

A) MS ES+ve M+H=515

¹H NMR (DMSO-d₆): 0.84 (9H, s), 1.04 and 1.05 (3H, 2×d, J=6.0 Hz), 1.44 (9H, s), 2.24 and 2.26 (3H, 2×d, J=4.5 Hz), 2.84 (1H, dd, J=5.0, 14.0 Hz), 2.96 (1H, m), 3.10–3.38 (3H, m), 3.69 (1H, m), 3.85 and 3.87 (1H, 2×d, J=8.0 Hz), 4.09 (1H, d, J=9.5 Hz), 4.48 and 4.53 (1H, 2×d, J=4.5 Hz), 7.30 (1H, dd, J=1.5, 8.5 Hz), 7.44 (3H, m), 7.61 (1H, s), 7.69–7.86 (4H, m).

B) MS ES+ve M+H=515, M+Na=537

¹H NMR (DMSO-d₆): 0.84 (9H, s), 1.45 (9H, s), 1.63 (2H, m), 2.20 (3H, d, J=4.5 Hz), 2.76 (1H, dd, J=5.0, 13.5 Hz), 2.95 (1H, dd, J=10.0, 13.5 Hz), 3.20 (1H, m), 3.32–3.55 (4H, m), 3.79 (1H, d, J=8.5 Hz), 4.08 (1H, d, J=9.5 Hz), 4.35 (1H, t, J=5.0 Hz), 7.29 (1H, dd, J=1.5, 8.5 Hz), 7.32 (1H, m), 7.44 (2H, m), 7.60 (1H, s), 7.70 (1H, d, J=9.5 Hz), 7.74–7.84 (3H, m).

EXAMPLE 40

N'-[3S-(3-Acetoxypropoxy)-4-(N-hydroxyamino)-2R-(2-naphthylmethyl)succinyl]-S-tert-leucine methylamide

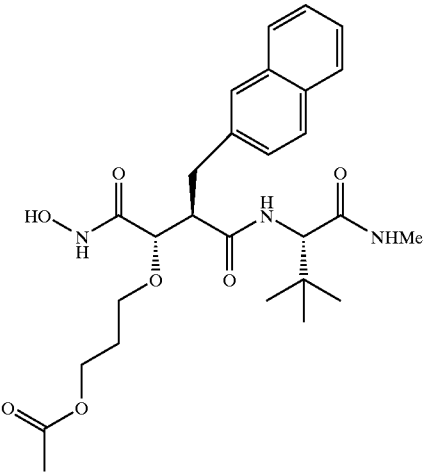

a) N'-[3S-(3-Acetoxypropoxy)-4-t-butoxy-2R-(2-naphthylmethyl)succinyl]-S-tert-leucine methylamide

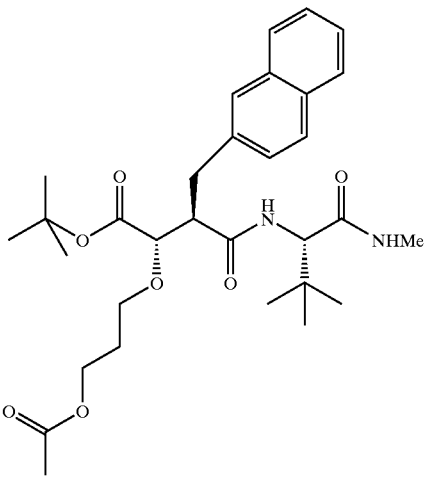

To a solution of the N'-[4-t-Butoxy-3S-(3-hydroxypropoxy)-2R-(2-naphthylmethyl)succinyl]-S-tert-leucine methylamide (193 mg, 0.3 8 mmol), pyridine (0.092 ml, 1.14 mmol) and DMAP (a few crystals) in dichloromethane (3 ml) at 0° C. was added acetic anhydride (0.053 ml, 0.56 mmol). The mixture was stirred at room temperature for 1 hr and was then diluted with ethyl acetate and washed with 1N HCl (2×), NaHCO₃ solution and brine and then dried and concentrated to give 207 mg of product.

¹H NMR (DMSO-d₆): 0.83 (9H, s), 1.45 (9H, s), 1.78 (2H, m), 1.99 (3H, s), 2.20 (3H, d, J=4.5 Hz), 2.76 (1H, dd, J=5.0, 14.0 Hz), 2.95 (1H, dd, J=10.0, 14.0 Hz), 3.21 (1H, m), 3.39 (1H, m), 3.50 (1H, m), 3.82 (1H, d, J=8.5 Hz), 4.05 (2H, m), 4.08 (1H, d, J=9.5 Hz), 7.28 (1H, dd, J=1.5, 8.5 Hz), 7.33 (1H, m), 7.44 (2H, m), 7.59 (1H, s), 7.71 (1H, d, J=9.5 Hz), 7.75–7.85 (3H, m).

b) N'-[3S-(3-Acetoxypropoxy)-4-(N-hydroxyamino)-2R-(2-naphthylmethyl)-succinyl]-S-tert-leucine methylamide

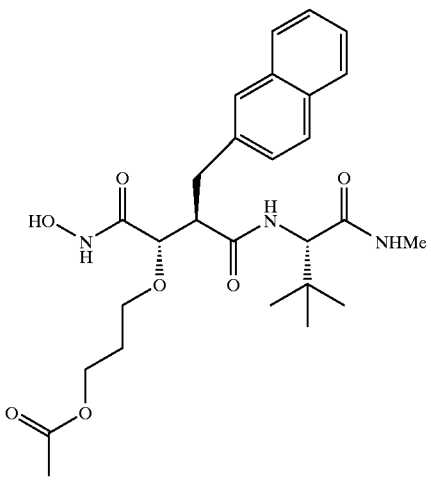

Prepared from N'-[3S-(3-Acetoxypropoxy)-4-t-butoxy-2R-(2-naphthylmethyl)succinyl]-S-tert-leucine methylamide by TFA deprotection of the ester and coupling of the resultant acid with hydroxylamine to give the title compound.

MS ES−ve M−H=514
MS ES+ve M+H=516
$^1$H NMR (DMSO-$d_6$): 0.82 (9H, s), 1.74 (2H, m), 1.99 (3H, s), 2.05 (3H, d, J=4.5 Hz), 2.65 (1H, dd, J=3.0, 13.5 Hz), 2.82 (1H, dd, J=11.0, 13.5 Hz), 3.23 (1H, m), 3.29 (1H, m, partially obscured), 3.45 (1H, m), 3.79 (1H, d, J=9.5 Hz), 3.96–4.04 (3H, m), 7.01 (1H, m), 7.25 (1H, dd, J=1.5, 8.5 Hz), 7.44 (2H, m), 7.57 (1H, s), 7.61 (1H, d, J=8.5 Hz), 7.74 (1H, d, J=8.5 Hz), 7.78 (1H, d, J=7.5 Hz), 7.84 (1H, d, J=7.5 Hz), 9.12 (1H, s), 10.91 (1H, s).

EXAMPLE 41

N'-[4-(N-Hydroxyamino)-3S-(3-hydroxypropoxy)-2R-(2-naphthylmethyl)-succinyl]-S-tert-leucine methylamide

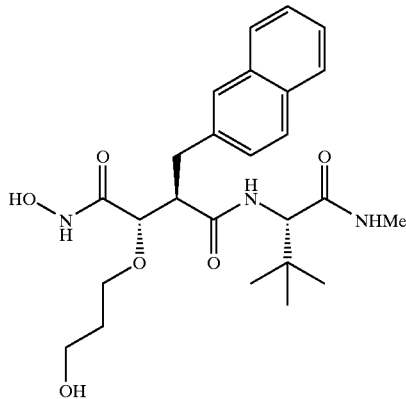

N'-[3S-(3-Acetoxypropoxy)-4-(N-hydroxyamino)-2R-(2-naphthylmethyl)succinyl]-S-tert-leucine methylamide (115 mg, 0.223 mmol) and LiOH.H$_2$O (28 mg, 0.67 mmol) were stirred in 1,4-dioxan (2 ml)/water (1.5 ml) at room temperature for 1 hr. Amberlite resin-IR120 (plus) was added to lower the pH to 3–4 and the mixture was filtered and evaporated. The product was then azeotroped with toluene, triturated with ether and dried under high vacuum to give the product as a white solid (89 mg).

MS ES−ve M−H=472
MS ES+ve M+H=474
$^1$H NMR (DMSO-$d_6$): 0.83 (9H, s), 1.59 (2H, m), 2.06 (3H, d, J=4.5 Hz), 2.66 (1H, dd, J=4.0, 13.5 Hz), 2.83 (1H, dd, J=11.0, 13.5 Hz), 3.20 (1H, m), 3.24 (1H, m. partially obscured), 3.36–3.48 (3H, m), 3.76 (1H, d, J=9.5 Hz), 4.02 (1H, d, J=9.5 Hz), 4.35 (1H, br s, exchangeable with D$_2$O), 7.04 (1H, m), 7.25 (1H, d, J=8.5 Hz), 7.44 (2H, m), 7.57 (1H, s), 7.58 (1H, d, J=8.5 Hz), 7.74 (1H, d, J=8.5 Hz), 7.78 (1H, d, J=7.5 Hz), 7.83 (1H, d, J=7.5 Hz), 9.08 (1H, s), 10.91 (1H, s).

EXAMPLE 42

N'-[3S-(3-Dimethylaminopropoxy)-4-(N-hydroxyamino)-2R-(2-naphthylmethyl)succinyl]-S-tert-leucine methylamide

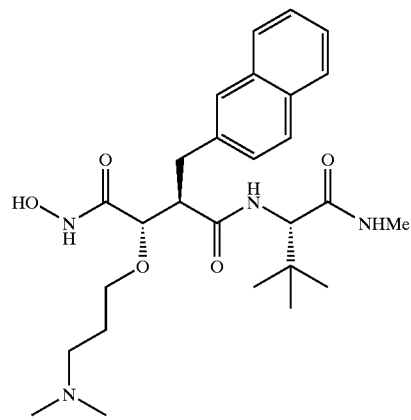

a) N'-[4-t-Butoxy-3S-(3-dimethylaminopropoxy)-2R-(2-naphthylmethyl)-succinyl]-S-tert-leucine methylamide

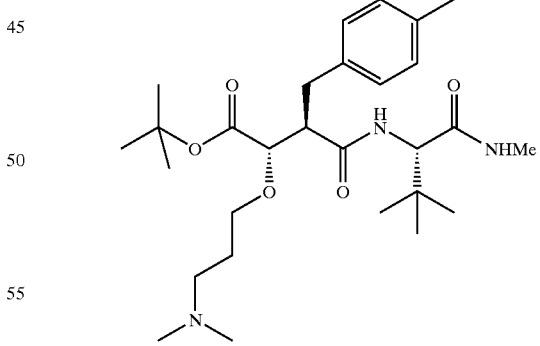

To a solution of the N'-[4-t-Butoxy-3S-(3-hydroxypropoxy)-2R-(2-naphthylmethyl)succinyl]-S-tert-leucine methylamide (800 mg, 1.56 mmol) and triethylamine (0.326 ml, 2.34 mmol) in dichloromethane (8 ml) at 0° C. was added methanesulfonyl chloride (0.145 ml, 1.87 mmol). The mixture was stirred for 40 mins and then was diluted with dichloromethane and washed with 2N HCl and brine and then dried (Na$_2$SO$_4$) and concentrated to give the mesylate as a white foam (895 mg, 97%).

The mesylate (660 mg) was stirred in ethanol (6 ml) with dimethylamine (3 ml) in a sealed vessel for 20 hrs. The solvents were evaporated and ethyl acetate and saturated sodium carbonate solution were added and the product was extracted into ethyl acetate. The extracts were washed with brine, dried ($Na_2SO_4$) and evaporated. Filtration through a short column of silica gel (elution with dichloromethane/methanol) gave a white foam (520 mg, 86%).

MS ES+ve M+H=542

$^1$H NMR (DMSO-$d_6$): 0.84 (9H, s), 1.44 (9H, s), 1.61 (2H, m), 2.11 (6H, s), 2.20 (3H, d, J=4.5 Hz), 2.27 (2H, m), 2.76 (1H, dd, J=4.5, 13.5 Hz), 2.95 (1H, dd, J=10.0, 13.5 Hz), 3.19 (1H, m), 3.32 (1H, m, partially obscured), 3.46 (1H, m), 3.80 (1H, d, J=8.5 Hz), 4.09 (1H, d, J=9.5 Hz), 7.28 (1H, dd, J=1.5, 8.5 Hz), 7.33 (1H, m), 7.44 (2H, m), 7.60 (1H, s), 7.69 (1H, d, J=9.5 Hz), 7.75 (1H, d, J=8.5 Hz), 7.78 (1H, d, J=7.5 Hz), 7.84 (1H, d, J=7.5 Hz).

b) N'-[3S-(3-Dimethylaminopropoxy)-4-(N-hydroxyamino)-2R-(2-naphthylmethyl)succinyl]-S-tert-leucine methylamide

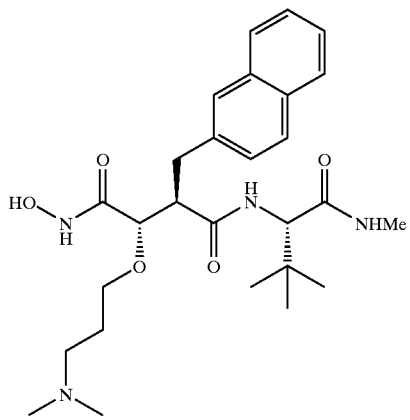

Removal of the t-butyl ester from N'-[4-t-Butoxy-3S-(3-dimethylaminopropoxy)-2R-(2-naphthylmethyl)-succinyl]-S-tert-leucine methylamide with TFA, conversion of the TFA salt to the HCl salt and coupling with O-benzylhydroxylamine and removal of the O-benzyl group by hydrogenolysis gave the title compound.

MS ES−ve M−H=499

MS ES+ve M+H=501

$^1$H NMR (DMSO-$d_6$): 0.83 (9H, s), 1.59 (2H, m), 2.09 (3H, d, J=4.5 Hz), 2.14 (6H, s), 2.27 (2H, m), 2.74(1H, dd, J=4.0, 13.5 Hz), 2.85 (1H, dd, J=11.0, 13.5 Hz), 3.19 (1H, m), 3.37 (2H, m, partially obscured), 3.76 (1H, d, J=9.0 Hz), 4.05 (1H, d, J=9.5 Hz), 7.12 (1H, m), 7.26 (1H, dd, J=1.0, 8.5 Hz), 7.43 (2H, m), 7.56 (1H, d, J=9.5 Hz), 7.57 (1H, s), 7.74 (1H, d, J=8.5 Hz), 7.78 (1H, d, J=7.5 Hz), 7.83 (1H, d, J=7.5 Hz), 9.03 (1H, s), 11.25 (1H, broad s).

EXAMPLE 43

N'-[3S-(2-RS-Acetoxypropoxy)-4-(N-hydroxyamino)-2R-(2-naphthylmethyl)-succinyl]-S-tert-leucine methylamide

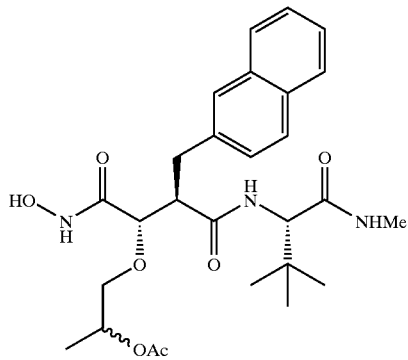

Prepared from N'-[4-t-butoxy-3S-(2RS-hydroxypropoxy)-2R-(2-naphthylmethyl)-succinyl]-S-tert-leucine methylamide as in Example 40.

MS ES−ve M−H=514

MS ES+ve M+H=516

$^1$H NMR (DMSO-$d_6$): approx. 2:1 mixture of diastereoisomers, 0.82 (9H, s), 1.11 and 1.12 (3H, 2×d, J=6.5 Hz), 1.96 and 1.97 (3H, 2×s), 2.02 and 2.05 (3H, 2×d, J=4.5 Hz), 2.68 (1H, m), 2.80 (1H, m), 3.23–3.50 (3H, m), 3.86 (1H, m), 4.00 and 4.01 (1H, 2×d, J=9.5 Hz), 4.80 (1H, m), 7.0 (1H, m), 7.25 (1H, d, J=8.5 Hz), 7.44 (2H, m), 7.57 (1H, s), 7.61 (1H, m), 7.74 (1H, d, J=8.5 Hz), 7.77–7.84 (2H, m), 9.12 and 9.14 (1H, 2×s), 10.90 (1H, s).

EXAMPLE 44

N'-[4-(N-Hydroxyamino)-3S-(2-RS-hydroxypropoxy)-2R-(2-naphthylmethyl)-succinyl]-S-tert-leucine methylamide

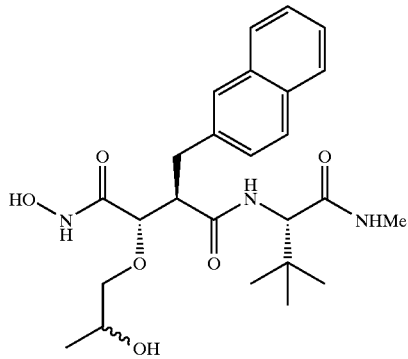

Prepared by cleavage of the acetate in N'-[3S-(2-RS-acetoxypropoxy)-4-(N-hydroxyamino)-2R-(2-naphthylmethyl)succinyl]-S-tert-leucine methylamide with lithium hydroxide as in Example 41.

MS ES−ve M−H=472

MS ES+ve M+H=474

$^1$H NMR (DMSO-$d_6$): approx. 2:1 mixture of diastereoisomers, 0.83 (9H, s), 0.98 and 1.00 (3H, 2×d, J=6.5 Hz), 2.09 and 2.11 (3H, 2×d, J=4.5 Hz), 2.67–2.89

(2H, m), 3.08–3.29 (3H, m), 3.65 (1H, m), 3.83 and 3.84 (1H, 2×d, J=9.5 Hz), 4.03 (1H, d, J=9.5 Hz), 4.50 and 4.51 (1H, 2×d, J=4.5 Hz), 7.12 and 7.19 (1H, 2×m), 7.25 (1H, m), 7.44 (2H, m), 7.57 (1H, s), 7.62 (1H, m), 7.74 (1H, d, J=8.5 Hz), 7.77–7.84 (2H, m), 9.09 and 9.11 (1H, 2×s), 10.86 and 10.90 (1H, s).

N'-[4-t-Butoxy-3S-(2-hydroxyethoxy)-2R-(2-naphthylmethyl)succinyl]-S-tert-leucine methylamide

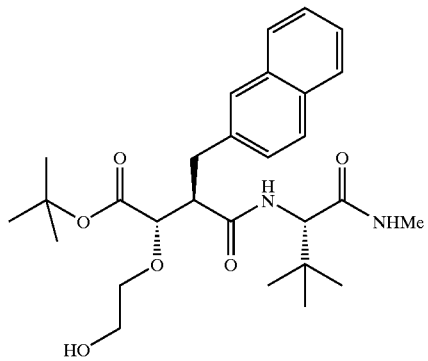

A mixture of the N'-[3S-Allyloxy-4-t-butoxy-2R-(2-naphthylmethyl)succinyl]-S-tert-leucine methylamide (2.0 g, 4.03 mmol), N-methylmorpholine N-oxide (520 mg, 4.43 mmol) and osmium tetroxide (0.8 ml of 2.5% solution in t-butanol) in acetone (24 ml), t-butanol (6 ml) and water (6 ml) was stirred at room temperature for 24 hrs. A few crystals of solid osmium tetroxide were added and the mixture was stirred for a further 24 hrs. The solvents were removed and the mixture was filtered through a short column of silica gel (ethyl acetate) to give the intermediate diol as a white foam (2.098 g, 98%).

The diol and sodium periodate (973 mg, 4.55 mmol) in 1,4-dioxan (36 ml)/water (12 ml) were stirred at room temperature for 5 hrs. A further batch of sodium periodate (90 mg) was added and stirring was continued for a further 1 hr. Sodium borohydride (757 mg, 20 mmol) was added and after stirring for 30 mins the reaction was quenched with saturated ammonium chloride solution and the solvents were removed. Ethyl acetate and 1N HCl were added and the product was extracted into ethyl acetate. The extracts were washed with sodium bicarbonate solution and brine and then dried (Na$_2$SO$_4$) and concentrated. Chromatography on silica gel (80% ethyl acetate in hexane) gave the product as a white foam (1.63 g, 82%).

MS ES+ve M+H=501

$^1$H NMR (DMSO-d$_6$): 0.84 (9H, s), 1.44 (9H, s), 2.25 (3H, d, J=4.5 Hz), 2.82 (1H, dd, J=5.0, 13.5 Hz), 2.96 (1H, dd, J=10.0, 13.5 Hz), 3.20 (1H, m), 3.36 (1H, m), 3.46–3.54 (3H, m), 3.88 (1H, d, J=8.0 Hz), 4.10 (1H, d, J=9.5 Hz), 4.51 (1H, t, J=5.5Hz), 7.30 (1H, dd, J=1.5, 8.5 Hz), 7.44 (3H, m), 7.61 (1H, s), 7.72–7.86 (4H, m).

EXAMPLE 45

N'-[3S-(2-Acetoxyethoxy)-4-(N-hydroxyamino)-2R-(2-naphthylmethyl)-succinyl]-S-tert-leucine methylamide

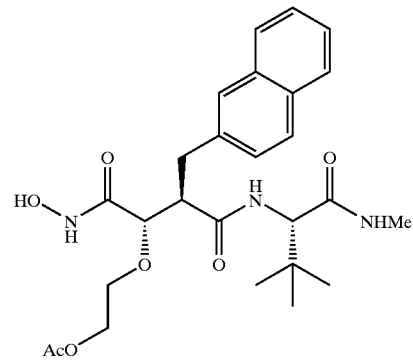

Prepared from N'-[4-t-Butoxy-3S-(2-hydroxyethoxy)-2R-(2-naphthylmethyl)-succinyl]-S-tert-leucine methylamide in an analogous manner to that described above for Example 40.

MS ES–ve M–H=500
MS ES+ve M+H=502

$^1$H NMR (DMSO-d$_6$): 0.82 (9H, s), 1.99 (3H, s), 2.05 (3H, d, J=4.5 Hz), 2.67 (1H, m), 2.82 (1H, dd, J=11.0, 13.0 Hz), 3.26 (1H, m, partially obscured), 3.46 (1H, m), 3.59 (1H, m), 3.85 (1H, d, J=9.5 Hz), 4.00–4.04 (3H, m), 7.02 (1H, m), 7.24 (1H, dd, J=1.5, 8.5 Hz), 7.44 (2H, m), 7.57 (1H, s), 7.63 (1H, d, J=9.5 Hz), 7.74 (1H, d, J=8.5 Hz), 7.77 (1H, d, J=7.5 Hz), 7.83 (1H, d, J=7.5 Hz), 9.14 (1H, s), 10.92 (1H, s).

EXAMPLE 46

N'-[4-(N-Hydroxyamino)-3S-(2-hydroxyethoxy)-2R-(2-naphthylmethyl)-succinyl]-S-tert-leucine methylamide

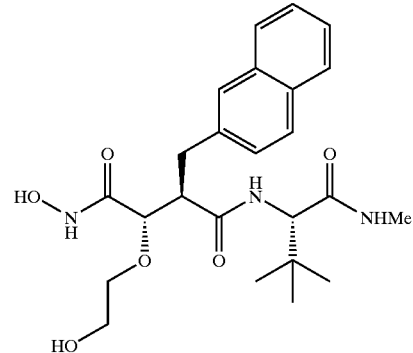

Prepared from N'-[3S-(2-Acetoxyethoxy)-4-(N-hydroxyamino)-2R-(2-naphthylmethyl)succinyl]-S-tert-leucine methylamide by cleavage of the acetate with lithium hydroxide.

MS ES–ve M–H=458
MS ES+ve M+H=460

$^1$H NMR (DMSO-d$_6$): 0.83 (9H, s), 2.12 (3H, d, J=4.5 Hz), 2.74 (1H, dd, J=4.0, 13.5 Hz), 2.85 (1H, dd, J=10.5, 13.5 Hz), 3.19 (1H, m), 3.29–3.43 (4H, m), 3.83 (1H, d, J=9.0 Hz), 4.05 (1H, d, J=9.5 Hz), 4.51 (1H, broad s, exchanges with D₂O), 7.19 (1H, m), 7.25 (1H, dd, J=1.5, 8.5 Hz), 7.43 (2H, m), 7.57 (1H, s), 7.62 (1H, d, J=9.5 Hz), 7.74 (1H, d, J=8.5 Hz), 7.78 (1H, d, J=7.5 Hz), 7.83 (1H, d, J=7.5 Hz), 9.07 (1H, s), 10.96 (1H, broad s).

EXAMPLE 47

N'-[4-(N-Hydroxyamino)-2R-(2-naphthylmethyl)-3S-(2-N-succinimidylethoxy)succinyl]-S-tert-leucine methylamide

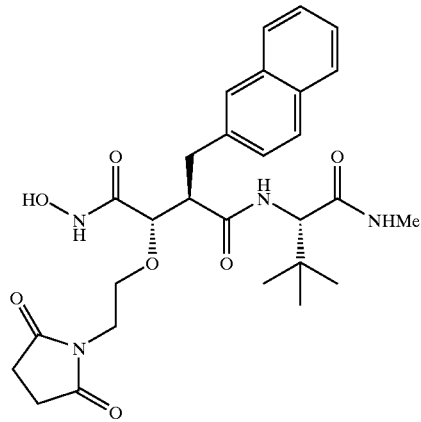

a) N'-[4-t-Butoxy-2R-(2-naphthylmethyl)-3S-(2-N-succinimidylethoxy-)succinyl]-S-tert-leucine methylamide

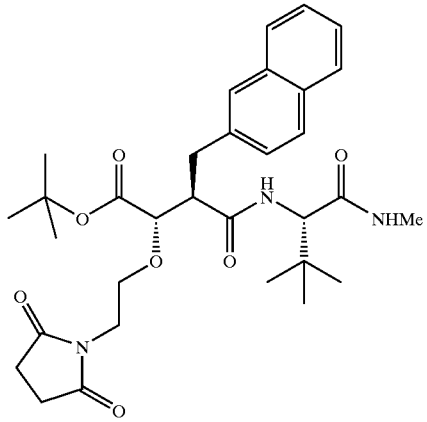

A mixture of N'-[4-t-Butoxy-3S-(2-hydroxyethoxy)-2R-(2-naphthylmethyl)-succinyl]-S-tert-leucine methylamide (320 mg, 0.64 mmol), triphenylphosphine (336 mg, 1.28 mmol), DEAD (0.202 ml, 1.28 mmol) and succinimide (127 mg, 1.28 mmol), in THF (4 ml) was stirred at room temperature overnight. The solvents were evaporated and the residue was chromatographed on silica gel (elution with ethyl acetate/hexane) to give the title compound contaminated with a small amount of triphenylphosphine oxide which was removed at the next stage.
MS ES+ve M+H 582, M+Na 604.

b) N'-[4-(N-Hydroxyamino)-2R-(2-naphthylmethyl)-3S-(2-N-succinimidylethoxy)succinyl]-S-tert-leucine methylamide

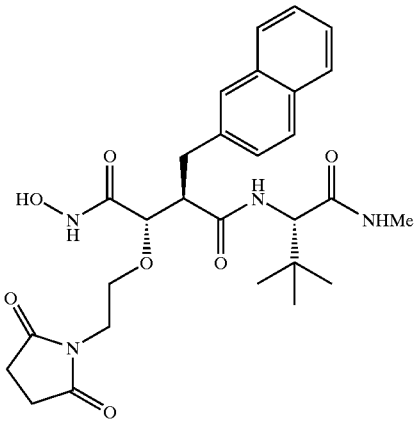

Cleavage of the t-butyl ester from N'-[4-t-Butoxy-2R-(2-naphthylmethyl)-3S-(2-N-succinimidylethoxy)-succinyl]-S-tert-leucine methylamide with TFA, followed by chromatography (to remove triphenylphosphine oxide) and conversion of the carboxylic acid to the hydroxamic acid using standard conditions gave the title compound.
MS ES–ve M–H=539
MS ES+ve M+H=541, M+Na=563
¹H NMR (DMSO-d₆): 0.85 (9H, s), 2.06 (3H, d, J=4.5 Hz), 2.60 (4H, s), 2.64 (1H, dd, J=3.5, 13.5 Hz), 2.82 (1H, dd, J=11.0, 13.5 Hz), 3.22 (1H, m), 3.27–3.50 (4H, m, partially obscured), 3.81 (1H, d, J=9.5 Hz), 4.04 (1H, d, J=9.5 Hz), 7.04 (1H, m), 7.23 (1H, dd, J=1.5, 8.5 Hz), 7.44 (2H, m), 7.57 (1H, s), 7.61 (1H, d, J=9.5 Hz), 7.73 (1H, d, J=8.5 Hz), 7.78 (1H, d, J=7.5 Hz), 7.84 (1H, d, J=7.5 Hz), 9.13 (1H, s), 10.92 (1H, s).

EXAMPLE 48

N'-[3S-(2-Dimethylaminoethoxy)-4-(N-hydroxyamino)-2R-(2-naphthylmethyl)succinyl]-S-tert-leucine methylamide

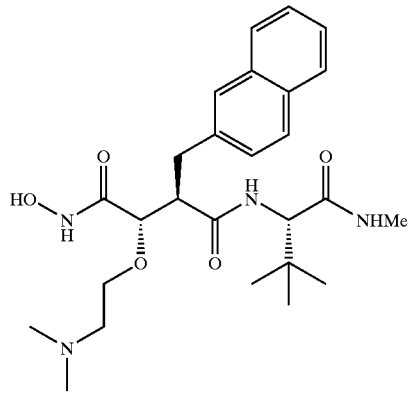

Prepared from N'-[4-t-butoxy-3S-(2-hydroxyethoxy)-2R-(2-naphthylmethyl)-succinyl]-S-tert-leucine methylamide in analogous fashion to Example 42.
MS ES–ve M–H=485
MS ES+ve M+H=487
¹H NMR (DMSO-d₆): 0.84 (9H, s), 2.10 (3H, d, J=4.5 Hz), 2.14 (6H, s), 2.35 (2H, m), 2.74 (1H, dd, J=4.0, 13.5 Hz), 2.86 (1H, dd, J=10.5, 13.5 Hz), 3.22 (1H, m), 3.30–3.50 (2H, m, partially obscured), 3.80 (1H, d, J=9.0 Hz), 4.04

(1H, d, J=9.5 Hz), 7.12 (1H, m), 7.25 (1H, dd, J=1.0, 8.5 Hz), 7.44 (2H, m), 7.56 (1H, d, J=9.5 Hz), 7.58 (1H, s), 7.74 (1H, d, J=8.5 Hz), 7.78 (1H, d, J=7.5 Hz), 7.84 (1H, d, J=7.5 Hz), 9.06 (1H, s), 11.08 (1H, broad s).

EXAMPLE 49

N'-[3S-(2-Acetoxyethoxy)-4-(N-hydroxyamino)-2R-(2-naphthylmethyl)-succinyl]-S-tert-leucine ethylamide

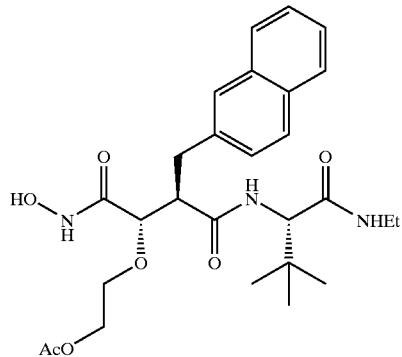

Prepared from N'-[4-t-butoxy-3S-(2-hydroxyethoxy)-2R-(2-naphthylmethyl)succinyl]-S-tert-leucine ethylamide in an analogous fashion to Example 40.

MS ES−ve M−H=514

MS ES+ve M+H=516, M+Na=538

$^1$H NMR (DMSO-$d_6$): 0.66 (3H, t, J=7.0 Hz), 0.83 (9H, s), 1.99 (3H, s), 2.50–2.70 (3H, m, partially obscured), 2.84 (1H, m), 3.28 (1H, m, partially obscured), 3.47 (1H, m), 3.60 (1H, m), 3.85 (1H, d, J=9.5 Hz), 4.01–4.04 (3H, m), 7.21 (1H, m), 7.25 (1H, dd, J=1.5, 8.5 Hz), 7.43 (2H, m), 7.57 (1H, s), 7.63 (1H, d, J=8.5 Hz), 7.72 (1H, d, J=8.5 Hz), 7.75–7.85 (2H, m), 9.14 (1H, s), 10.93 (1H, s).

EXAMPLE 50

N'-[4-(N-Hydroxyamino)-3S-(2-hydroxyethoxy)-2R-(2-naphthylmethyl)-succinyl]-S-tert-leucine ethylamide

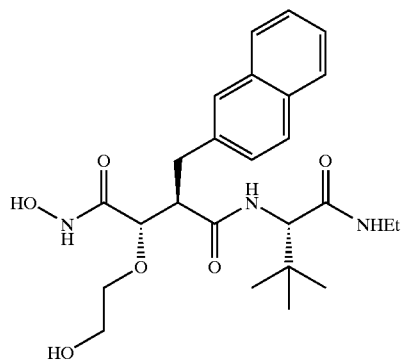

Prepared via cleavage of the acetate from N'-[3S-(2-acetoxyethoxy)-4-(N-hydroxyamino)-2R-(2-naphthylmethyl)succinyl]-S-tert-leucine ethylamide with lithium hydroxide MS ES−ve M−H=472

MS ES+ve M+H=474

$^1$H NMR (DMSO-$d_6$): 0.71 (3H, t, J=7.0 Hz), 0.84 (9H, s), 2.58–2.76 (3H, m), 2.86 (1H, m), 3.20 (1H, m), 3.29–3.44 (4H, m), 3.82 (1H, d, J=9.5 Hz), 4.05 (1H, d, 9.5 Hz), 4.53 (1H, t, J=5.5 Hz), 7.25 (1H, dd, J=1.5, 8.5 Hz), 7.35 (1H, m), 7.43 (2H, t), 7.57 (1H, s), 7.61 (1H, d, J=9.5 Hz), 7.73 (1H, d, J=8.5 Hz), 7.77 (1H, d, J=7.5 Hz), 7.83 (1H, d, J=7.5 Hz), 9.09 (1H, s), 10.88 (1H, s).

EXAMPLE 51

N'-[3S-(2-Dimethylaminoethoxy)-4-(N-hydroxyamino)-2R-(2-naphthylmethyl)succinyl]-S-tert-leucine ethylamide

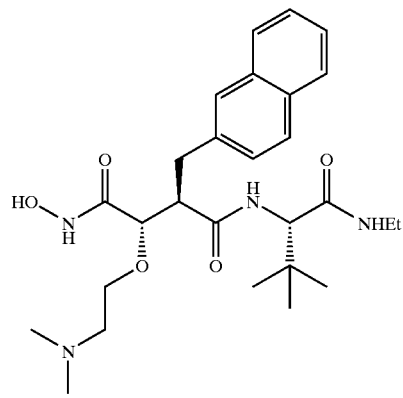

Prepared from N'-[4-t-butoxy-3S-(2-hydroxyethoxy)-2R-(2-naphthylmethyl)-succinyl]-S-tert-leucine ethylamide in analogous fashion to Example 42.

MS ES−ve M−H=499

ES+ve M+H=501

$^1$H NMR (DMSO-$d_6$): 0.70 (3H, t, J=7.0 Hz), 0.85 (9H, s), 2.22 (6H, s), 2.45 (2H, m, partially obscured), 2.60–2.76 (3H, m), 2.87 (1H, dd, J=10.5, 13.0 Hz), 2.24 (1H, m), 3.41 (1H, m), 3.49 (1H, m), 3.81 (1H, d, J=9.0 Hz), 4.04 (1H, d, J=9.5 Hz), 7.26 (1H, dd, J=1.0, 8.5 Hz), 7.30 (1H, s), 7.44 (2H, m), 7.56 (2H, m), 7.72 (1H, d, J=8.5 Hz), 7.77 (1H, d, J=7.5 Hz), 7.80 (1H, m), 9.08 (1H, s), 11.10 (1H, br s).

EXAMPLE 52

N'-[4-(N-hydroxyamino)-3S-(2-(1-imidazolyl)ethoxy)-2R-(2-naphthylmethyl)-succinyl]-S-tert-leucine ethylamide

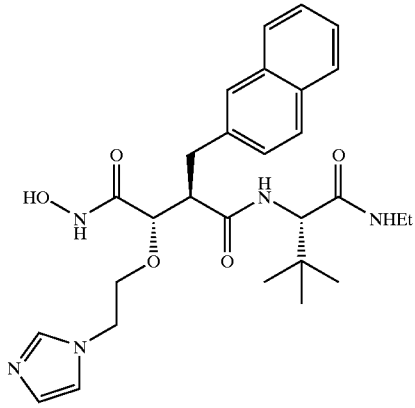

a) N'-[4-t-Butoxy-3S-(2-(1-imidazolyl)ethoxy)-2R-(2-naphthylmethyl)-succinyl]-S-tert-leucine ethylamide

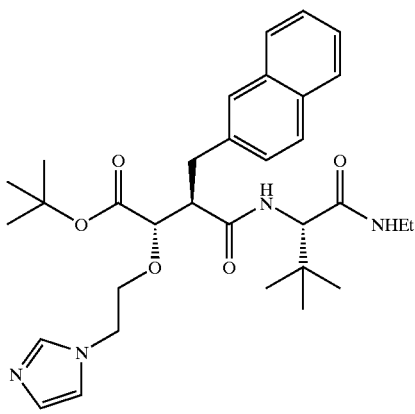

A solution of the mesylate (456 mg, 0.770 mmol) prepared from N'-[4-t-butoxy-3S-(2-hydroxyethoxy)-2R-(2-naphthylmethyl)succinyl]-S-tert-leucine ethylamide (analogously to Example 42) and imidazole (115 mg, 1.69 mmol) in DMF (10 ml) was heated at 100° C. for 7 hrs. The DMF was evaporated and ethyl acetate and sodium carbonate solution were added. The product was extracted into ethyl acetate and the extracts were washed with brine and then dried ($Na_2SO_4$) and evaporated. Chromatography on silica gel (elution with dichloromethane/methanol) gave the title compound as a white foam (44%).

MS ES+ve M+H=565

$^1$H NMR (DMSO-$d_6$): 0.80 (3H, t, J=7.0 Hz), 0.86 (9H, s), 1.37 (9H, s), 2.70–2.85 (3H, m), 2.96 (1H, dd, J=9.5, 13.0 Hz), 3.25 (1H, m), 3.57 (1H, m), 3.70 (1H, m), 3.80 (1H, d, J=7.5 Hz), 4.04–4.20 (3H, m, including d at 4.12, J=9.5 Hz), 6.90 (1H, s), 7.23 (1H, m), 7.26 (1H, s), 7.40–7.48 (3H, m), 7.62 (1H, m), 7.70 (1H, s), 7.74–7.85 (4H, m).

b) N'-[4-(N-Hydroxyamino)-3S-(2-(1-imidazolyl)ethoxy)-2R-(2-naphthylmethyl)succinyl]-S-tert-leucine ethylamide

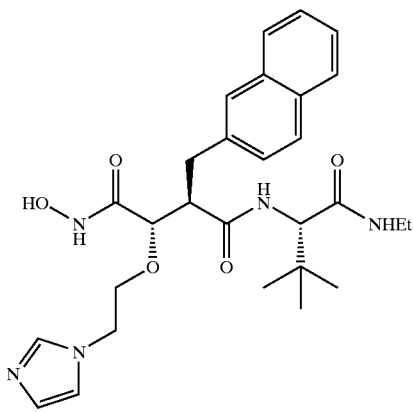

Removal of the t-butyl ester from N'-[4-t-Butoxy-3S-(2-(1-imidazolyl)ethoxy)-2R-(2-naphthylmethyl)-succinyl]-S-tert-leucine ethylamide with TFA, conversion of the TFA salt to the HCl salt and coupling with O-benzylhydroxylamine and removal of the O-benzyl group by hydrogenolysis gave the title compound.

MS ES–ve M–H=522

MS ES+ve M+H=524, $^1$H NMR (DMSO-$d_6$): 0.67 (3H, t, J=7.0 Hz), 0.82 (9H, s), 2.50–2.68 (3H, m), 2.84 (1H, dd, J=11.0, 13.5 Hz), 3.32 (1H, m, partially obscured), 3.55 (1H, m), 3.65 (1H, m), 3.88 (1H, d, J=9.5 Hz), 4.01–4.11 (3H, m), 6.87 (1H, s), 7.18 (1H, s), 7.19–7.26 (2H, m), 7.43 (2H, m), 7.55 (1H, s), 7.62 (1H, s), 7.71 (1H, d, J=9.5 Hz), 7.73 (1H, d, J=8.5 Hz), 7.77 (1H, d, J=7.5 Hz), 7.80 (1H, d, J=7.5 Hz), 9.15 (1H, s), 10.93 (1H, s).

EXAMPLE 53

N'-[4-(N-Hydroxyamino)-3S-(2-methoxyethoxy)-2R-(2-naphthylmethyl)-succinyl]-S-tert-leucine ethylamide

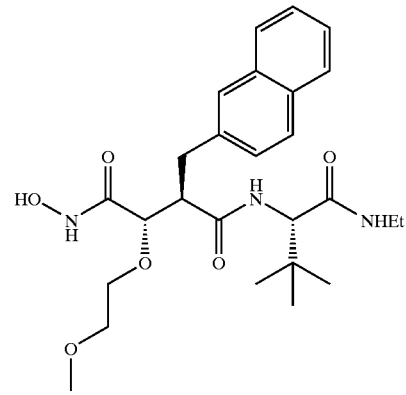

a) N'-[4-t-Butoxy-3S-(2-methoxyethoxy)-2R-(2-naphthylmethyl)succinyl]-S-tert-leucine ethylamide

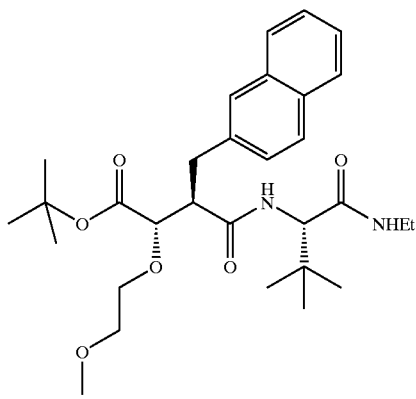

To a solution of N'-[4-t-Butoxy-3S-(2-hydroxyethoxy)-2R-(2-naphthylmethyl)-succinyl]-S-tert-leucine ethylamide (617 mg, 1.2 mmol) and proton sponge (514 mg, 2.4 mmol) in dichloromethane (10 ml) was added trimethyloxonium tetrafluoroborate (355 mg, 2.4 mmol). After stirring at room temperature for 3 hrs, further quantities of proton sponge (130 mg) and trimethyloxonium tetrafluoroborate (90 mg) were added and the mixture was stirred for a further 2 hrs. Ethyl acetate and 2N HCl were added and the product was extracted into ethyl acetate. The extracts were washed with sodium bicarbonate solution and brine and then dried (MgSO$_4$) and concentrated. The product was chromatographed on silica gel (elution with ethyl acetate/hexane) to give the product as a white foam (88% yield).

MS ES+ve M+H=529, M+Na=551

$^1$H NMR (DMSO-d$_6$): 0.77 (3H, t, J=7.2 Hz), 0.86 (9H, s), 1.44 (9H, s), 2.72–2.81 (3H, m), 2.97 (1H, dd, J=10.0, 14.0 Hz), 3.22 (1H, m), 3.24 (3H, s), 3.41–3.47 (3H m), 3.60 (1H, m), 3.86 (1H, d, J=8.0 Hz), 4.09 (1H, d, J=9.5 Hz), 7.29 (1H, dd, J=8.5, 10.0 Hz), 7.40–7.55 (3H, m), 7.60 (1H, s), 7.70 (1H, d, J=9.5 Hz), 7.75 (1H, d, J=8.5 Hz), 7.77–7.85 (2H, m).

b) N'-[4-(N-Hydroxyamino)-3S-(2-methoxyethoxy)-2R-(2-naphthylmethyl)-succinyl]-S-tert-leucine ethylamide

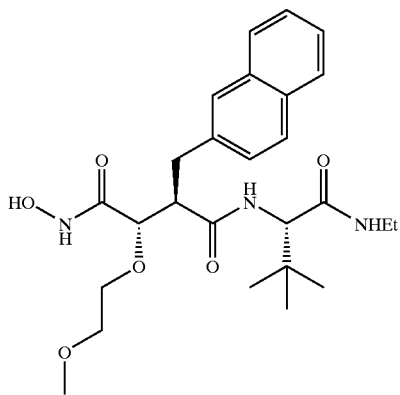

The t-butyl ester from N'-[4-t-Butoxy-3S-(2-methoxyethoxy)-2R-(2-naphthylmethyl)succinyl]-S-tert-leucine ethylamide was removed with TFA and the resulting carboxylic acid was converted to the hydroxamic acid as above to give the title compound.

MS ES–ve M–H=486
MS ES+ve M+H=488, M+Na=510

$^1$H NMR (DMSO-d$_6$): 0.67 (3H, t, J=7.5 Hz), 0.85 (9H, s), 2.50–2.69 (3H, m, partially obscured), 2.84 (1H, m), 3.20 (3H, s), 3.24 (1H, m), 3.39 (3H, m), 3.52 (1H, m), 3.80 (1H, d, J=9.5 Hz), 4.03 (1H, d, J=9.5 Hz), 7.24 (2H, m), 7.43 (2H, m), 7.58 (2H, m), 7.72 (1H, d, J=8.5 Hz), 7.75–7.85 (2H, m), 9.10 (1H, s), 10.90 (1H, s).

EXAMPLE 54

N'-[3S-Ethoxy-4-(N-hydroxyamino)-2R-(2-benzothiophenylmethyl)succinyl]-S-tert-leucine methylamide

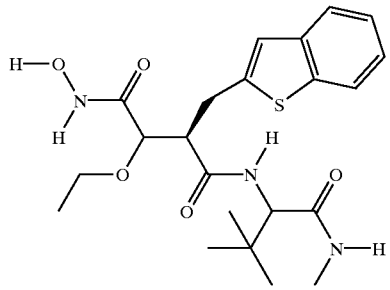

Prepared analogously to Example 1)a)+b)+c) from N-3S-Hydroxy-2R-4-methoxy-(2-benzothiophenylmethyl)succinyl]-S-tert-leucine methylamide by alkylation with iododethane instead of allyl bromide.

MS (ES+ve) M+H=450

$^1$H NMR (DMSO-d$_6$): 0.87 (9H, s), 1.04 (3H, t, J=6.9 Hz), 2.23 (3H, d, J=4.5 Hz), 2.71 (1H, td, J=1.8 Hz, 15.6 Hz), 2.99 (1H, t, J=15.6 Hz), 3.21 (2H, m), 3.43 (1H, m), 3.74 (1H, d, J=9.5 Hz), 4.14 (1H, d, J=9.5 Hz), 7.07. (1H, s), 7.28 (2H, m), 7.40 (1H, q, J=4.6 Hz), 7.65 (1H, d, J=7.3 Hz), 7.82 (2H, m), 9.10 (1H, s), 10.90 (1H, s).

EXAMPLE 55

N'-[4-(N-Hydroxyamino)-3S-cyclohexyloxy-2R-(2-naphthylmethyl)succinyl]-S-tert-leucine methylamide

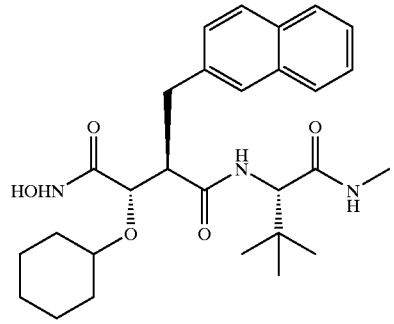

Prepared analogously to Example 1)a)+b)+c) from N-4-t-Butoxy-3S-(hydroxy)-2R-(2-naphthylmethyl)succinyl]-S-tert-leucine methylamide by alkylation with cyclohexenyl bromide (instead of allyl bromide), followed by hydrogenation.

MS (ES+ve) M+H=498

$^1$H NMR (DMSO-d$_6$) 0.84 (9H, s), 1.10 (5H, m), 1.45 (1H, m), 1.64 (2H, m), 1.75 (1H, m), 1.84 (1H, m), 2.01(3H, d, J=4.5 Hz), 2.67 (1H, J=4,13.5 Hz), 2.82 (1H, dd, J=13.5, 11 Hz), 3.19 (2H, m), 3.97 (2H, m), 6.91 (1H, q, J=4.5 Hz), 7.28 (1H, m), 7.43 (2H, m), 7.52 (1H, d, J=9 Hz), 7.59 (1H, s), 7.79 (3H, m), 9.07(1H, s), 10.87(1H, s).

EXAMPLE 56

N'-[4-(N-Hydroxyamino)-3S-(2-hydroxy-2-phenylethoxy)-2R-(2-naphthylmethyl)succinyl]-S-tert-leucine methylamide

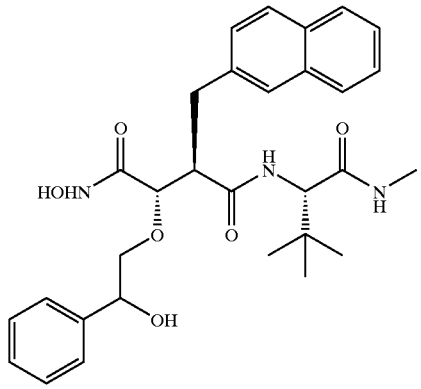

Prepared analogously to Example 1)a)+b)+c) from N-4-t-Butoxy-3S-(hydroxy)-2R-(2-naphthylmethyl)succinyl]-S-tert-leucine methylamide by alkylation with phenacyl bromide instead of allyl bromide and reduction with triethylsilane and TFA.

MS (ES+ve) M+H=536

$^1$H NMR (DMSO-$d_6$) 0.88 (9H, s), 2.19 (3H, d, J=4.5 Hz), 2.82 (2H, m), 3.23 (1H, m), 3.40 (2H, d), 3.89 (1H, d, J=9 Hz), 4.09 (1H, d, J=9 Hz), 4.70 (1H, m), 5.32(1H, br.s), 7.28 (7H, m), 7.43 (2H, m), 7.54 (1H, s), 7.66 (1H, d), 7.78 (3H, m), 9.11 (1H, s), 10.86(1H, s).

EXAMPLE 57

N'-[4-(N-Hydroxyamino)-3S-[2-(morpholin-4-yl)-2-oxoethoxy]-2R-(2-naphthylmethyl)succinyl]-S-tert-leucine methylamide

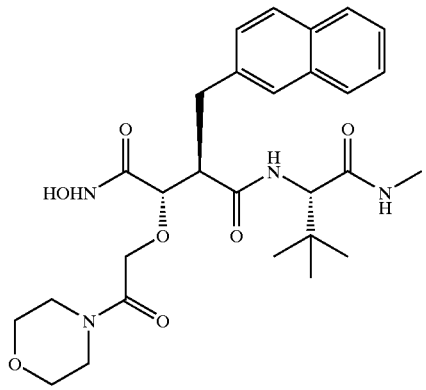

Prepared analogously to Example 1)a)+b)+c) from N-4-t-Butoxy-3S-(hydroxy)-2R-(2-naphthylmethyl)succinyl]-S-tert-leucine methylamide by alkylation with N-(2-Bromoacetyl)morpholinamide instead of allyl bromide.

MS (ES+ve) M+H=543

$^1$H NMR (DMSO-d6) 0.80 (9H, s), 2.11 (3H, d, J=4.5 Hz), 2.71 (1H, dd, J=4,14 Hz), 2.87 (1H, dd, J=11,14 Hz), 3.27–3.64 (9H, m), 3.91 (1H, d, J=9 Hz), 3.96 (1H, d J=12.5 Hz), 4.03 (1H, d, J=9.5 Hz), 4.13 (1H, d, J=12.5 Hz), 7.19 (1H, q, J=4.5 Hz), 7.26 (1H, m), 7.45 (2H, m), 7.58 (1H, s), 7.75 (4H, m), 9.14 (1H, s), 11.08 (1H, s).

EXAMPLE 58

N'-[4-(N-Hydroxyamino)-3S-ethoxy-2R-(2-naphthylmethyl)succinyl]-S-(N,N-dimethyl lysine) methylamide

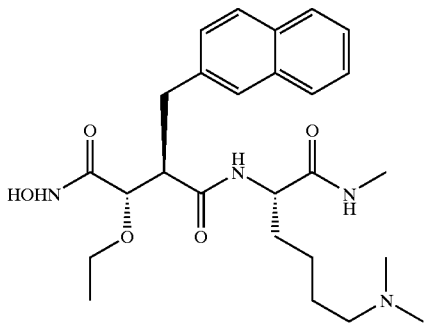

MS (ES+ve) M+H=487

$^1$H NMR (DMSO-$d_6$) 1.06 (3H,t, J=7 Hz), 1.13 (1H, m), 1,30 (4H, m), 1.59 (1H, m), 1.84 (3h, d, J=4.5 Hz), 2.08 (8H, m), 2.65 (1H, dd), 2.81 (1H, dd), 3.16 (1H, m), 3.30 (1H, m, partially obscured by water), 3.45 (1H, m), 3.78 (1H, d, J=9.5 Hz), 4.00 (1H, m), 5.86 (1H, m), 7.29 (1H, m), 7.45 (2H, m), 7.64 (1H, s), 7.85 (3H, m), 7.98 (1H, d), 9.02 (1H, br.s), 11.00 (1H, br.s).

EXAMPLE 59

N'-[4-(N-Hydroxyamino)-3S-propoxy-2R-(2-naphthylmethyl)succinyl]-S-(N,N-dimethyl-β,β-dimethyl-lysine)ethylamide

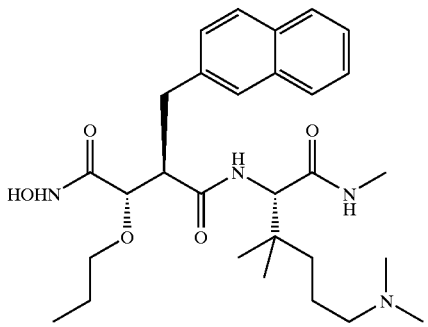

MS (ES+ve) M+H=543

$^1$H NMR (DMSO-$d_6$) 0.66 (3H, t, J=7 Hz), 0.84 (9H, m), 1.15 (2H, m), 1.35 (2H, m), 1.47 (2H, m), 2.07 (8H, m), 2.63 (2H, m), 2.84 (1H, dd, J=11, 14 Hz), 3.16–3.40 (m, obscured by water), 3.76 (1H, d, J=9.5 Hz), 4.08 (1H, d, J=9.5 Hz), 7.26 (2H, m), 7.43 (2H, m), 7.52 (1H, d. J=9.5 Hz), 7.57 (1H, s), 7.75 (3H, m), 9.14 (1H, v.br.s), 10.87 (1H, v.br.s).

EXAMPLE 60

N'-[4(N-Hydroxyamino)-3S-[2-(4-methyl-piperazin-1-yl)-2-oxo-ethoxy]-2R-(2-naphthylmethyl)succinyl]-S-tert-leucine methylamide

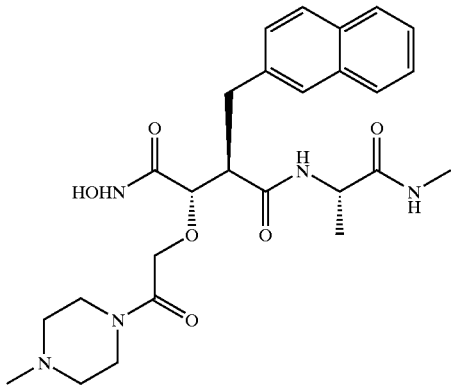

Prepared analogously to Example 1)a)+b)+c) from N-4-t-Butoxy-3S-(hydroxy)-2R-(2-naphthylmethyl)succinyl]-S-tert-leucine methylamide by alkylation with N-(2-Bromoacetyl)-N'-methylpiperazinamide instead of allyl bromide.

MS (ES+ve) M+H=556

$^1$H NMR (DMSO-d$_6$) 0.81 (9H, s), 2.11 (3H, d, J=4.5 Hz), 2.17 (3H, s), 2.18–2.35 (4H, m), 2.72 (1H, dd, J=4,14 Hz), 2.88 (1H, dd, J=11,14 Hz), 3.27–3.52 (m, partially obscured by water), 3.91 (1H, d, J=9.0 Hz), 3.96 (1H, d, J=12.5 Hz), 4.03 (1H, d, J=9.5 Hz), 4.13 (1H, d, J=12.5 Hz), 7.16 (1H, q, J=4.5 Hz), 7.26 (1H, m), 7.44 (2H, m), 7.58 (1H, s), 7.65 (1H, d, J=9.5 Hz), 7.70–7.86 (3H, m), 9.12 (1H, s), 11.09 (1H, s).

EXAMPLE 61

N'-[4-(N-Hydroxyamino)-3S-ethoxy-2R-(2-naphthylmethyl)succinyl]-S-tert-leucine t-butylamide

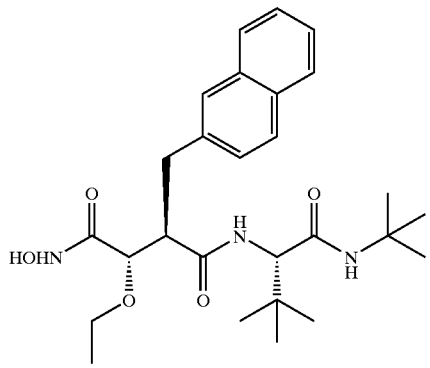

Prepared analogously to Example 1)a)+b)+c) from N-4-t-Butoxy-3S-(hydroxy)-2R-(2-naphthylmethyl)succinyl]-S-tert-leucine t_butylamide by alkylation with iodoethane instead of allyl bromide.

MS (ES+ve) M+H=486

$^1$H NMR (DMSO-d$_6$): 0.84 (9H, s), 0.92 (9H, s), 1.05 (3H, t, J=7 Hz), 2.62 (1H, dd, J=3,13.5 Hz), 2.85 (1H, dd, J=13,11.5 Hz), 3.19 (1H, m), 3.29 (1H, m obscured by water), 3.44 (1H, m), 3.75 (1H, d, J=10 Hz), 4.08 (1H, d, J=9.5 Hz), 7.07 (1H, s), 7.25 (1H, d, J=8.5 Hz), 7.41 (2H, m), 7.48 (1H, d, J=9.5 Hz), 7.56 (1H, s), 7.71 (1H, d, J=8.5 Hz), 7.77 (2H, d, J=8.5 Hz), 9.10 (1H, s), 10.92 (1H, s).

EXAMPLE 62

N'-[4-(N-Hydroxyamino)-3S-allyloxy-2R-(2-naphthylmethyl)succinyl]-S-tert-leucine t-butylamide

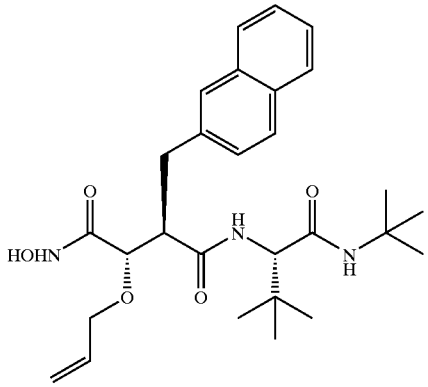

Prepared analogously to Example 1)a)+b)+c) from N-4-t-Butoxy-3S-(hydroxy)-2R-(2-naphthylmethyl)succinyl]-S-tert-leucine t_butylamide by alkylation with allyl bromide.

MS (ES+ve) M+H=498

$^1$H NMR (DMSO-d$_6$) 0.82 (9H, s), 0.92 (9H, s), 2.63 (1H, dd), 2.86 (1H, dd), 3.24 (1H, m), 3.79 (1H, dd), 3.82 (1H, d, J=10 Hz), 3.94 (1H, dd), 4.07 (1H, d, obscured), 5.10 (1H, dd), 5.22 (1H, dd, J=1.5,17.5 Hz), 5.77 (1H, m), 7.07 (1H, s), 7.25 (1H, dd), 7.41 (2H, m), 7.54 (2H, m), 7.71 (1H, d, J=8.5 Hz), 7.78 (2H, dd, J=8.5 Hz), 9.10 (1H, s), 10.93 (1H, s).

EXAMPLE 63

N'-[4-(N-Hydroxyamino)-3S-propoxy-2R-(2-naphthylmethyl)succinyl]-S-tert-leucine t-butylamide

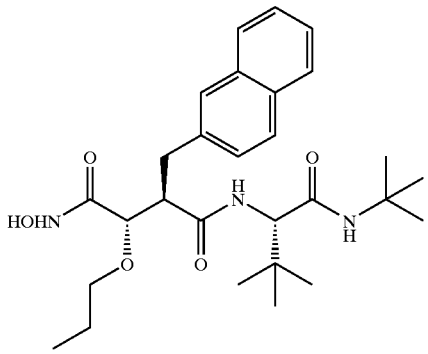

Prepared analogously to Example 1)a)+b)+c) from N-4-t-Butoxy-3S-(hydroxy)-2R-(2-naphthylmethyl)succinyl]-S-tert-leucine t_butylamide by alkylation with iodopropane instead of allyl bromide.

MS (ES+ve) M+H=500

¹H NMR (DMSO-d₆) 0.82 (3H, t, J=7.5 Hz), 0.84 (9H, s), 0.97 (9H, s), 1.45 (2H, m), 2.63 (1H, dd, J=3.5,13.5 Hz), 2.85 (1H, dd, J=11.5 Hz), 3.18 (2H, m), 3.11 (1H, m, obscured by water), 3.75 (1H, d, J=9.5 Hz), 4.07 (1H, m), 7.06 (1H, s), 7.25 (1H, d, J=8.5 Hz), 7.44 (3H, m), 7.56 (1H, s), 7.72 (1H, d, J=8.5 Hz), 7.78 (2H, d, 8.5 Hz), 9.09 (1H, s), 10.88 (1H, s).

EXAMPLE 64

N'-[4-(N-Hydroxyamino)-3S-allyloxy-2R-(2-naphthylmethyl)succinyl]-S-tert-leucine benzyl ester

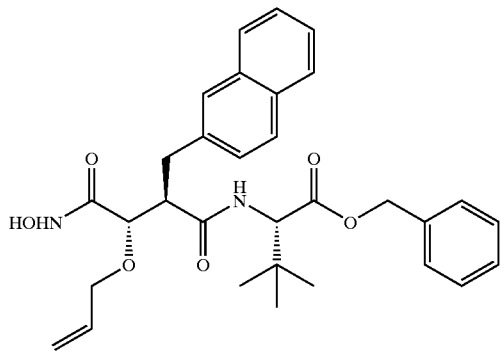

MS (ES+ve) M+H 533

¹H NMR (DMSO-d₆) 0.81 (9H, s), 2.63 (1H, dd, J=3.5, 13.5 Hz), 2.82 (1H, dd, J=13.5,8 Hz), 3.35 (1H, m), 3.76 (1H, dd, J=5.5,13 Hz), 3.84 (1H, d, J=10 Hz), 3.93 (1H, dd, J=5,13 Hz), 4.18 (1H, d, J=9 Hz), 4.42 (1H, d, J=12 Hz), 4.59 (1H, d, J=12.5 Hz), 5.08 (1H, d, J=10.5 Hz), 5.20 (1H, d, J=17 Hz), 5.74 (1H, m), 7.13 (2H, m), 7.23 (1H, d, J=8.5 Hz), 7.29 (2H, m), 7.42 (2H, m), 7.57 (1H, s), 7.68 (1H, d, J=8.5 Hz), 7.80 (2H, m), 8.05 (1H, d), 9.11 (1H, s), 10.98 (1H, s).

EXAMPLE 65

N'-[4-(N-Hydroxyamino)-3S-propoxy-2R-(2-naphthylmethyl)succinyl]-S-tert-leucine methoxyamide

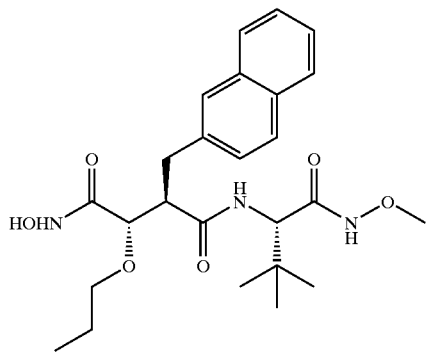

MS (ES+ve) M+H=474

¹H NMR (DMSO-d₆) 0.81 (3H, t, J=7.5 Hz), 0.85 (9H, s), 1.44 (2H, m), 2.64 (1H, dd, J=3.5,13.5 Hz), 2.85 (1H, dd, J=13.5,11 Hz), 3.12 (1H, s), 3.20 (3H, m), 3.77 (1H, d, J=9.5 Hz), 3.96 (1H, d, J=9.5 Hz), 7.26 (1H, d, J=8.5 Hz), 7.41 (2H, m), 7.56 (1H, s), 7.72 (1H, d, J=8.5 Hz), 7.78 (3H, m), 9.09 (1H, s), 10.88 (1H, s), 10.94 (1H, s).

EXAMPLE 66

N'-[4-(N-Hydroxyamino)-3S-propoxy-2R-(2-naphthylmethyl)succinyl]-S-tert-leucine (N,N-dimethylaminoeth-2-yl)amide

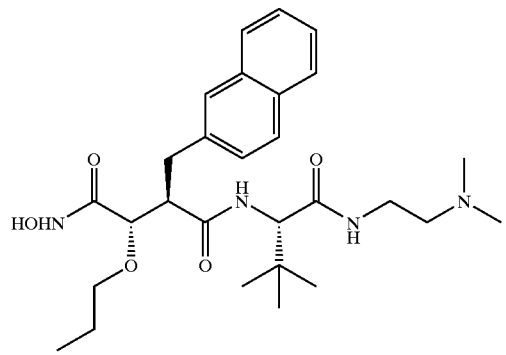

MS (ES+ve) M+H=514

¹H NMR (DMSO-d₆) 0.82 (3H, t, J=7.5 Hz), 0.84 (9H, s), 1.45 (2H, m), 2.01 (6H, s), 2.59 (1H, m), 2.64 (1H, dd), 2.74 (1H, m), 2.84 (1H, dd), 3.20 (2H, m), 3.77 (1H, d, J=9.5 Hz), 4.05 (1H, d, J=9.5 Hz), 7.23 (2H, m), 7.43 (2H, m), 7.58 (2H, m), 7.77 (3H, m), 9.10 (1H, s), 10.90 (1H, s).

EXAMPLE 67

N'-[4-(N-Hydroxyamino)-3S-propoxy-2R-(2-naphthylmethyl)succinyl]-R-tert-leucine (N,N-dimethylaminoeth-2-yl)amide

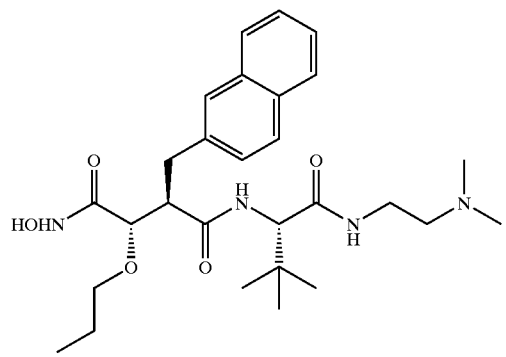

MS (ES+ve) M+H=514

¹H NMR (DMSO-d₆) 0.33 (9H, s), 0.76 (3H, t, J=7.5 Hz), 1.37 (2H, m), 2.12 (6H, s), 2.70 (1H, dd), 2.77 (1H, dd, J=13.5,12 Hz), 3.10 (4H, m), 3.51 (1H, m), 3.72 (1H, d, J=10 Hz), 4.00 (1H, d, J=9.5 Hz), 7.35 (1H, d, J=8.5 Hz), 7.41 (2H, m), 7.64 (1H, d, J=9.5 Hz), 7.70 (1H, s), 7.77 (4H, m), 9.09 (1H, s), 10.92 (1H, s).

EXAMPLE 68

N'-[4-(N-Hydroxyamino)-3S-ethoxy-2R-(2-naphthylmethyl)succinyl]-S-(O-benzyl) tert-leucinol

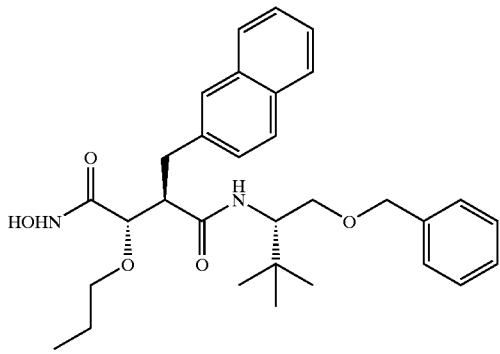

MS (ES+ve) M+H 521

$^1$H NMR (DMSO-d$_6$) 0.79 (9H, s), 0.82 (3H, t), 1.42 (2H, m), 2.63 (2H, m), 2.82 (2H, m), 3.19 (2H, m), 3.29 (1H, t), 3.64 (1H, m), 3.70 (2H, d, J=7 Hz), 3.79 (1H, d, J=10 Hz), 6.99 (1H, d, J=6.5 Hz), 7.25 (4H, m), 7.42 (3H, m), 7.60 (1H, s), 7.68 (1H, d, J=8.5 Hz), 7.79 (2H, m), 9.10 (1H, s), 10.97 (1H, s).

EXAMPLE 69

N'-[4-(N-Hydroxyamino)-3S-propoxy-2R-[S-1-(1,2,3,4-tetrahydronaphthalen-2-yl)methyl)succinyl]-S-tert-leucine methylamide

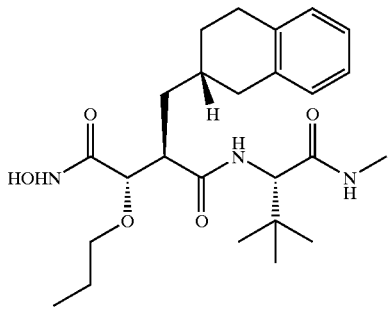

i) 2R-1,2,3,4-Tetrahydronaphthalene-2-methyl alcohol

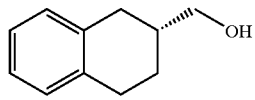

2R-1,2,3,4-Tetrahydronaphthoic acid (2.26 g, 12.84 mmol) (prepared as described by Charlton et al, Synlett. (1990), 333) in dry THF (35 ml) at 0–5° C. was treated with a 1M soln. of LiAlH$_4$ in THF (12.85 ml) and the resulting mixture was stirred at 0–5° C. for 0.25 h followed by 1 h at room temperature. The reaction mixture was then treated with water (1 ml), 2M NaOH soln. (1 ml) and water (1 ml) and then filtered through celite. The filtrate was evaporated to dryness and the residue partitioned between diethyl ether and dil. NaHCO$_3$ soln. The ether layer was separated, washed with dil NaHCO$_3$ soln.(×3) and brine (×1), and then dried over MgSO$_4$. It was filtered and evaporated to dryness. The crude product was purified by chromatography on silica gel to afford the title compound 1.51 g.

$^1$H NMR (CDCl$_3$) 1.45 (2H, m), 1.97 (2H, m), 2.50 (1H, dd, J=10.5, 16.5 Hz), 2.87 (3H, m), 3.64 (2H, br.s), 7.09 (4H, m). [α]+88.2 (c=0.53, CHCl$_3$)

ii) Trifluoromethane sulfonic acid [(R)-1-(1,2,3,4-tetrahydonaphthalen-2-yl)methyl]ester

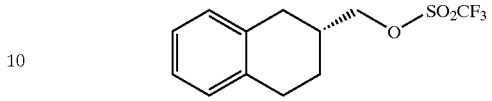

The alcohol (1.47 g, 9.07 mmol) and pyridine (0.72 g, 9.07 mmol) in dry dichloromethane (20 ml) were added dropwise to a solution of triflic anhydride (2.56 g, 9.07 mmol) in dichloromethane at 0–5° C. The resulting mixture was stirred at that temperature for 2 h before being washed with cold, dil. H$_2$SO$_4$ (×3), cold, dil. NaHCO$_3$ soln (×3) and brine (×1). The organic soln. was dried over MgSO$_4$, filtered and evaporated to yield the title compound as a golden oil (2.56 g).

$^1$H NMR (CDCl$_3$) 1.55 (1H, m), 2.05 (1H, m), 2.35 (1H, m), 2.60 (1H, dd, J=10.5, 16.5 Hz), 2.88 (3H, m), 4.48 (1H, d, J=9.5 Hz), 4.53 (1H, d, J=9.5 Hz), 7.14 (4H, m).

iii) Diethyl (2R,3S)-3-hydroxy-2-[(S)-1-(1,2,3,4-tetrahydronaphthalen-2-yl)methyl]succinate

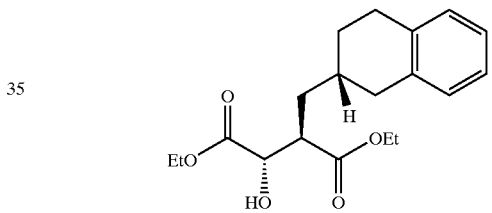

S-Diethyl malate (2.94 g, 15.3 mmol) in dry THF (25 ml) was added dropwise to a 1M soln. of LHMDS in THF (33.7 ml) at −70° C. under argon keeping the temperature below −50° C. during the addition. The solution was stirred at −70° C. for 2 h and then a solution of the above triflate (15.3 mmol) in dry THF (20 ml) was added slowly dropwise keeping the temperature below −60° C. The reaction solution was then stirred at −70° C. to room temperature for 18 h and then it was poured into cold, dilute HCl and the product was extracted with diethyl ether (×3). The combined extracts were washed with dil HCl (×1), satd. NaHCO3 soln. (×3) and brine (×1) before being dried with MgSO$_4$, filtered and evaporated to leave the crude product. Chromatography on silica afforded the pure title compound (2.11 g).

MS (ES+ve) M+Na 357

$^1$H NMR (CDCl$_3$) 1.24 (3H, t, J=7.0 Hz), 1.32 (3H, t, J=7.0 Hz), 1.45 (1H, m), 1.67 (1H, m), 1.83 (1H, m), 1.97 (1H, m), 2.45 (1H, dd, J=10, 16 Hz), 2.82 (2H, m), 2.93 (1H, dd, J=4, 16 Hz), 3.18 (1H, d, J=7.5 Hz), 4.13 (2H, m), 4.27 (3H, m), 7.08 (4H, m).

iv) Diethyl (2R,3S)-3-allyloxy-2-[(S)-1-(1,2,3,4-tetrahydronaphthalen-2-yl)methyl]succinate

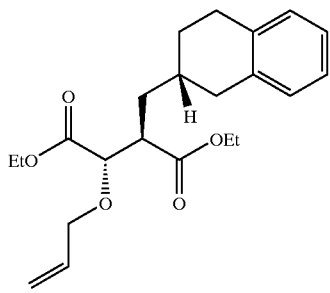

The alcohol from (iii) above (1.62 g, 4.85 mmol) and allyl bromide (5.87 g, 48.5 mmol) in dry DMF (15 ml) were treated with 60% NaH in oil (0.233 g, 5.82 mmol) and the mixture was stirred at room temperature for 1.25 h. Satd. NH$_4$Cl soln. was then added and the mixture was evaporated to near dryness. The residue was partitioned between diethyl ether and water and the organic layer was separated and washed with dil HCl (×4) and brine (×1). The soln was dried (MgSO$_4$), filtered and evaporated to leave an orange oil. This was purified on silica to afford the title compound (1.61 g).

MS (ES+ve) M+H=375

$^1$H NMR (CDCl$_3$) 1.26 (6H, m), 1.38 (2H, m), 1.71 (1H, m), 1.86 (2H, m), 2.37 (1H, dd), 2.79 (2H, m), 2.96 (1H, dd), 3.07 (1H, m), 3.93 (1H, dd, J=6, 12.5 Hz), 4.07 (1H, d, J=8 Hz), 4.17 (5H, m), 5.18 (1H, dd, J=1, 10.5 Hz), 5.25 (1H, dd, J=1, 15.5 Hz), 5.85 (1H, m), 7.07 (4H, m).

v) Diethyl (2R,3S)-3-propoxy-2-[(S)-1-(1,2,3,4-tetrahydronaphthalen-2-yl)methyl]succinate

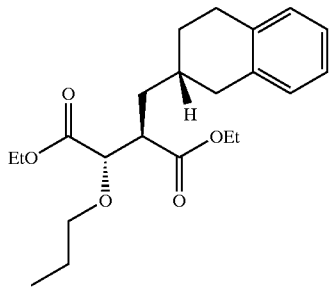

The O-allyl derivative from (iv) above (1.61 g, 4.30 mmol) in methanol (30 ml) was hydrogenated at atmospheric pressure over 10% Pd/C (500 mg) for 2 h. The catalyst was filtered and the filtrate evaporated to dryness to afford the title compound as a colourless oil (1.56 g).

MS (ES+ve) M+H=377

$^1$H NMR (CDCl$_3$) 0.89 (3H, t, J=7.5 Hz), 1.26 (6H, m), 1.38 (2H, m), 1.58 (2H, m), 1.70 (1H, m), 1.83 (2H, m), 2.35 (1H, dd), 2.78 (2H, m), 2.95 (1H, dd), 3.03 (1H, m), 3.30 (1H, m), 3.53 (1H, m), 3.99 (1H, d, J=8.5 Hz), 4.17 (4H, m), 7.06 (4H, m).

vi) (2R,3S)-3-Propoxy-2-[(S)-1-(1,2,3,4-tetrahydronaphthalen-2-yl)methyl]succinic acid

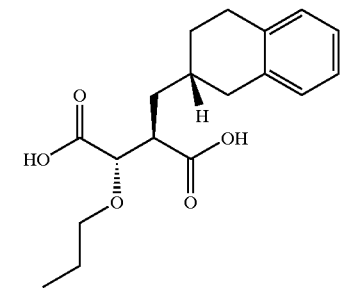

The diethyl ester from (v) above (1.54 g, 4.1 mmol) in dioxane (12 ml) was treated with 2M KOH soln. (6.15 ml) and the mixture was stirred at room temperature for 22.5 h followed by 3 h at 80° C. The soln. was evaporated to dryness and the resulting residue was dissolved in water and washed with ethyl acetate. The aqueous soln. was then saturated with NaCl and the pH adjusted to 1 with dil HCl. The product was extracted into ethyl acetate (×3) and the combined extracts were washed with brine (×1), dried (MgSO$_4$), filtered and evaporated to afford the title compound as a white solid (1.35 g).

MS (ES−ve) M−H=319

$^1$H NMR (DMSO-d$_6$) 0.84 (3H, t, J=7.5 Hz), 1.33 (2H, m), 1.47 (2H, m), 1.67 (2H, m), 1.82 (1H, m), 2.30 (1H, dd), 2.67–2.91 (4H, m), 3.25 (1H, m), 3.48 (1H, m), 3.85 (1H, d, J=8 Hz), 7.05 (4H, m), 12.20–13.00 (2H, v.br.s).

vii) (2R,3S)-3-Propoxy-2-[(S)-1-(1,2,3,4-tetrahydronaphthalen-2-yl)methyl]succinic acid 4-methyl ester

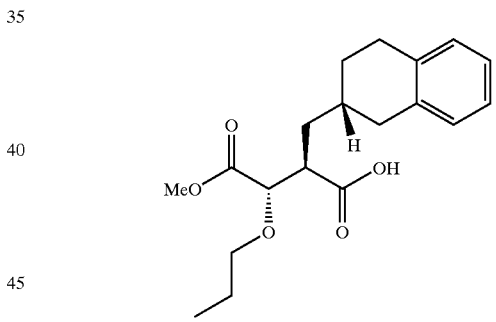

The di-acid from (vi) above (1.3 g, 4.1 mmol) in dry dichloromethane (15 ml) was cooled in an ice bath and treated with trifluoroacetic anhydride (8 ml). The resulting solution was stirred at 0–5° c. for 10 mins followed by 2 h at room temperature. The solution was then evaporated to dryness to leave the corresponding anhydride as a colourless oil ($v_{max}$ 1788 cm$^{-1}$). This was dissolved in methanol (20 ml) and stirred at room temperature for 16 h. Evaporation of the solvent afforded the title compound as a pale yellow oil (1.43 g).

MS (ES−ve) M−H=333

$^1$H NMR (CDCl$_3$) 0.90 (3H, t, J=7.5 Hz), 1.44 (2H, m), 1.62 (2H, m), 1.77–1.96 (3H, m), 2.40 (1H, dd), 2.80 (2H, m), 2.97 (1H, dd), 3.10 (1H, m), 3.34 (1H, m), 3.71 (1H, m), 3,76 (3H, s), 4.03 (1H, d, J=7.5 Hz), 7.07 (4H, m).

viii) N'-[4-Methoxy-3S-propoxy-2R-[S-1-(1,2,3,4-tetrahydronaphthalen-2-yl)methyl)succinyl]-S-tert-leucine methylamide

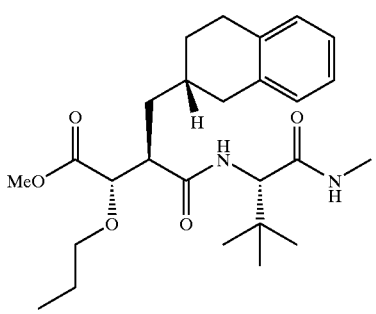

A solution of the acid from (vii) above (1.43 g, 4.28 mmol) in dry DMF (15 ml) was treated with HOBt (1.16 g, 8.56 mmol) and EDC (1.64 g, 8.56 mmol) and the resulting soln. was stirred at room temperature for 10 mins. S-tert-leucine methylamide hydrochloride (0.85 g, 4.71 mmol) was the added followed by DIPEA (0.66 g, 5.14 mmol) and the reaction solution was stirred at room temperature for 1.25 h. It was then evaporated to dryness and the residue was partitioned between EtOAc and dil. HCl. The organic layer was separated and washed with dil. HCl (×3), dil. NaHCO$_3$ (×3) and brine (×1). It was dried (MgSO$_4$) and evaporated to leave the crude product which was purified on silica to afford the title compound (1.44 g).

MS (ES+ve) M+H=461

$^1$H NMR (CDCl$_3$) 0.96 (3H, t, J=7.5 Hz), 1.03 (9H, s), 1.32–1.74 (5H, m), 1.88 (2H, m), 2.42 (1H, dd), 2.73 (3H, d, J=5 Hz), 2.76–3.00 (5H, m), 3.3 (1H, m), 3.62 (1H, m), 3.77 (3H, s), 3.99 (1H, d. J=5 Hz), 4.09 (1H, d, J=9 Hz), 6.29 (1H, m), 7.03 (5H, m).

ix) N'-[4-Hydroxy-3S-propoxy-2R-]S-1-(1,2,3,4-tetrahydronaphthalen-2-yl)methyl)succinyl]-S-tert-leucine methylamide

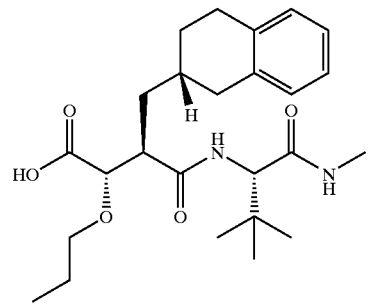

A soln. of the ester from (viii) above (0.68 g) in dioxane (12 ml) was treated dropwise with a soln. of LiOH.H$_2$O (0.124 g) in water (5 ml). The resulting soln. was stirred at room temperature for 1.75 h and then it was evaporated to near dryness. The residue was partitioned between water and EtOAc and the aqueous phase was separated and washed with EtOAc (×1) before being satd. with NaCl, acidified to pH 1, and extracted with EtOAc (×3). The combined extracts were washed with brine (×1), dried (MgSO$_4$) and evaporated to afford the product as a white solid (0.63 g).

MS (ES+ve) M+H=447

$^1$H NMR (DMSO-d$_6$) 0.82 (3H, t, J=7.5 Hz), 0.90 (9H, s), 1.22 (2H, m), 1.40–1.61 (4H, m), 1.73 (1H, m), 2.24 (1H, dd, J=10, 16 Hz), 2.40 (3H, d, J=4.5 Hz), 2.67 (2H, m), 2.95 (2H, m), 3.21 (1H, m), 3.38 (1H, m, obscured by water), 3.78 (1H, d, J=9 Hz), 4.18 (1H, d. J=9.5 Hz), 7.01 (4H, m), 7.71 (1H, q, J=4.5 Hz), 7.90 (1H, d, J=9.5 Hz), 12.84 (1H, br.s).

x) N'-[4-(N-Hydroxyamino)-3S-propoxy-2R-[S-1-(1,2,3,4-tetrahydronaphthalen-2-yl)methyl)succinyl]-S-tert-leucine methylamide

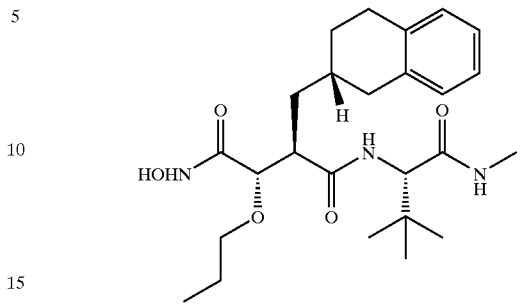

A soln. of the acid from (ix) above (0.61 g) in dry DMF (10 ml) was treated with HOAt (0.372 g) and EDC (0.524 g) and stirred at room temperature for 10 mins. Hydroxylamine hydrochloride (0.285 g) and NMM (0.414 g) were then added and the reaction mixture was stirred at room temperature for 2 h. It was then evaporated to dryness and the residue was partitioned between EtOAc and dil.HCl. The organic phase was separated and washed with dil HCl, dil. NaHCO$_3$ and water and then evaporated to dryness to leave a white solid. This was triturated with diethyl ether then filtered and dried in vacuo to afford the title compound (0.434 g).

MS (ES+ve) M+H=462

$^1$H NMR (DMSO-d$_6$) 0.80 (3H, t, J=7.5 Hz), 0.90 (9H, s), 1.08 (1H, m), 1.23 (1H, m), 1.45 (4H, m), 1.70 (1H, m), 2.19 (1H, dd), 2,35 (3H, d, J=4.5 Hz), 2.65 (2H, m), 2.97 (2H, m), 3.14 (1H, m), 3.27 (1H, m), 3.63 (1H, d, J=9.5 Hz), 4.18 (1H, d, J=9.5 Hz), 7.02 (4H, m), 7.59 (1H, q, J=4.5 Hz), 7.83 (1H, d, J=9.5 Hz), 9.02 (1H, s), 10.78 (1H, s).

EXAMPLE 70

N'-[3S-(Ethoxy)-4-(N-hydroxyamino)-2R-(2-quinolinylmethyl)succinyl]-S-tert-leucine ethylamide

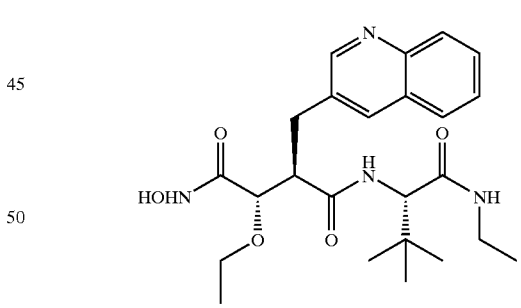

5% Pd-BaSO$_4$ (50 mg) was added to a solution of N'-[4-(N-Benzyloxyamino)-3S-(ethoxy)-2R-(2-quinolinylmethyl)succinyl]-S-tert-leucine ethylamide(0.17 g, 0.3 mmol) in methanol (15 ml) and cyclohexene (5 ml) under argon. The mixture was heated at reflux for 6 hours then cooled and filtered through a celite plug. The filtrate was evaporated to give a solid which was triturated with ether (3×2 ml) to afford the title compound as a white solid (0.13 g, 0.28 mmol, 92%).

MS (ES+ve) [M+H]$^+$=459

$^1$H NMR (DMSO-d$_6$): 0.66 (3H, t J=7.2 Hz), 0.83 (9H, s), 1.04 (3H, t, J=7.0 Hz), 2.58 (2H, m), 2.70 (1H, m), 2.84 (2H, m), 3.39 (2H, m), 3.81 (1H, d, J=9.7 Hz), 4.05 (1H, d, J=9.6 Hz), 7.35 (H, t, J=5.3 Hz), 7.55 (1H, t, J=7.4 Hz), 7.68 (1H, d, J=8.5 Hz), 7.70 (1H, d, J=10.4 Hz), 7.83 (1H, d, J=7.6 Hz), 7.94 (1H, d, 7.9 Hz), 7.97 (1H, s), 8.60 (1H, d, H=2 Hz), 9.11 (1H, s), 10.96 (1H, s).

EXAMPLE 71

N'-[4-(N-Hydroxyamino)-3S-(propoxy)-2R-(2-quinolinylmethyl)succinyl]-S-tert-leucine ethylamide

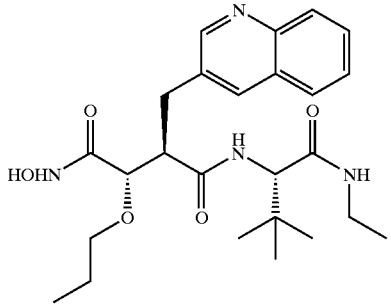

5% Pd-BaSO$_4$ (50 mg) was added to a solution of N'-[4-(N-Benzyloxyamino)-3S-(propoxy)-2R-(2-quinolinylmethyl)succinyl]-S-tert-leucine ethylamide (0.12 g, 0.21 mmol) in methanol (15 ml). The mixture was stirred under a hydrogen atmosphere for 48 hours then filtered through a celite plug. The filtrate was evaporated to give a solid which was triturated with ether (3×2 ml) to afford the title compound as a white solid (0.05 g, 0.11 mmol, 54%).

MS (ES+ve) [M+H]$^+$=473

$^1$H NMR (DMSO-d$_6$): 0.66 (3H, t J=7.2 Hz), 0.81 (3H, t, J=7.0 Hz), 0.83 (9H, s), 1.43 (2H, m), 2.58 (2H, m), 2.70 (1H, m), 2.84 (2H, m), 3.39 (2H, m), 3.81 (1H, d, J=9.7 Hz), 4.05 (1H, d, J=9.6 Hz), 7.35 (1H, t, J=5.3 Hz), 7.55 (1H, t, J=7.4Hz), 7.68 (1H, d, J=8.5 Hz), 7.70 (1H, d, J=10.4 Hz), 7.83 (1H, d, J=7.6 Hz), 7.94 (1H, d, 7.9 Hz), 7.97 (1H, s), 8.60 (1H, d, H=2 Hz), 9.11 (1H, s), 10.96 (1H, s).

EXAMPLE 72

N'-[3S-(Ethoxy)-2R-(2-(6-fluoro-)naphthylmethyl)-4-(N-hydroxyamino)succinyl]-S-tert-leucine ethylamide

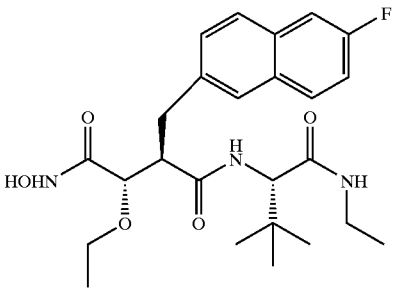

5% Pd-BaSO$_4$ (50 mg) was added to a solution of N'-[4-(N-Benzyloxyamino)-3S-(ethoxy)-2R-(2-(6-fluoro) naphthylmethyl)succinyl]-S-tert-leucine ethylamide (0.17 g, 0.3 mmol) in methanol (15 ml) and cyclohexene (5 ml) under argon. The mixture was heated at reflux for 4 hours then cooled and filtered through a celite plug. The filtrate was evaporated to give a solid which was triturated with ether (3×2 ml) to afford the title compound as a white solid (0.12 g, 0.26 mmol, 62%).

MS (ES+ve) [M+H]$^+$=476

$^1$H NMR (DMSO-d$_6$): 1.04 (9H, s), 1.21 (3H. t. J=7.0 Hz), 1.43 (3H, t, J=6.6 Hz), 3.08 (2H, m), 3.41 (2H, m), 3.48 (2H, q, J=7.0 Hz), 3.64 (1H, d, J=2.8 Hz), 3.82 (1H, t, J=7.2 Hz), 4.00 (1H, d, J=9.1 Hz), 7.14 (1H, m), 7.22 (1H, m), 7.43 (2H, m), 7.71 (4H, m), 7.96 (1H, d, J=10.5 Hz), 9.51 (1H, br s).

EXAMPLE 73

N'-[4-(N-Hydroxyamino)-3S-allyloxy-2R-(2-naphthylmethyl)succinyl]-S-tert-leucine methyl ester

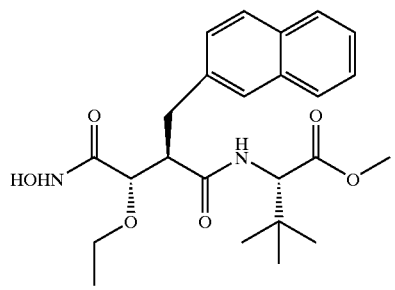

Prepared analogously to example 64.

MS (ES+ve) [M+H]$^+$=445

$^1$H NMR (DMSO-d$_6$): 0.84 (9H,s), 1.01 (3H. t. J=7 Hz), 2.68 (1H, dd, J=13.5,4 Hz), 2.73–2.83 (1H, m), 3.20–3.79 (3H, m), 3.27 (3H, s), 3.77 (1H, d, J=10 Hz), 4.15 (1H, d, J=9 Hz), 7.21 (1H, dd, J=8, 1.5 Hz), 7.40–7.46 (2H, m), 7.55 (1H, s), 7.74 (1H, d, J=9 Hz), 7.75–7.81 (2H, m), 7.90 (1H, d, J=9 Hz), 9.09 1H, d, J=0.5 Hz), 10.96 (1H, d, J=0.5 Hz).

EXAMPLE 74

N'-[4-(N-Hydroxyamino)-2R-(2-naphthylmethyl)-3S-propoxy succinyl]-S-tert-leucine isopropylamide

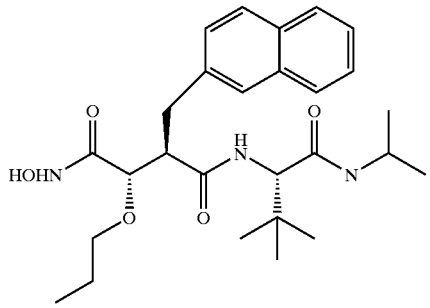

Prepared analogously to example 1 from N-[4-t-Butoxy-3S-(hydroxy)-2R-(2-naphthylmethyl)succinyl]-S-tert-leucine isopropylamide by alkylation with allyl bromide, hydrogenation, tert butyl ester cleavage and hydroxamic acid formation.

MS (ES–ve) [M–H]$^+$=484

$^1$H NMR (DMSO-d$_6$): 0.72 (3H, d, J=6.5 Hz), 0.75 (3H, d, J=6.5 Hz), 0.82 (3H, t, J=7.5 Hz), 0.84 (9H,s), 1.40–1.51 (2H, m), 2.64 (1H, dd, J=13,3 Hz), 2.77–2.91 (1H, m), 3.18–3.7 (3H, m), 3.44–3.50 (1H, m), 3.77 (1H, d, J=10 Hz), 4.06 (1H, d, J=10 Hz), 7.24 (1H, dd, J=8, 1.5 Hz), 7.36–7.44 (3H, m), 7.53 (1H, d, J=10 Hz), 7.55 (1H, s), 7.70 (1H, d, J=8.5 Hz), 7.72–7.79 (2H, m), 9.09 1H, s), 10.89 (1H, s).

EXAMPLE 75

N'-[3S-Ethoxy-4-(N-hydroxyamino)-2R-(2-naphthylmethyl)succinyl]-S-tert-leucine isopropylamide

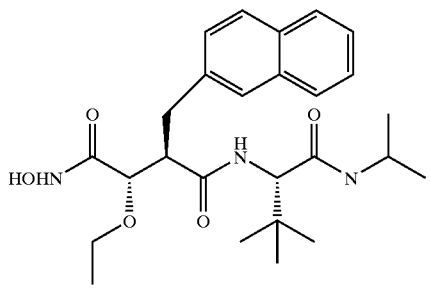

Prepared analogously to example 1 from N-[4-t-Butoxy-3S-(hydroxy)-2R-(2-naphthylmethyl)succinyl]-S-tert-leucine isopropylamide by alkylation with iodoethane, tert butyl ester cleavage and hydroxamic acid formation.

MS (ES–ve) [M–H]$^+$=470

$^1$H NMR (DMSO-d$_6$): 0.72 (3H, d, J=6.5 Hz), 0.76 (3H, d, J=6.5 Hz), 0.84 (9H,s), 1.05 (3H, t, J=7 Hz), 2.63 (1H, dd, J=13,3 Hz), 2.80–2.91 (1H, m), 3.17–3.27 (2H, m), 3.41–3.51 (2H, m), 3.76 (1H, d, J=10 Hz), 4.08 (1H, d, J=10 Hz), 7.24 (1H, dd, J=8, 1.5 Hz), 7.39–7.44 (3H, m), 7.53 (1H, d, J=10 Hz), 7.55 (1H, s), 7.69 (1H, d, J=8 Hz), 7.71–7.78 (2H, m), 9.08 1H, s), 10.89 (1H, s).

EXAMPLE 76

N'-[3S-Ethoxy-4-(N-hydroxyamino)-2R-(2-naphthylmethyl)succinyl]-S-tert-leucine (2,2,2-trifluoroethyl)amide

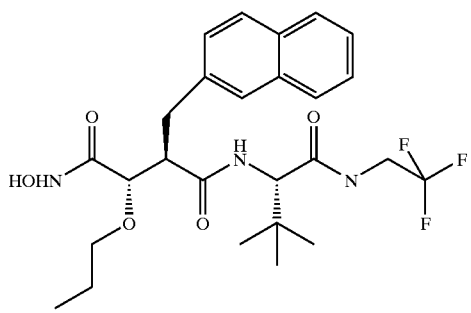

Prepared analogously to example 1 from N-[4-t-Butoxy-3S-(hydroxy)-2R-(2-naphthylmethyl)succinyl]-S-tert-leucine-(2,2,2-trifluoroethyl)amide by alkylation with allyl bromide, hydrogenation, tert butyl ester cleavage and hydroxamic acid formation.

MS (ES–ve) [M–H]$^+$=524

$^1$H NMR (DMSO-d$_6$): 0.81 (3H, t, J=7.5 Hz), 0.83 (9H,s), 1.41–1.47 (2H, m), 2.62–2.67 (1H, m), 2.81 (1H, app t, J=13.5 Hz), 3.17–3.80 (5H, m), 3.79 (1H, d, J=9.5 Hz), 4.17 (1H, d, J=9.5 Hz), 7.22 (1H, dd, J=10, 1.5 Hz), 7.42–7.46 (2H, m), 7.53 (1H, s), 7.55 (1H, s), 7.63 (1H, d, J=9.5 Hz), 7.72 (1H, d, J=8.5 Hz), 7.76 (1H, d, J=8.5 Hz), 7.83 (1H, d, J=8.5 Hz), 8.06 (1H, app t, J=6 Hz), 9.09 1H, s), 10.92 (1H, s).

EXAMPLE 77

N'-[3S-Ethoxy-4-(N-hydroxyamino)-2R-(2-naphthylmethyl)succinyl]-S-tert-leucine(2,2,2-trifluoroethyl)amide

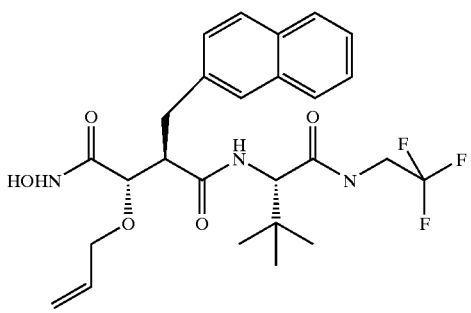

Prepared analogously to example 1 from N-[4-t-Butoxy-3S-(hydroxy)-2R-(2-naphthylmethyl)succinyl]-S-tert-leucine-(2,2,2-trifluoroethyl)amide by alkylation with allyl bromide, tert butyl ester cleavage and hydroxamic acid formation.

MS (ES–ve) [M–H]$^+$=522

$^1$H NMR (DMSO-d$_6$): 0.81 (9H,s), 2.64–2.74 (2H, m), 3.24–3.31 (3H, m), 3.78 (1H, dd, J=8,3.5 Hz), 3.86 (1H, d, J=6 Hz), 3.95 (1H, dd, J=8,3.5 Hz), 4.19 (1H, d, J=6 Hz), 5.07–5.24 (2H, m), 5.74–5.81 (1H, m), 7.22 (1H, d, J=5 Hz), 7.41–7.46 (2H, m), 7.53 (1H, s), 7.66–7.84 (4H, m), 8.12 (1H, t, J=4 Hz), 9.11 1H, s), 10.92 (1H, s).

EXAMPLE 78

N'-[4-(N-Hydroxyamino)-3S-propoxy-2R-[S or R-1-(1,2,3,4-tetrahydronaphthalen-2-yl)methyl)succinyl]-S-tert-leucinamide

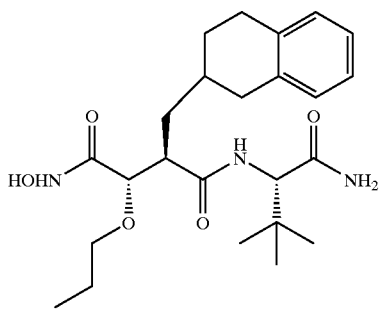

MS (ES–ve) [M–H]$^+$=446

EXAMPLE 79

N'-[2R-(2-(6-Fluoronaphthyl)methyl)-4-(N-hydroxyamino)-3S-propoxysuccinyl]-S-tert-leucine ethylamide

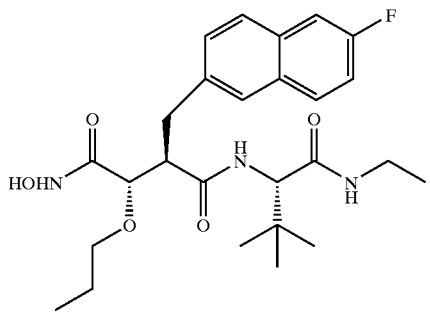

Prepared analogously to example 1d)+e) from 2R-(2-(6-Fluoro)naphthylmethyl)-3S-hydroxy succinic acid diethyl ester, alkylating using allyl bromide.

MS (ES+ve) M+H=490, M+Na=512.

$^1$H NMR (DMSO-d$_6$): 0.67 (3H, t, J=7 Hz). 0.81 (3H, t, J=7.5 Hz), 0.84 (9H, s), 1.45 (2H, sextet. J=7 Hz), 2.53–2.68 (3H, m), 2.82 (1H, m), 3.16–3.25 (3H 3.77 (1H, d, J=9.5 Hz), 4.02 (1H, d, J=9.5 Hz), 7.26–7.30 (2H, m), 7.35 (1H, m), 7.55–7.62 (2H, m), 7.61 (1H, s), 7.72 (1H, d, J=8.5 Hz), 7.85 (1H, m), 9.09 (1H, br. s), 10.86 (1H, br. s).

EXAMPLE 80

N'-[3S-Ethoxy-4-(N-hydroxyamino)-2R-(2-naphthylmethyl)succinyl]-S-tert-leucine cyclopropylamide

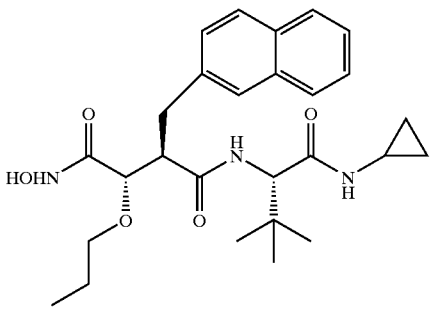

Prepared analogously to example 1 from N-[4-t-Butoxy-3S-(hydroxy)-2R-(2-naphthylmethyl)succinyl]-S-tert-leucine cyclopropylamide by alkylation with allyl bromide, hydrogenation, tert butyl ester cleavage and hydroxamic acid formation.

MS (ES+ve) M+H=470, M+Na=492.

$^1$H NMR (DMSO-d$_6$): 0.06 (2H, m), 0.42 (2H, m), 0.83 (9H, s), 1.05 (3H, t, J=7 Hz), 2.20 (1H, m), 2.63 (1H, dd, J=14, 3.5 Hz), 2.87 (1H, dd, J=14, 11 Hz), 3.19 (1H, m), ca. 3.28 & 3.44 (2H, 2×m, partially obscured by H$_2$O signal), 3.76 (1H, d. J=9.5 Hz), 4.05 (1H, d, J=9.5 Hz), 7.23 (1H, dd, J=8.5, 1.5 Hz), 7.42 (2H, m), 7.55 (1H, s), 7.59 (1H, d, J=9.5 Hz), 7.72 (1H, d, J=8.5 Hz), 7.80 (2H, m), 9.09 (1H, br. s), 10.88 (1H, br. s).

EXAMPLE 81

N'-[3S-tert-Butoxy-4-(N-hydroxyamino)-2R-(2-naphthylmethyl)succinyl]-S-tert-leucinamide

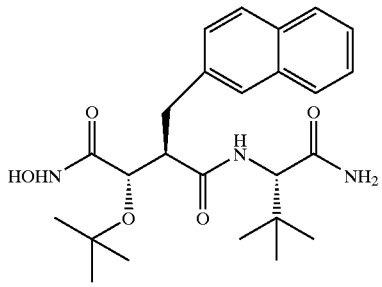

Prepared analogously to example 34.

MS (ES+ve) M+H=458, M+Na=480.

$^1$H NMR (DMSO-d$_6$): 0.90 (9H, s), 1.12 (9H, s), 2.73 (1H, dd, J=14, 3.5 Hz), 2.90 (1H, dd, J=14, 11 Hz), 3.04 (1H, m), 3.99 (1H, d, J=9,5 Hz), 4.01 (1H, d, J=9 Hz), 6.63 (1H, br. s), 6.83 (1H, br. s), 7.26 (1H, dd, J=8.5, 1.5 Hz), 7.43 (2H, m), 7.55 (1H, d, J=9 Hz), 7.59 (1H, s), 7.74 (1H, d, J=8.5 Hz), 7.81 (2H, m), 8.95 (1H, br. s), 10.71 (1H, br. s).

EXAMPLE 82

N'-[4-(N-Hydroxyamino)-3S-(1,2,4-oxadiazol-3-yl) methoxy)-2R-(2-naphthylmethyl)succinyl]-S-tert-leucine methylamide

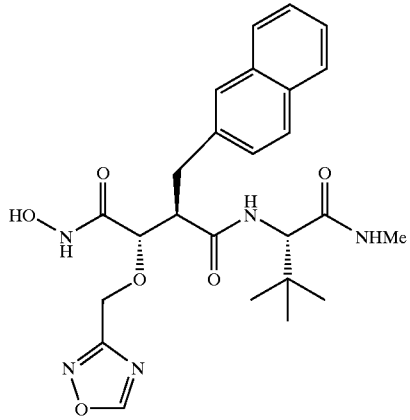

MS (ES+ve) M+Na=520, M+H=498

MS (ES−ve) M−H=496

$^1$H NMR (DMSO-d$_6$): 0.70 (9H, s), 2.04 (3H, d, J=4.5 Hz), 2.67 (1H, m), 2.84 (1H, dd, J=11.2, 13.6 Hz), 3.36 (1H, m), 3.98 (1H, d, J=9.5 Hz), 4.04 (1H d, J=10.9 Hz), 4.48 (1H, d, J=12.3 Hz), 4.63 (1H, d, J=12.3 Hz), 6.99 (1H, q, J=4.4 Hz), 7.24 (1H, d, J=8.4 Hz), 7.44 (2H, m), 7.57 (1H, s), 7.63 (1H, d, J=8.5 Hz), 7.73 (1H, d, J=8.5 Hz), 7.78 (1H, d, J=8.3 Hz), 7.84 (1H, d, J=8.3 Hz), 9.20 (1H, s), 9.58 (1H, s), 11.05 (1H, s).

EXAMPLE 83

N'-[4-(N-Hydroxyamino)-3S-(2-thiazolylmethoxy)-2R-(2-naphthylmethyl)succinyl]-S-tert-leucine methylamide

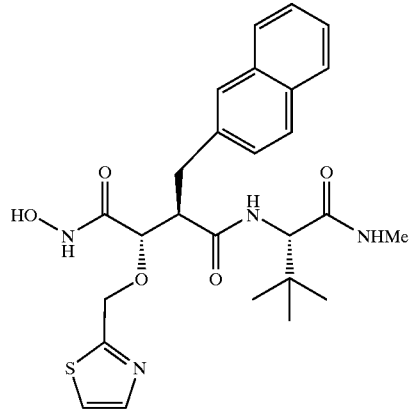

MS (ES+ve) M+Na=535, M+H=512

MS(ES−ve) M−H=511

¹H NMR (DMSO-d₆): 0.74 (9H, s), 2.04 (3H, d, J=4.5 Hz), 2.70 (1H, m), 2.84 (1H, t, J=13.5 Hz), 3.36 (1H, m), 4.01 (1H, d, J=9.4 Hz), 4.07 (1H, d, J=9.8 Hz), 4.65 (1H, d, J=12.9 Hz), 4.77 (1H, d, J=12.8 Hz), 7.04 (1H, d, J=4.7 Hz), 7.27 (1H, d, J=8.4 Hz), 7.44 (2H, m), 7.58 (1H, s), 7.74 (4H, m), 7.78 (1H. d, J=8.3 Hz), 7.83 (1H, d, J=8.3 Hz), 9.20 (1H, s), 11.05 (1H, s).

EXAMPLE 84

N'-[2R-(4-Benzocycloheptyl)methyl-4-(N-hydroxyamino)-3S-(propoxy)succinyl]-S-tert-leucine methylamide

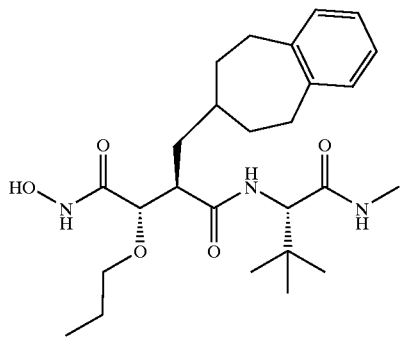

MS (ES+ve) M+H=476, M+Na=498

MS (ES−ve) M−H=474

¹H NMR (DMSO-d₆): 0.79 (3H, t, J=7.3 Hz), 0.93 (9H, s), 1.32–1.45 (3H, m), 1.70 (1H, m), 2.05 (1H, m), 2.45–2.56 (4H, m), 2.58–2.67 (7H, m), 2.91 (1H, m), 3.11 (1H, m), 3.26 (1H, m), 3.59. (1H, d, J=9.6 Hz), 4.24 (1H, d, J=9.5 Hz), 7.04 (4H, m), 7.76 (1H, d, J=9.5 Hz), 7.82 (1H, d, J=4.5 Hz), 8.97 (1H, s), 10.72 (1H, s).

EXAMPLE 85

N'-[2R-(3-Benzocyclopentyl)methyl-4-(N-hydroxyamino)-3S-(propoxy)succinyl]-S-tert-leucine methylamide

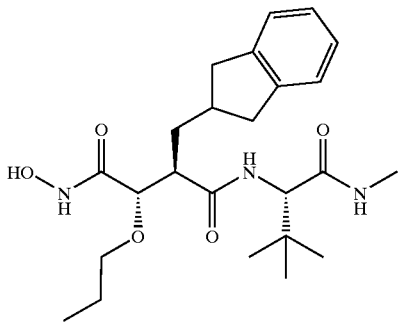

MS (ES+ve) M+H=448, M+Na=470

MS (ES−ve) M−H=446

¹H NMR (DMSO-d₆): 0.79 (3H, t, J=7.4 Hz), 0.92 (9H, s), 1.25 (1H, m), 1.42 (2H, m), 1.56 (1H, m), 2.20 (1H, m), 2.34 (1H, m), 2.50 (4H, m), 2.88 (2H, m), 3.00 (1H, m), 3.13 (1H, m), 3.27 (1H, m), 3.63. (1H, d, J=9.8 Hz), 4.23 (1H, d, J=9.5 Hz), 7.06 (3H, m), 7.14 (1H, d, J=3.6 Hz), 7.83 (2H, m), 9.00 (1H, s), 10.78(1H, s).

EXAMPLE 86

N'-[2R-(3-Benzocyclopentyl)methyl-4-(4-hydroxyamino)-3S-(propoxy)succinyl]-S-tert-leucine methoxyamide

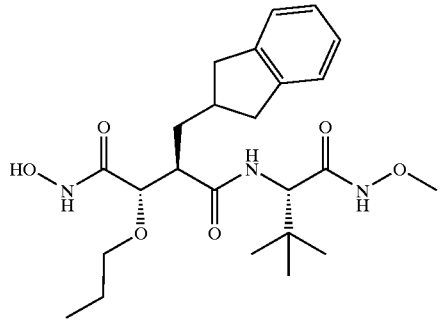

MS (ES+ve) M+H=464, M+Na=486

MS (ES−ve) M−H=462

¹H NMR (DMSO-d₆): 0.78 (3H, t, J=7.4 Hz), 0.94 (9H, s), 1.23 (1H, m), 1.41 (2H, m), 1.55 (1H, m), 2.20 (1H, m), 2.36 (1H, m), 2.47 (1H, m), 2.88 (1H, m), 2.93–3.08 (2H, m), 3.12 (1H, m), 3.26 (1H, m), 3.45 (3H, s), 3.63 (1H, d, J=9.9 Hz), 4.09 (1H, d, J=9.4 Hz), 7.05 (3H, m), 7.14 (1H, m), 8.01 (1H, d, J=9.4 Hz), 9.00 (1H, s), 10.79 (1H, s), 11.23 (1H, s).

EXAMPLE 87

N'-[3S-(Allyloxy)-4-(N-hydroxyamino)-2R-(2-naphthylmethyl)succinyl]-S-(S-(4-methoxybenzyl) penicillamide

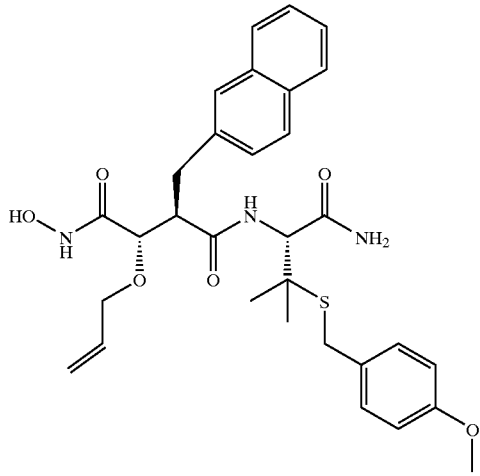

MS (ES+ve) M+H=580, M+Na 602

MS (ES−ve) M−H=578

$^1$H NMR (DMSO-$d_6$): 1.28 (3H, s), 1.29 (3H, s), 2.67 (2H, m), 2.95 (1H, m), 3.24 (1H, m), 3.68–3.86 (6H, m), 3.95 (1H, m), 4.49 (1H, d, J=9.4 Hz), 5.07 (1H, dd, J=1.6 Hz. 10.5 Hz), 5.20 (1H, dd, J=1.7 Hz, 17.4 Hz), 5.78 (1H, m), 6.82 (2H, d, J=8.7 Hz), 6.93 (1H, s), 7.21 (2H, d. J=8.6 Hz), 7.27 (1H, d, J=8.7 Hz), 7.34 (1H, s), 7.45 (2H, m), 7.60 (1H, s), 7.74 (1H, d, J=8.5 Hz), 7.81 (2H, t, J=8.4 Hz), 7.90 (1H, d, J=8.7 Hz), 9.10 (1H, s), 10.95 (1H, s).

EXAMPLE 88

N'-[4-(N-Hydroxyamino)-2R-(2-naphthylmethyl)-3S-(2-i-propoxyethoxy)-succinyl]-S-tert-leucine ethylamide

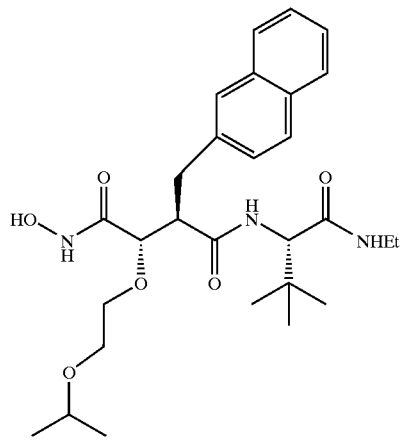

a) N'-[4-t-Butoxy-2R-(2-naphthylmethyl)-3S-(2-i-propoxyethoxy)succinyl]-S-tert-leucine ethylamide

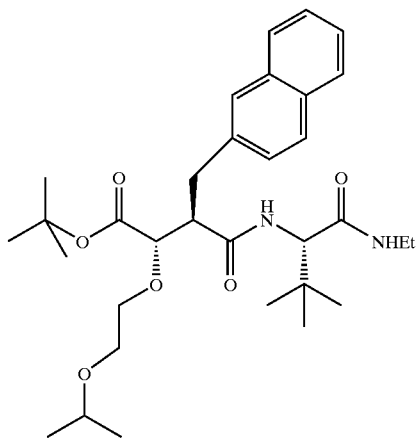

To a solution of N'-[4-t-butoxy-3S-(2-hydroxyethoxy)-2R-(2-naphthylmethyl)succinyl]-S-tert-leucine-N-ethylamide (220 mg, 0.428 mmol) and proton sponge (128 mg, 0.600 mmol) in dichloromethane (2 ml) was added methyltriisopropoxyphosphonium tetrafluoroborate (155 mg, 0.566 mmol). After stirring at room temperature for 3 days, further quantities of proton sponge (128 mg) and methyltriisopropoxyphosphonium tetrafluoroborate (155 mg) were added and the mixture was stirred for a further 24 hrs before addition of further batches of proton sponge (128mg) and methyltriisopropoxyphosphonium tetrafluoroborate (155 mg). After stirring for a further 48 hrs, ethyl acetate and 2N HCl were added and the product was extracted into ethyl acetate. The extracts were washed with sodium bicarbonate solution and brine and then dried (MgSO$_4$) and concentrated. The product was chromatographed on silica gel (elution with ethyl acetate/hexane) to give the product as a gum (141 mg, 59% yield).

MS ES+ve M+H=557, M+Na=579

$^1$H NMR (DMSO-$d_6$): 0.77 (3H, t, J=7.5 Hz), 0.86 (9H, s), 1.07 (3H, d, J=6.0 Hz), 1.08 (3H, d, J=6.0 Hz), 1.44 (9H, s), 2.71–2.83 (3H, m), 2.97 (1H, dd, J=10.0, 14.0 Hz), 3.22 (1H, m), 3.26–3.48 (3H, m), 3.53–3.62 (2H, m), 3.85 (1H, d, J=8.0 Hz), 4.09 (1H, d, J=9.5 Hz), 7.31 (1H, dd, J=1.5, 8.5, Hz), 7.40–7.51 (3H, m), 7.63 (1H, s), 7.70 (1H, d, J=9.5 Hz), 7.75 (1H, d, J=8.5 Hz), 7.76–7.85 (2H, m).

b) N'-[4-(N-Hydroxyamino)-2R-(2-naphthylmethyl)-3S-(2-i-propoxyethoxy)-succinyl]-S-tert-leucine ethylamide.

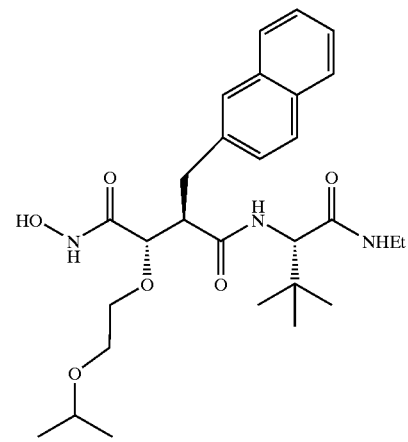

The t-butyl ester was removed with TFA and the resulting carboxylic acid was converted to the hydroxamic acid as above to give the title compound.

MS ES–ve M–H=514
MS ES+ve M+H=516
$^1$H NMR (DMSO-$d_6$): 0.68 (3H, t, J=7.0 Hz), 0.85 (9H, s), 1.06 (6H, d, J=6.0 Hz), 2.50–2.75 (3H, m, partially obscured), 2.85 (1H, m), 3.24 (1H, m), 3.39 (3H, m), 3.45–3.55 (2H, m), 3.80 (1H, d, J=9.5 Hz), 4.03 (1H, d, J=9.5 Hz), 7.26 (2H, m), 7.43 (2H, m), 7.58 (2H, m), 7.72 (1H, d, J=8.5 Hz), 7.75–7.85 (2H, m), 9.09 (1H, s), 10.84 (1H, s).

EXAMPLE 89

N'-[4-(N-Hydroxyamino)-3S-propoxy-2R-[(3R,S-chroman-3-yl)methyl]succinyl]-S-tert-leucine methylamide

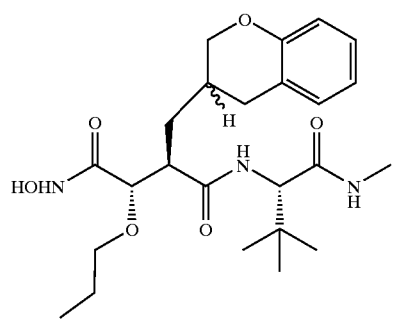

MS (ES+ve) M+H=464
$^1$H NMR (DMSO-$d_6$): 0.79 (3H,m), 0.91 (9H, s), 1.08 (1H, m), 1.40 (3H, m), 1.77 (1H, m), 2.30 (1H, m), 2.39 (1.5H, d), 2.49 (1.5H, d, obscured by DMSO), 2.68 (0.5H, m), 2.98 (1.5H, m), 3.13 (1H, m), 3.28 (1H, m), 3.61 (1.5H, m), 4.01 (0.5H. br.d), 4.19 (2H, m), 6.66 (1H, m), 6.78 (1H, m), 7.00 (2H, m), 7.65 (0.5H, m), 7.76 (0.5H, m), 7.91 (0.5H, d), 7.99 (0.5H, d), 9.02 (1H, s), 10.80 (1H, s).

EXAMPLE 90

N'-[4-(N-Hydroxyamino)-2R-(2-naphthylmethyl)-3S-(propoxy)-succinyl]-S-tert-leucine phenoxyamide

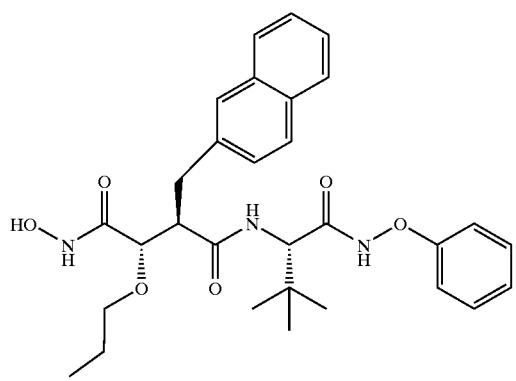

MS (ES–ve) M–H 534
$^1$H NMR (DMSO-$d_6$): 0.84 (3H, t, J=7.4 Hz), 0.95 (9H, s), 1.46 (2H, m), 2.66 (1H, m), 2.96 (1H, m), 3.20 (1H, m), 3.34 (2H, m), 3.78 (1H, d, J=9.6 Hz), 4.22 (1H, d, J=8.8 Hz), 6.88 (2H, d, J=8.0 Hz), 6.95 (1H, m), 7.16. (2H, t, J=7.8 Hz), 7.26 (1H, d, J=8.4 Hz), 7.40 (2H, m), 7.58 (1H, s), 7.68 (2H, m), 7.80 (1H, m), 8.01 (1H, d, J=9.5 Hz), 9.10 (1H, s), 10.92 (1H, s), 11.92 (1H, s).

EXAMPLE 91

N'-[4-(N-Hydroxyamino)-3S-propoxy-2R-(2-naphthylmethyl)succinyl]-S-tert-leucine N-ethoxyamide

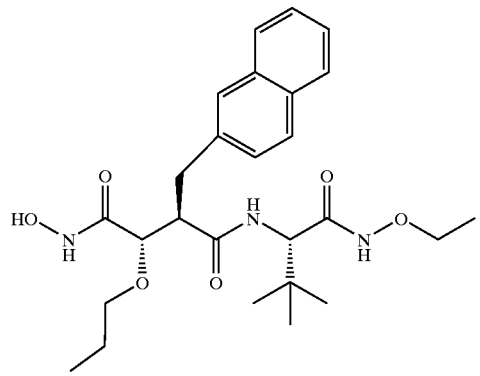

MS (ES+ve) M+H=488
$^1$H NMR (DMSO-$d_6$): 0.83 (1SH, m), 1.44 (2H, m), 2.63 (1H, dd, J=3.5, 13.5 Hz), 2.84 (1H, dd, J=11, 13.5 Hz), 3.25 (5H, m), 3.77 (1H, d, J=6.5 Hz), 3.98 (1H, d, J=9.5 Hz), 7.26 (1H, dd, 1.0, 8.5 Hz), 7.42 (2H, m), 7.70 (1H, s), 7.75 (4H, m), 9.09 (1H, s), 10.78 (1H, s), 10.88 (1H, s).

EXAMPLE 92

N'-[4-(N-Hydroxyamino)-3S-propoxy-2R-(2-naphthylmethyl)succinyl]-S-tert-leucine N-isopropyloxyamide

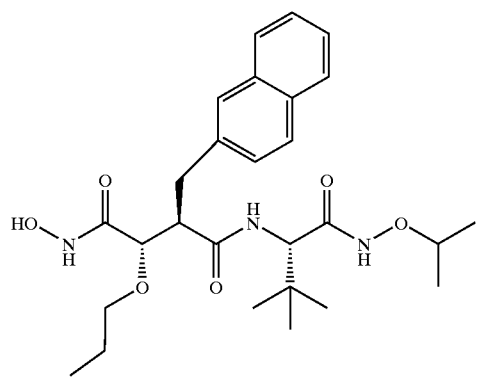

MS (ES+ve) M+H=502
$^1$H NMR (DMSO-$d_6$) 0.85 (18H, m), 1.45 (2H, m), 2.64 (1H, dd, J=3, 13.5 Hz), 2.87 (1H, dd, J=11, 13.5 Hz), 3.19 (1H, m), 3.30 (2H, m), 3.48 (1H, m), 3.76 (1H, d, J=9.5 Hz), 4.03 (1H, d, J=9.5 Hz), 7.26 (1H, dd, J=1.5, 8.4 Hz), 7.42 (2H, m), 7.57 (1H, s), 7.76 (4H, m), 9.09 (1H, s), 10.63 (1H, s), 10.90 (1H, s).

EXAMPLE 93

N'-[4-(N-Hydroxyamino)-2R-(2-naphthylmethyl)-3S-propoxysuccinyl]-S-tert-leucine N,N-dimethylhydrazide

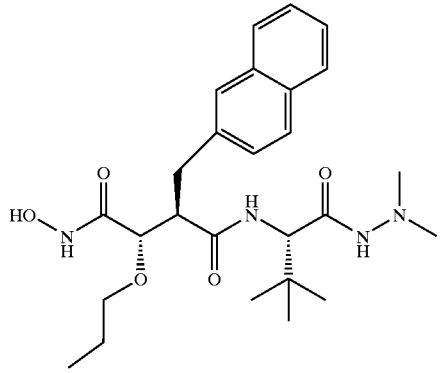

MS (ES+ve) M+H=487

MS(ES−ve) M−H=485, M+TFA=599

$^1$H NMR (DMSO-d$_6$): 0.81 (3H, t, J=7.4 Hz), 0.85 (9H, s), 1.45 (2H, m), 2.21 (6H, s), 2.66 (1H, m), 2.84(1H, s), 3.19 (1H, m), 3.32 (2H, m), 3.76(1H, d, J=9.6 Hz), 3.99 (1H, d, J=9.3 Hz), 7.26. (1H, d, J=8.4 Hz), 7.43 (3H, m), 7.56 (1H, s), 7.70 (2H, m), 7.78 (2H, m), 9.22 (1H, s), 10.88 (1H, s).

EXAMPLE 94

N'-[3S-tert-Butoxy-4-(N-hydroxyamino)-2R-(2-naphthylmethyl)succinyl]-S-tert-leucine cyclopropylamide

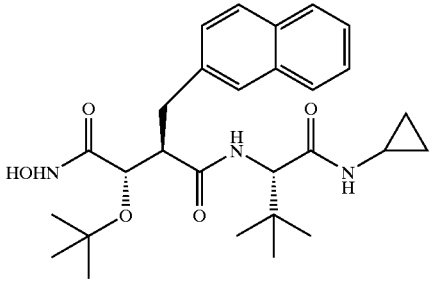

The title product was prepared as previously described (e.g. Example 80) and crystallised from Et$_2$O/EtOAc/MeOH, to give a cream solid, 0.276 g (76%).

MS (ES+ve) M+H=498, M+Na=520.

$^1$H NMR (DMSO-d$_6$): 0.05 (2H, m), 0.38 (2H, m), 0.83 (9H, s), 1.12 (9H, s), 2.10 (1H, m), 2.70 (1H, dd, J=14, 3.5 Hz), 2.84 (1H, dd, J=14, 11 Hz). 3.05 (1H, m), 3.94 (1H, d, J=9.0 Hz), 4.01 (1H, d, J=9.0 Hz), 7.24 (1H, dd, J=8.5, 1.5 Hz), 7.38–7.47 (4H, m), 7.55 (1H, s), 7.73 (1H, d, J=8.5 Hz), 7.80 (2H, m), 8.94 (1H, br. s), 10.69 (1H, br. s).

EXAMPLE 95

N'-[4-(N-Hydroxyamino)-3S-propoxy-2R-(2R,S-(1,2,3,4-tetrahydronaphthyl)methyl)succinyl]-S-tert-leucine methoxyamide

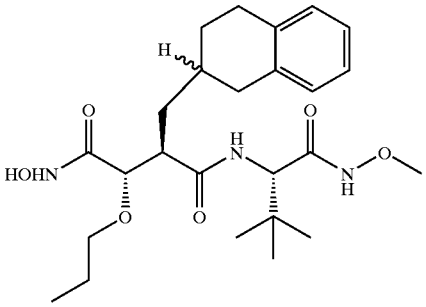

The title product was prepared analogously to Examples 10 and 65 from diethyl (2R,3S)-3-hydroxy-2-[(R/S)-1-(1,2,3,4-tetrahydronaphthalen-2-yl)methyl]succinate and the final compound triturated with Et$_2$O, to give a pale buff solid, 0.396 g (83%).

MS (ES+ve) M+H=478, M+Na=500.

EXAMPLE 96

N'-[4-(N-Hydroxyamino)-3S-isopropoxy-2R-(2-naphthylmethyl)succinyl]-S-tert-leucine methoxyamide

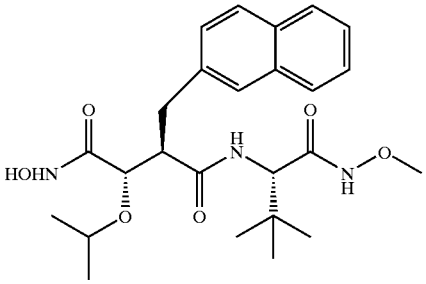

The title product was prepared analogously to Example 65 (alkylating N-[4-t-Butoxy-3S-hydroxy-2R-(2-naphthylmethyl)succinyl]-S-tert-leucine benzyl ester with $^i$PrOTf) and triturating the final compound with Et$_2$O/EtOAc), to give a cream solid, 0.321 g (69%).

MS (ES+ve) M+H=474, M+Na=496.

$^1$H NMR (DMSO-d$_6$): 0.86 (9H, s), 1.00 (3H, d, J=6 Hz), 1.04 (3H, d, J=6 Hz), 2.64 (1H, dd, J=14, 3.5 Hz), 2.86 (1H, dd, J=14, 11 Hz), 3.12 (3H, s), 3.22 (1H, m), 3.51 (1H, m), 3.89 (1H, d, J=9.5 Hz), 3.96 (1H, d, J=9.5 Hz), 7.27 (1H, dd, J=8.5, 1.5 Hz), 7.41 (3H, m), 7.56 (1H, s), 7.71 (2H, m), 7.78 (2H, apparent d, J=9 Hz), 9.08 (1H, s), 10.89 (1H, s), 10.92 (1H, s).

EXAMPLE 97

N'-[4-(N-Hydroxyamino)-3S-propoxy-2R-(2-naphthylmethyl)succinyl]-S-tert-leucine N-tert-butoxyamide

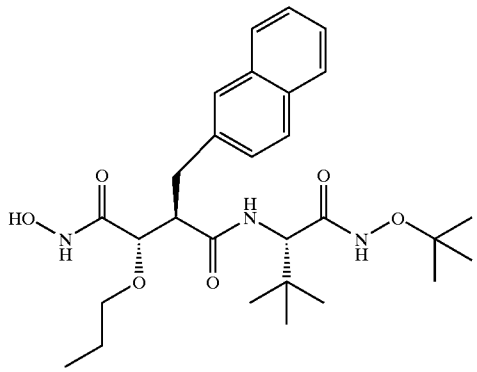

MS (ES+ve) M+H=516

$^1$H NMR (DMSO-d$_6$): 0.82 (3H, t, J=7.5 Hz), 0.86 (9H, s), 0.87 (9H, s), 1.45 (2H, m), 2.62 (1H, dd, J=3.5,13.5 Hz), 2.90 (1H, dd, J=11,13.5 Hz), 3.26 (3H, m), 3.75 (1H, d, J=9.5 Hz), 4.12 (1H, d, J=9.5 Hz), 7.24 (1H, m), 7.41 (2H, m), 7.55 (1H, s), 7.71 (2H, m), 7.78 (2H, m), 9.08 (1H, s), 10.14 (1H, s), 10.89 (1H, s).

EXAMPLE 98

N'-[3S-tert-Butoxy-4-(N-hydroxyamino)2R-(2R,S-(1,2,3,4-tetrahydronaphthyl)methyl)succinyl]-S-tert-leucinamide

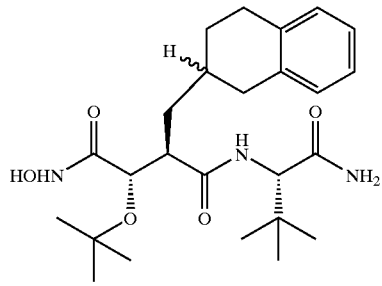

The title product was prepared analogously to Examples 10 and 81 from diethyl (2R,3S)-3-hydroxy-2-[(R,S)-1-(1,2,3,4-tetrahydronaphthalen-2-yl)methyl]succinate.

MS (ES+ve) M+H=462, M+Na=484.

EXAMPLE 99

N'-[4-(N-Hydroxyamino)-2R-(5-methylbenzo[6]thiophene)-3S-propoxysuccinyl]-N-methyl-S-tert-leucinamide

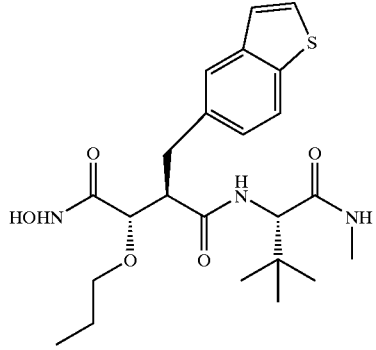

A solution of N'-[4-Hydroxy-2R-(5-methylbenzo[6]thiophene)-3S-propoxysuccinyl]-N-methyl-S-tert-leucinamide (60 mg, 0.13 mmol) in anhydrous DMF (5 ml) was treated sequentially with HOAT (36 mg, 0.27 mmol) and EDC (51 mg, 0.27 mmol), and the reaction solution was stirred at room temperature for 0.25 h. Hydroxylamine hydrochloride (28 mg, 0.40 mmol) and N-methylmorpholine (0.04 ml, 0.40 mmol) were then added and the reaction solution was stirred for 3 h at room temperature. The reaction solution was evaporated to dryness and the residue was partitioned between ethyl acetate and water. The phases were separated and the organic phase was washed with further water and satd. sodium bicarbonate solution and dried with brine and over magnesium sulfate. The organic phase was then evaporated and triturated with diethyl ether to give the hydroxamic acid as a white solid (15 mg, 24%).

MS (ES+ve) [M−H]$^+$=463

$^1$H NMR (DMSO-d6): 0.89 (9H, s), 0.91 (3H, t, J=7.0 Hz), 1.57 (2H, m), 2.24 (3H, d, J=4.9 Hz), 2.82 (2H, m), 3.07 (1H, m), 3.31 (2H, m), 3.84 (1H, d, J=9.2 Hz), 4.05 (1H, s), 7.14 (1H, d, J=5.3 Hz),), 7.22 (1H, q, J=5.6 Hz), 7.27 (1H, d, J=3.4 Hz), 7.50 (1H, d, J=3.4 Hz), 7.53 (1H, t, J=6.0 Hz), 7.59 (1H, s), 7.75 (1H, d, J=5.3 Hz), 9.11 (1H, s), 10.96 (1H, s).

EXAMPLE 100

N'-[4-(N-Hydroxyamino)-3S-cyclohexyloxy-2R-(2-naphthylmethyl)succinyl]-S-tert-leucine N-methoxyamide

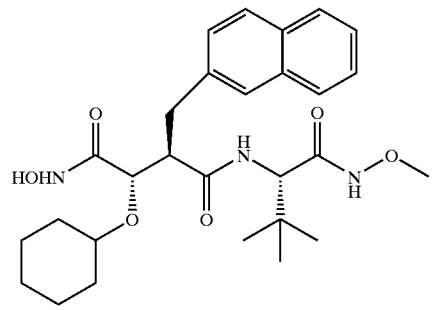

MS(ES+ve)M+H=514 $^1$H NMR (DMSO-d$_6$) 0.86 (9H, s), 1.00–1.22 (5H, m), 1.45 (1H, m), 1.63 (2H, m), 1.76 (1H, m), 1.87 (1H, m), 2 67 (1H, J=3.5,13.5 Hz), 2.85 (1H, dd, J=13.5,11 Hz), 3.13 (3H, s), 3.21 (2H, m), 3.95 (2H, m), 7.28 (1H, m), 7.41 (2H, m), 7.56 (1H, s), 7.72 (2H, m), 7.78 (2H, m), 9.07 (iH, s), 10.84 (1H, s), 10.90 (1H, s).

What is claimed is:

1. A compound of formula (I):

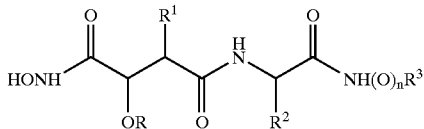

wherein:
R is methyl substituted by one to three groups selected from alkyl, aryl, alkenyl, and alkynyl;
n is 0 or 1;
$R^1$ is arylmethyl or heterocyclylmethyl;
$R^2$ is alkyl, alkenyl, aryl, cycloalkyl or cycloalkenyl; and
$R^3$ is hydrogen, alkyl, alkenyl, alkynyl or aryl.

2. A compound according to claim 1, wherein:
R is selected from the group consisting of allyl, propyl, ethyl and isopropyl,
$R^1$ is 1- or 2-naphthylmethyl,
$R^2$ is t-butyl, and
$R^3$ is hydrogen or methyl.

3. A compound according to claim 1 wherein
n is 1 or 0,
R is selected from the group consisting of allyl, propyl, ethyl, hexyl, 4-fluorobenzyl, benzoyl, N,N-dimethylacetamide, N-t-butylacetamide, N-phenylcarbamoyl, N-methyl-N-phenylcarbamoyl, cyclohexyl, 3-phenylpropyl, thiazol-2-ylmethyl, cyclohexylcarbonyl, t-butylcarbonyl, methyl, propanoyl, 2-methylpropyl, t-butyl, N-(2-dimethylaminoethyl)-acetamido, N-(2'-acetoxyethyl) acetamido, N-(2-hydroxyethyl)carbamoylmethyl, phenacyl, 3-acetoxypropyl, 3-hydroxypropyl, 3-dimethylaminopropyl, 2-(R/S)-acetoxypropyl, 2-(R/S)-hydroxypropyl, 2-acetoxyethyl, 2-hydroxyethyl, 2-N-succinimidylethyl, 2-dimethylaminoethyl, 2-acetoxyethyl, 2-dimethylaminoethyl, 2-(1-imidazolyl)ethyl, 2-methoxyethyl, 2-hydroxy-2-phenylethyl, 2-(morpholin-4-yl)-2-oxoethyl, 2-(4-methyl-piperazin-1-yl)-2-oxoethyl, (1,2,4-oxadiazol-3-yl)methyl, 2-i-propoxyethyl, and isopropyl;
$R^1$ is selected from the group consisting of 2-naphthylmethyl, 2-(7-fluoro)naphthylmethyl, 2-(6-fluoro)naphthylmethyl, 2-quinolinylmethyl, 2-benzothiophenylmethyl, 2-(1,2,3,4-tetrahydro) naphthylmethyl, (4-benzocycloheptyl)methyl, (3-benzocyclopentyl)methyl, 3-chromanylmethyl, and 5-methylbenzo[6]thiophenyl);
$R^2$ is selected from t-butyl, 2-(2-methyl)N-methylpentylamine, N,N-dimethylbutylamine, and 1-methyl-1-(4-methoxybenzylsulfanyl)ethyl; and
$R^3$ is selected from hydrogen, methyl, ethyl, N,N-dimethylaminoeth-2-yl, isopropyl, 2,2,2-trifluoroethyl, cyclopropyl, phenyl, dimethylamino, and t-butyl.

4. A compound according to claim 1 selected from the group consisting of:
N'-[3S-(Allyloxy)-4-(N-hydroxyamino)-2R-(2-naphthylmethyl)succinyl]-S-tert-leucinamide
N'-[3S-(Allyloxy)-4-(N-hydroxyamino)-2R-(2-naphthylmethyl)succinyl]-S-tert-leucine methylamide
N'-[4-(N-Hydroxyamino)-2R-(2-naphthylmethyl)-3S-(propyloxy)succinyl]-S-tert-leucine methylamide
N'-[4-(N-Hydroxyamino)-2R-(2-naphthylmethyl)-3S-(propyloxy)succinyl]-S-tert-leucinamide
N'-[3S-(Allyloxy)-4-(N-hydroxyamino)k-2R-(2-(7-fluoro-) naphthylmethyl)succinyl]-S-tert-leucinamide
N'-[3S-(Ethoxy)-4-(N-hydroxyamino)-2R-(2-(7-fluoro-) naphthylmethyl)succinyl]-S-tert-leucinamide
N'-[4-(N-Hydroxyamino)-2R-(2-(7-fluoro) naphthylmethyl)-3S-(propyloxy)succinyl]-S-tert-leucinamide
N'-[3S-(Ethoxy)-4-(N-hydroxyamino)-2R-(2-naphthylmethyl)succinyl]-S-tert-leucinamide
N'-[4-(N-Hydroxyamino)-2R-(2-naphthylmethyl)-3S-(propyloxy)succinyl]-S-(β,β-dimethyl-Nε-methyllysinamide), TFA salt
N'-[4-(N-Hydroxyamino)-2R-(2-(6-fluoro) naphthylmethyl)-3S-(propyloxy)-succinyl]-S-tert-leucinamide
N'-[3S-(Allyloxy)-4-(N-Hydroxyamino)-2R-(2-(6-Fluoro-)naphthylmethyl)succinyl]-S-tert-leucinamide
N'-[3S-(Hexyloxy)-4-(N-Hydroxyamino)-2R-(2-(6-Fluoro-)naphthylmethyl)succinyl]-S-tert-leucinamide
N'-[3S-((4-Fluoro)benzyloxy)-4-(N-hydroxyamino)-2R-(2-naphthylmethyl)succinyl]-S-tert-leucinamide
N'-[3S-((4-Fluoro)benzyloxy)-4-(N-hydroxyamino)-2R-(2-(6-fluoro)naphthylmethyl)succinyl]-S-tert-leucinamide
N'-[3S-Benzoyloxy-4-(N-hydroxyamino)-2R-(2-naphthylmethyl)succinyl]-S-tert-leucinamide
N'-[3S-(2-(N,N-Dimethylacetamidoxy))-4-(N-hydroxyamino)-2R-(2-naphthylmethyl)succinyl]-S-tert-leucinamide
N'-[3S-(2-(N-t-Butylacetamidoxy))-4-(N-hydroxyamino)-2R-(2-naphthylmethyl)succinyl]-S-tert-leucinamide
N'-[4-(N-Hydroxyamino)-2R-(2-naphthylmethyl)-3S-(N-phenylcarbamoyloxy)-succinyl]-S-tert-leucinamide
N'-[4-(N-Hydroxyamino)-3S-(N-methyl-N-phenylcarbamoyloxy)-2R-(2-naphthylmethyl)-succinyl]-S-tert-leucinamide
N'-[3S-(Cyclohexyloxy)-4-(N-hydroxyamino)-2R-(2-naphthylmethyl)succinyl]-S-tert-leucinamide
N'-[3S-(Cyclohexyloxy)-4-(N-hydroxyamino)-2R-(2-naphthylmethyl)succinyl]-S-tert-leucine ethylamide
N'-[3S-(Ethoxy)-4-(N-hydroxyamino)-2R-(2-naphthylmethyl)succinyl]-S-tert-leucine methylamide
N'-[4-(N-Hydroxyamino)-2R-(2-Naphthylmethyl)-3S-((3-phenyl)propyloxy)-succinyl]-S-tert-leucinamide
N'-[4-(N-Hydroxyamino)-2R-(2-naphthylmethyl)-3S-(thiazol-2-ylmethoxy)succinyl]-S-tert-leucinamide
N'-[3S-(Cyclohexylcarbonyloxy)-4-(N-hydroxyamino)-2R-(2-naphthylmethyl)succinyl]-S-tert-leucinamide
N'-[3S-(t-Butylcarbonyloxy)-4-(N-hydroxyamino)-2R-(2-naphthylmethyl)succinyl]-S-tert-leucinamide
N'-[3S-benzoyloxy-4-(N-hydroxyamino)-2R-(2-naphthylmethyl)succinyl]-S-tert-leucinamide
N'-[3S-(Ethoxy)-4-(N-hydroxyamino)-2R-(2-quinolinylmethyl)succinyl]-S-tert-leucine methylamide
N'-[4-(N-Hydroxyamino)-3S-methoxy-2R-(2-naphthylmethyl)succinyl]-S-tert-leucine methylamide
N'-[4-(N-Hydroxyamino)-2R-(2-naphthylmethyl)succinyl-3S-propanoyloxy)-S-tert-leucine methylamide
N'-[3S-(Ethoxy)-4-(N-hydroxyamino)-2R-(2-naphthylmethyl)succinyl]-S-tert-leucine ethylamide
N'-[4-(N-Hydroxyamino)-2R-(2-naphthylmethyl)-3S-(2-methylpropoxy)succinyl]-S-tert-leucine methylamide
N'-[4-(N-Hydroxyamino)-2R-(2-naphthylmethyl)-3S-propoxysuccinyl]-S-tert-leucine ethylamide N'-[3S-tert-Butoxy-4-(N-hydroxyamino)-2R-(2-naphthylmethyl)succinyl]-S-tert-leucine methylamide N'-[3S-tert-Butoxy-4-(N-hydroxyamino)-2R-(2-naphthylmethyl)succinyl]-S-tert-leucine ethylamide N"-[4-(N-Hydroxyamino)-3S-(2-oxy-N-(N',N'-2-dimethylaminoethyl)acetamido)-2R-(2-naphthylmethyl)succinyl]-S-tert-leucine methylamide N'-[4-(N-Hydroxyamino)-3S-(2-oxy-N-(2'-acetoxyethyl)acetamido)-2R-(2-naphthylmethyl)succinyl]-S-tert-leucine methylamide N'-[4-(N-Hydroxyamino)-3S-N-(2-hydroxyethyl)carbamoylmethoxy-2R-(2-naphthylmethyl)succinyl]-S-tert-leucine methylamide N'-[4-(N-Hydroxyamino)-2R-(2-naphthylmethyl)succinyl-3S-(2-oxy phenacyl)]-S-tert-leucine methylamide N'-[3S-(3-Acetoxypropoxy)-4-(N-hydroxyamino)-2R-(2-naphthylmethyl)succinyl]-S-tert-leucine methylamide N'-[4-(N-Hydroxyamino)-3S-(3-hydroxypropoxy)-2R-(2-naphthylmethyl)-succinyl]-S-tert-leucine methylamide N'-[3S-(3-Dimethylaminopropoxy)-4-(N-hydroxyamino)-2R-(2-naphthylmethyl)succinyl]-S-tert-leucine methylamide N'-[3S-(2-RS-Acetoxypropoxy)-4-(N-hydroxyamino)-2R-(2-naphthylmethyl)-succinyl]-S-tert-leucine methylamide N'-[4-(N-Hydroxyamino)-3S-(2-RS-hydroxypropoxy)-2R-(2-naphthylmethyl)-succinyl]-S-tert-leucine methylamide N'-[4-t-Butoxy-3S-(2-hydroxyethoxy)-2R-(2-naphthylmethyl)succinyl]-S-tert-leucine methylamide N'-[3S-(2-Acetoxyethoxy)-4-(N-hydroxyamino)-2R-(2-naphthylmethyl)-succinyl]-S-tert-leucine methylamide N'-[4-(N-Hydroxyamino)-3S-(2-hydroxyethoxy)-2R-(2-naphthylmethyl)-succinyl]-S-tert-leucine methylamide N'-[4-(N-Hydroxyamino)-2R-(2-naphthylmethyl)-3S-(2-N-succinimidylethoxy)succinyl]-S-tert-leucine methylamide N'-[3S-(2-Dimethylaminoethoxy)-4-(N-hydroxyamino)-2R-(2-naphthylmethyl)succinyl]-S-tert-leucine methylamide N'-[3S-(2-Acetoxyethoxy)-4-(N-hydroxyamino)-2R-(2-naphthylmethyl)-succinyl]-S-tert-leucine ethylamide N'-[4-(N-Hydroxyamino)-3S-(2-hydroxyethoxy)-2R-(2-naphthylmethyl)-succinyl]-S-tert-leucine ethylamide N'-[3S-(2-Dimethylaminoethoxy)-4-(N-hydroxyamino)-2R-(2-naphthylmethyl)succinyl]-S-tert-leucine ethylamide N'-[4-(N-hydroxyamino)-3S-(2-(1-imidazolyl)ethoxy)-2R-(2-naphthylmethyl)-succinyl]-S-tert-leucine ethylamide N'-[4-(N-Hydroxyamino)-3S-(2-methoxyethoxy)-2R-(2-naphthylmethyl)-succinyl]-S-tert-leucine ethylamide N'-[3S-Ethoxy-4-(N-hydroxyamino)-2R-(2-benzothiophenylmethyl)succinyl]-S-tert-leucine methylamide N'-[4-(N-Hydroxyamino)-3S-cyclohexyloxy-2R-(2-naphthylmethyl)succinyl]-S-tert-leucine methylamide N'-[4-(N-Hydroxyamino)-3S-(2-hydroxy-2-phenylethoxy)-2R-(2-naphthylmethyl)succinyl]-S-tert-leucine methylamide N'-[4-(N-Hydroxyamino)-3S-[2-(morpholin-4-yl)-2-oxoethoxy]-2R-(2-naphthylmethyl)succinyl]-S-tert-leucine methylamide N'-[4-(N-Hydroxyamino)-3S-ethoxy-2R-(2-naphthylmethyl)succinyl]-S-(N,N-dimethyl lysine) methylamide N'-[4-(N-Hydroxyamino)-3S-propoxy-2R-(2-naphthylmethyl)succinyl]-S-(N,N-dimethyl-β,β-dimethyl-lysine)ethylamide N'-[4-(N-Hydroxyamino)-3S-[2-(4-methyl-piperazin-1-yl)-2-oxo-ethoxy]-2R-(2-naphthylmethyl)succinyl]-S-tert-leucine methylamide N'-[4-(N-Hydroxyamino)-3S-ethoxy-2R-(2-naphthylmethyl)succinyl]-S-tert-leucine t-butylamide N'-[4-(N-Hydroxyamino)-3S-allyloxy-2R-(2-naphthylmethyl)succinyl]-S-tert-leucine t-butylamide N'-[4-(N-Hydroxyamino)-3S-propoxy-2R-(2-naphthylmethyl)succinyl]-S-tert-leucine t-butylamide N'-[4-(N-Hydroxyamino)-3S-allyloxy-2R-(2-naphthylmethyl)succinyl]-S-tert-leucine benzyl ester N'-[4-(N-Hydroxyamino)-3S-propoxy-2R-(2-naphthylmethyl)succinyl]-S-tert-leucine methoxyamide N'-[4-(N-Hydroxyamino)-3S-propoxy-2R-(2-naphthylmethyl)succinyl]-S-tert-leucine (N,N-dimethylaminoeth-2-yl)amide N'-[4-(N-Hydroxyamino)-3S-propoxy-2R-(2-naphthylmethyl)succinyl]-R-tert-leucine (N,N-dimethylaminoeth-2-yl)amide N'-[4-(N-Hydroxyamino)-3S-ethoxy-2R-(2-naphthylmethyl)succinyl]-S-(O-benzyl) tert-leucinol N'-[4-(N-Hydroxyamino)-3S-propoxy-2R-[S-1-(1,2,3,4-tetrahydronaphthalen-2-yl)methyl)succinyl]-S-tert-leucine methylamide N'-[3S-(Ethoxy)-4-(N-hydroxyamino)-2R-(2-quinolinylmethyl)succinyl]-S-tert-leucine ethylamide N'-[4-(N-Hydroxyamino)-3S-(propoxy)-2R-(2-quinolinylmethyl)succinyl]-S-tert-leucine ethylamide N'-[3S-(Ethoxy)-2R-(2-(6-fluoro-)naphthylmethyl)-4-(N-hydroxyamino)succinyl]-S-tert-leucine ethylamide N'-[4-(N-Hydroxyamino)-3S-allyloxy-2R-(2-naphthylmethyl)succinyl]-S-tert-leucine methyl ester N'-[4-(N-Hydroxyamino)-2R-(2-naphthylmethyl)-3S-propoxy succinyl]-S-tert-leucine isopropylamide N'-[3S-Ethoxy-4-(N-hydroxyamino)-2R-(2-naphthylmethyl)succinyl]-S-tert-leucine isopropylamide N'-[3S-Ethoxy-4-(N-hydroxyamino)-2R-(2-naphthylmethyl)succinyl]-S-tert-leucine (2,2,2-trifluoroethyl)amide N'-[3S-Ethoxy-4-(N-hydroxyamino)-2R-(2-naphthylmethyl)succinyl]-S-tert-leucine (2,2,2-trifluoroethyl)amide N'-[4-(N-Hydroxyamino)-3S-propoxy-2R-[S or R-1-(1,2,3,4-tetrahydronaphthalen-2-yl)methyl)succinyl]-S-tert-leucinamide N'-[2R-(2-(6-Fluoronaphthyl)methyl)-4-(N-hydroxyamino)-3S-propoxy succinyl]-S-tert-leucine ethylamide N'-[3S-Ethoxy-4-(N-hydroxyamino)-2R-(2-naphthylmethyl)succinyl]-S-tert-leucine cyclopropylamide N'-[3S-tert-Butoxy-4-(N-hydroxyamino)-2R-(2-naphthylmethyl)succinyl]-S-tert-leucinamide N'-[4-(N-Hydroxyamino)-3S-(1,2,4-oxadiazol-3-yl)methoxy)-2R-(2-naphthylmethyl)succinyl]-S-tert-leucine methylamide N'-[4-(N-Hydroxyamino)-3S-(2-thiazolylmethoxy)-2R-(2-naphthylmethyl)succinyl]-S-tert-leucine methylamide N'-[2R-(4-Benzocycloheptyl)methyl-4-(N-hydroxyamino)-3S-(propoxy)succinyl]-S-tert-leucine methylamide N'-[2R-(3-Benzocyclopentyl)methyl-4-(N-hydroxyamino)-3S-(propoxy)succinyl]-S-tert-leucine methylamide N'-[2R-(3-Benzocyclopentyl)methyl-4-(N-hydroxyamino)-3S-(propoxy)succinyl]-S-tert-leucine methoxyamide N'-[3S-(Allyloxy)-4-(N-hydroxyamino)-2R-(2-naphthylmethyl)succinyl]-S-(S-(4-methoxybenzyl) penicillamide N'-[4-(N-Hydroxyamino)-2R-(2-naphthylmethyl)-3S-(2-i-propoxyethoxy)-succinyl]-S-tert-leucine ethylamide N'-[4-(N-Hydroxyamino)-3S-propoxy-2R-[(3R,S-chroman-3-yl)methyl]succinyl]-S-tert-leucine methylamide N'-[4-(N-Hydroxyamino)-2R-(2-naphthylmethyl)-3S-(propoxy)-succinyl]-S-tert-leucine phenoxyamide N'-[4-(N-Hydroxyamino)-3S-propoxy-2R-(2-naphthylmethyl)succinyl]-S-tert-leucine N-ethoxyamide N'-[4-(N-Hydroxyamino)-3S-propoxy-2R-(2-naphthylmethyl)succinyl]-S-tert-leucine N-isopropyloxyamide N'-[4-(N-Hydroxyamino)-2R-(2-naphthylmethyl)-3S-propoxysuccinyl]-S-tert-leucine N,N-dimethylhydrazide N'-[3S-tert-Butoxy-4-(N-hydroxyamino)-2R-(2-naphthylmethyl)succinyl]-S-tert-leucine cyclopropylamide N'-[4-(N-Hydroxyamino)-3S-propoxy-2R-(2R,S-(1,2,3,4-tetrahydronaphthyl)methyl)succinyl]-S-tert-leucine methoxyamide N'-[4-(N-Hydroxyamino)-3S-isopropoxy-2R-(2-naphthylmethyl)succinyl]-S-tert-leucine methoxyamide N'-[4-(N-Hydroxyamino)-3S-propoxy-2R-(2-naphthylmethyl)succinyl]-S-tert-leucine N-tert-butoxyamide N'-[3S-tert-Butoxy-4-(N-hydroxyamino)2R-(2R,S-(1,2,3,4-tetrahydronaphthyl)methyl)succinyl]-S-tert-leucinamide N'-[4-(N-Hydroxyamino)-2R-(5-methylbenzo[6]thiophene)-3S-propoxy-succinyl]-N-methyl-S-tert-leucinamide and N'-[4-(N-Hydroxyamino)-3S-cyclohexyloxy-2R-(2-naphthylmethyl)succinyl]-S-tert-leucine N-methoxyamide.

5. A compound according to claim 1, having formula (IA):

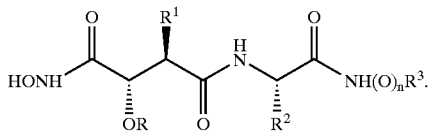

(IA)

6. A method for the treatment of disorders in which the overproduction of s-CD23 is implicated, which method comprises the administration of a compound according to claim 1 to a human or non-human mammal in need thereof.

7. A pharmaceutical composition for the treatment of disorders in which the overproduction of s-CD23 is implicated which comprises a compound according to claim 1 and optionally a pharmaceutically acceptable carrier therefor.

8. A method for the treatment of conditions mediated by TNF, which method comprises the administration of a compound according to claim 1 to a human or non-human mammal in need thereof.

9. A process for preparing a compound of formula (I), which process comprises:

(a) deprotecting a compound of formula (II):

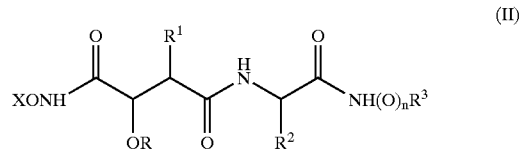

(II)

wherein n and R to $R^3$ are as defined hereinabove in claim 1 and X is protecting group or (b) reacting a compound of formula (III):

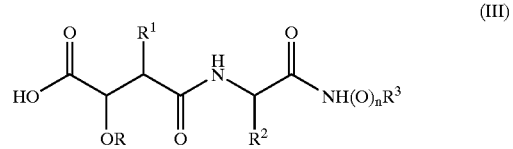

(III)

wherein n and R to $R^3$ are as defined hereinabove in claim 1, and any hydroxy group is optionally protected, with hydroxylamine or a salt thereof, or (c) converting a compound of formula (I) to a different compound of formula (I) as defined hereinabove.

10. A compound of formula (II)

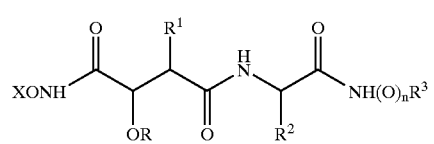

(II)

wherein n and R to $R^3$ are as defined hereinabove in claim 1.

11. A compound of formula (III)

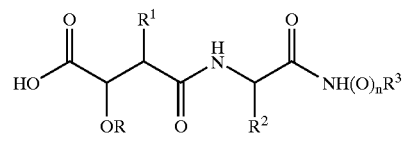

III wherein n and R to $R^3$ are as defined above in claim 1.

12. A method according to claim 7 wherein the disorder is an allergy, and inflammatory disorder or an autoimmune disease.

13. A method according to claim 10 wherein the conditions are selected from the group consisting of inflammation, fever, cardiovascular effects, haemorrhage, coagulation and acute phase response, cachexia and anorexia, acute infections, shock states, graft versus host reactions and autoimmune disease.

* * * * *